United States Patent
Ge et al.

(10) Patent No.: US 11,098,314 B2
(45) Date of Patent: Aug. 24, 2021

(54) FUNGAL GENOME MODIFICATION SYSTEMS AND METHODS OF USE

(71) Applicant: Danisco US Inc., Palo Alto, CA (US)

(72) Inventors: Jing Ge, Palo Alto, CA (US); Xiaogang Gu, Palo Alto, CA (US); Susan Mampusti Madrid, Palo Alto, CA (US); Danfeng Song, Palo Alto, CA (US); Mingmin Song, Palo Alto, CA (US); Michael Ward, Palo Alto, CA (US)

(73) Assignee: DANISCO US INC, Palo Alto, CA (US)

( * ) Notice: Subject to any disclaimer, the term of this patent is extended or adjusted under 35 U.S.C. 154(b) by 475 days.

(21) Appl. No.: 15/536,872

(22) PCT Filed: Dec. 16, 2015

(86) PCT No.: PCT/US2015/066195
§ 371 (c)(1),
(2) Date: Jun. 16, 2017

(87) PCT Pub. No.: WO2016/100571
PCT Pub. Date: Jun. 23, 2016

(65) Prior Publication Data
US 2017/0369891 A1 Dec. 28, 2017

(30) Foreign Application Priority Data

Dec. 16, 2014 (WO) ................ PCT/CN2014/093914
Dec. 16, 2014 (WO) ................ PCT/CN2014/093916
Dec. 16, 2014 (WO) ................ PCT/CN2014/093918

(51) Int. Cl.
*C12N 15/80* (2006.01)
*C12N 9/22* (2006.01)
*C12N 15/11* (2006.01)

(52) U.S. Cl.
CPC ............ *C12N 15/80* (2013.01); *C12N 9/22* (2013.01); *C12N 15/11* (2013.01); *C12N 2310/20* (2017.05)

(58) Field of Classification Search
None
See application file for complete search history.

(56) References Cited

FOREIGN PATENT DOCUMENTS

| WO | 2015054507 A1 | 4/2015 | |
| WO | WO-2015054507 A1 * | 4/2015 | ............. C12N 15/80 |

OTHER PUBLICATIONS

DiCarlo et al., Nucleic Acids Research (2013) vol. 41, pp. 4336-4343. (Year: 2013).*
Krappman, Fungal Biol. Rev., 21: 25-29 (Year: 2007).*
Arazoe et al, FEMS Microbiol. Lett., 352, 2, 221-229 (Year: 2014).*
Sorek et al., "CRISPR-Mediated Adaptive Immune Systems in Bacteria and Archaea" 82 Annual Review of Biochemistry 237-266 (Year: 2013).*
Koonin et al., "Diversity, classification and evolution of CRISPR-Cas systems" 37 Current Opinion in Microbiology 67-78 (Year: 2017).*
Basak Anindita et al, "A pseudouridine residue in the spliceosome core is part of the filamentous growth program in yeast.", Cell Reports Aug. 21, 2014,vol. 8, No. 4, Aug. 21, 2014 (Aug. 21, 2014), p. 966-973.
Chandler Julie M et al, "Protein profiling of the dimorphic, pathogenic fungus, Penicillium marneffei", Proteome Science, Biomed Central, London, GB,No. 1, Jun. 4, 2008 (Jun. 4, 2008), p. 17.
Dewei Jiang et al, "Molecular tools for functional genomics in filamentous fungi: Recent advances and new strategies", Biotechnology Advances.,vol. 31, No. 8, Dec. 1, 2013 (Dec. 1, 2013), p. 1562-1574.
Prashant Mali et al, "Cas9 as a versatile tool for engineering biology", Nature Method, Oct. 1, 2013 (Oct. 1, 2013), vol. 10, No. 10, p. 957-963.
Fuller Kevin K et al, "Development of the CRISPR/Cas9 System for Targeted Gene Disruption in Aspergillus fumigatus.", Eukaryotic Cell Nov. 2015,vol. 14, No. 11, Nov. 2015 (Nov. 2015), p. 1073-1080.
Rui Liu, Ling Chen, Yanping Jiang, Zhihua Zhou, Gen Zou, "Efficient genome editing in filamentous fungus Trichoderma reesei using the CRISPR/Cas9 system", Cell Discovery,vol. 1, May 12, 2015 (May 12, 2015), p. 1-11.
Christina S. Nødvig et al, "A CRISPR-Cas9 System for Genetic Engineering of Filamentous Fungi", PLOS ONE,vol. 10, No. 7, Jul. 15, 2015 (Jul. 15, 2015), p. e0133085.
P. Mali et al, "RNA-Guided Human Genome Engineering via Cas9", Science, vol. 339, No. 6121, Jan. 3, 2013 (Jan. 3, 2013), p. 823-826.
Takayuki Arazoe et al, "Tailor-made CRISPR/Cas system for highly efficient targeted gene replacement in the rice blast fungus", Biotechnology and Bioengineering, vol. 112, No. 12, Dec. 14, 2015 (Dec. 14, 2015), p. 2543-2549.
Chi Zhang et al, "Highly efficient CRISPR mutagenesis by microhomology-mediated end joining in Aspergillus fumigatus", Fungal Genetics and Biology,vol. 86, Dec. 14, 2015 (Dec. 14, 2015), p. 47-57.
De Boer P et al, "Highly efficient gene targeting in Penicillium chrysogenum using the bi-partite approach in DELTAlig4 or DELTAku70 mutants", Oct. 1, 2010 (Oct. 1, 2010), vol. 47, No. 10, p. 839-846.
Takayuki Arazoe et al, "Site-specific DNA double-strand break generated by I-SceI endonuclease enhances ectopic homologous recombination in Pyricularia oryzae", FEMS Microbiology Letters,vol. 352, No. 2, Feb. 26, 2014 (Feb. 26, 2014), p. 221-229.

(Continued)

*Primary Examiner* — Nancy J Leith

(57) ABSTRACT

Compositions and methods are provided for genome modification at a target site in the genome of a fungal cell. Aspects of methods and compositions are drawn to a guide polynucleotide/Cas endonuclease system for promoting insertion of a donor DNA at a desired target site in a fungal host cell genome.

16 Claims, 5 Drawing Sheets

Specification includes a Sequence Listing.

(56) References Cited

OTHER PUBLICATIONS

J. E. Dicarlo et al, "Genome engineering in *Saccharomyces cerevisiae* using CRISPR-Cas systems", Nucleic Acids Research, vol. 41, No. 7, Mar. 4, 2013 (Mar. 4, 2013), p. 4336-4343.

Yoshizui Ishino et al., Nucleotide Sequence of the iap Gene, Responsible for Alkaline Phosphatase Isozyme Conversion in *Escherichia coli*, and Identification of the Gene Product, Journal of Bacteriology, Dec. 1987, pp. 5429-5433.

Atsuo Nakata et al., Unusual Nucleotide Arrangement with Repeated Sequences in the *Escherichia coli* K-12 Chromosome, Journal of Bacteriology, Jun. 1989, pp. 3553-3556, vol. 171, No. 6.

Peter M. A. Groenen et al., Nature of DNA polymorphis in the direct repeat cluster of *Mycobacterium tuberculosis;* application for strain differentiation by a novel typing method, Molecular Microbiology, 1993, pp. 1057-1065, vol. 10, No. 5.

Nancy Hoe et al., Rapid Molecular Genetic Subtyping of Serotype M1 Group A *Streptococcus* Strains, Emerging Infectious Diseases, Mar.-Apr. 1999, pp. 254-263, vol. 5, No. 2.

Bernd Masepohl et al., Long tandemly repeated repetitive (LTRR) sequences in the filamentous cyanobacterium *Anabaena* sp. PCC7120, Biochimica et Biophysica Acta, 1996, pp. 26-30.

F. J. M. Mojica et al., Long stretches of short tandem repeats are present in the largest replicons of the Archaea Haloferax mediterranei and Haloferax volcanii and could be involved in replicon partitioning, Molecular Microbiology, 1995, pp. 85-93, vol. 17, No. 1.

Norah Rudin et al., Genetic and Physical Analysis of Double-Strand Break Repair and Recombination in *Saccharomyces cerevisiae*, Genetics, Jul. 1989, pp. 519-534, vol. 122.

Fatima Smih et al., Double-strand breaks at the target locus stimulate gene targeting in embryonic stem cells, Nucleic Acids Research, 1995, pp. 5012-5019, vol. 23, No. 24.

Patrick D. Hsu et al., Development and Applications of CRISPR-Cas9 for Genome Engineering, Cell, Jun. 5, 2014, pp. 1262-1278, vol. 157.

Bernd Zetsche et al., Cpf1 Is a Single RNA-Guided Endonuclease of a Class 2 CRISPR-Cas System, Cell, Oct. 22, 2015, pp. 759-771, vol. 163.

Jean-Yves Bleuyard et al., Recent advances in understanding of the DNA double-strand break repair machinery of plants, DNA Repair, 2006, pp. 1-12, vol. 5.

Ralph Siebert et al., Efficient Repair of Genomic Double-Strand Breaks by Homologous Recombination between Directly Repeated Sequences in the Plant Genome, The Plant Cell, May 2002, pp. 1121-1131, vol. 14.

Michael Pacher et al., Two Unlinked Double-Strand Breaks Can Induce Reciprocal Exchanges in Plant Genomes via Homologous Recombination and Nonhomologous End Joining, Genetics, 2007, pp. 21-29, vol. 175.

International Search Report—PCT/US2015/066195—dated Apr. 18, 2016.

* cited by examiner

SEQUENCE LISTING

<160> NUMBER OF SEQ ID NOS: 41

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

-continued

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
```

-continued

```
        785                 790                 795                 800
Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200
```

```
Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 1388
<212> TYPE: PRT
<213> ORGANISM: Streptococcus thermophilus

<400> SEQUENCE: 2

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
```

```
            195                 200                 205
Glu Glu Ile Val Lys Asp Lys Ile Ser Lys Leu Glu Lys Lys Asp Arg
210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Tyr Ser Asp
        275                 280                 285

Val Phe Leu Lys Ala Lys Lys Leu Tyr Asp Ala Ile Leu Leu Ser Gly
        290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
                340                 345                 350

Asp Asp Thr Lys Asn Gly Tyr Ala Gly Tyr Ile Asp Gly Lys Thr Asn
            355                 360                 365

Gln Glu Asp Phe Tyr Val Tyr Leu Lys Lys Leu Leu Ala Glu Phe Glu
        370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
                420                 425                 430

Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
        450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
        515                 520                 525

Phe Ile Ala Glu Ser Met Arg Asp Tyr Gln Phe Leu Asp Ser Lys Gln
530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
            565                 570                 575

Ile Glu Leu Lys Gly Ile Glu Lys Gln Phe Asn Ser Ser Leu Ser Thr
        580                 585                 590

Tyr His Asp Leu Leu Asn Ile Ile Asn Asp Lys Glu Phe Leu Asp Asp
        595                 600                 605

Ser Ser Asn Glu Ala Ile Ile Glu Glu Ile Ile His Thr Leu Thr Ile
610                 615                 620
```

-continued

Phe Glu Asp Arg Glu Met Ile Lys Gln Arg Leu Ser Lys Phe Glu Asn
625                 630                 635                 640

Ile Phe Asp Lys Ser Val Leu Lys Leu Ser Arg His Tyr Thr
            645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Gly Ile Ser
        675                 680                 685

Asn Arg Asn Phe Met Gln Leu Ile His Asp Asp Ala Leu Ser Phe Lys
        690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
                725                 730                 735

Gly Ile Leu Gln Ser Ile Lys Ile Val Asp Glu Leu Val Lys Val Met
            740                 745                 750

Gly Gly Arg Lys Pro Glu Ser Ile Val Val Glu Met Ala Arg Glu Asn
            755                 760                 765

Gln Tyr Thr Asn Gln Gly Lys Ser Asn Ser Gln Arg Leu Lys Arg
770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
            805                 810                 815

Arg Leu Tyr Leu Tyr Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
            835                 840                 845

Ile Pro Gln Ala Phe Leu Lys Asp Asn Ser Ile Asp Asn Lys Val Leu
            850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
            900                 905                 910

Gly Gly Leu Ser Pro Glu Asp Lys Ala Gly Phe Ile Gln Arg Gln Leu
            915                 920                 925

Val Glu Thr Arg Gln Ile Thr Lys His Val Ala Arg Leu Leu Asp Glu
            930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
            980                 985                 990

Asp Ala Tyr Leu Asn Ala Val Val Ala Ser Ala Leu Leu Lys Lys Tyr
            995                 1000                1005

Pro Lys Leu Glu Pro Glu Phe Val Tyr Gly Asp Tyr Pro Lys Tyr
    1010                1015                1020

Asn Ser Phe Arg Glu Arg Lys Ser Ala Thr Glu Lys Val Tyr Phe
    1025                1030                1035

```
Tyr Ser Asn Ile Met Asn Ile Phe Lys Lys Ser Ile Ser Leu Ala
    1040                1045                1050

Asp Gly Arg Val Ile Glu Arg Pro Leu Ile Glu Val Asn Glu Glu
    1055                1060                1065

Thr Gly Glu Ser Val Trp Asn Lys Glu Ser Asp Leu Ala Thr Val
    1070                1075                1080

Arg Arg Val Leu Ser Tyr Pro Gln Val Asn Val Lys Lys Val
    1085                1090                1095

Glu Glu Gln Asn His Gly Leu Asp Arg Gly Lys Pro Lys Gly Leu
    1100                1105                1110

Phe Asn Ala Asn Leu Ser Ser Lys Pro Lys Pro Asn Ser Asn Glu
    1115                1120                1125

Asn Leu Val Gly Ala Lys Glu Tyr Leu Asp Pro Lys Lys Tyr Gly
    1130                1135                1140

Gly Tyr Ala Gly Ile Ser Asn Ser Phe Thr Val Leu Val Lys Gly
    1145                1150                1155

Thr Ile Glu Lys Gly Ala Lys Lys Ile Thr Asn Val Leu Glu
    1160                1165                1170

Phe Gln Gly Ile Ser Ile Leu Asp Arg Ile Asn Tyr Arg Lys Asp
    1175                1180                1185

Lys Leu Asn Phe Leu Leu Glu Lys Gly Tyr Lys Asp Ile Glu Leu
    1190                1195                1200

Ile Ile Glu Leu Pro Lys Tyr Ser Leu Phe Glu Leu Ser Asp Gly
    1205                1210                1215

Ser Arg Arg Met Leu Ala Ser Ile Leu Ser Thr Asn Asn Lys Arg
    1220                1225                1230

Gly Glu Ile His Lys Gly Asn Gln Ile Phe Leu Ser Gln Lys Phe
    1235                1240                1245

Val Lys Leu Leu Tyr His Ala Lys Arg Ile Ser Asn Thr Ile Asn
    1250                1255                1260

Glu Asn His Arg Lys Tyr Val Glu Asn His Lys Lys Glu Phe Glu
    1265                1270                1275

Glu Leu Phe Tyr Tyr Ile Leu Glu Phe Asn Glu Asn Tyr Val Gly
    1280                1285                1290

Ala Lys Lys Asn Gly Lys Leu Leu Asn Ser Ala Phe Gln Ser Trp
    1295                1300                1305

Gln Asn His Ser Ile Asp Glu Leu Cys Ser Ser Phe Ile Gly Pro
    1310                1315                1320

Thr Gly Ser Glu Arg Lys Gly Leu Phe Glu Leu Thr Ser Arg Gly
    1325                1330                1335

Ser Ala Ala Asp Phe Glu Phe Leu Gly Val Lys Ile Pro Arg Tyr
    1340                1345                1350

Arg Asp Tyr Thr Pro Ser Ser Leu Leu Lys Asp Ala Thr Leu Ile
    1355                1360                1365

His Gln Ser Val Thr Gly Leu Tyr Glu Thr Arg Ile Asp Leu Ala
    1370                1375                1380

Lys Leu Gly Glu Gly
    1385

<210> SEQ ID NO 3
<211> LENGTH: 1345
<212> TYPE: PRT
<213> ORGANISM: Streptococcus mutans

<400> SEQUENCE: 3
```

-continued

```
Met Lys Lys Pro Tyr Ser Ile Gly Leu Asp Ile Gly Thr Asn Ser Val
 1               5                  10                  15
Gly Trp Ala Val Val Thr Asp Asp Tyr Lys Val Pro Ala Lys Lys Met
             20                  25                  30
Lys Val Leu Gly Asn Thr Asp Lys Ser His Ile Glu Lys Asn Leu Leu
             35                  40                  45
Gly Ala Leu Leu Phe Asp Ser Gly Asn Thr Ala Glu Asp Arg Arg Leu
 50                  55                  60
Lys Arg Thr Ala Arg Arg Tyr Thr Arg Arg Asn Arg Ile Leu
 65              70                  75                  80
Tyr Leu Gln Glu Ile Phe Ser Glu Glu Met Gly Lys Val Asp Asp Ser
                 85                  90                  95
Phe Phe His Arg Leu Glu Asp Ser Phe Leu Val Thr Glu Asp Lys Arg
                100                 105                 110
Gly Glu Arg His Pro Ile Phe Gly Asn Leu Glu Glu Val Lys Tyr
            115                 120                 125
His Glu Asn Phe Pro Thr Ile Tyr His Leu Arg Gln Tyr Leu Ala Asp
        130                 135                 140
Asn Pro Glu Lys Val Asp Leu Arg Leu Val Tyr Leu Ala Leu Ala His
145                 150                 155                 160
Ile Ile Lys Phe Arg Gly His Phe Leu Ile Glu Gly Lys Phe Asp Thr
                165                 170                 175
Arg Asn Asn Asp Val Gln Arg Leu Phe Gln Glu Phe Leu Ala Val Tyr
            180                 185                 190
Asp Asn Thr Phe Glu Asn Ser Ser Leu Gln Glu Gln Asn Val Gln Val
        195                 200                 205
Glu Glu Ile Leu Thr Asp Lys Ile Ser Lys Ser Ala Lys Lys Asp Arg
210                 215                 220
Val Leu Lys Leu Phe Pro Asn Glu Lys Ser Asn Gly Arg Phe Ala Glu
225                 230                 235                 240
Phe Leu Lys Leu Ile Val Gly Asn Gln Ala Asp Phe Lys Lys His Phe
                245                 250                 255
Glu Leu Glu Glu Lys Ala Pro Leu Gln Phe Ser Lys Asp Thr Tyr Glu
            260                 265                 270
Glu Glu Leu Glu Val Leu Leu Ala Gln Ile Gly Asp Asn Tyr Ala Glu
        275                 280                 285
Leu Phe Leu Ser Ala Lys Lys Leu Tyr Asp Ser Ile Leu Leu Ser Gly
290                 295                 300
Ile Leu Thr Val Thr Asp Val Gly Thr Lys Ala Pro Leu Ser Ala Ser
305                 310                 315                 320
Met Ile Gln Arg Tyr Asn Glu His Gln Met Asp Leu Ala Gln Leu Lys
                325                 330                 335
Gln Phe Ile Arg Gln Lys Leu Ser Asp Lys Tyr Asn Glu Val Phe Ser
            340                 345                 350
Asp Val Ser Lys Asp Gly Tyr Ala Gly Tyr Ile Asp Gly Lys Thr Asn
        355                 360                 365
Gln Glu Ala Phe Tyr Lys Tyr Leu Lys Gly Leu Leu Asn Lys Ile Glu
370                 375                 380
Gly Ser Gly Tyr Phe Leu Asp Lys Ile Glu Arg Glu Asp Phe Leu Arg
385                 390                 395                 400
Lys Gln Arg Thr Phe Asp Asn Gly Ser Ile Pro His Gln Ile His Leu
                405                 410                 415
```

-continued

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
            435                 440                 445

Pro Tyr Tyr Val Gly Pro Leu Ala Arg Gly Lys Ser Asp Phe Ala Trp
            450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
                485                 490                 495

Asn Tyr Asp Leu Tyr Leu Pro Asn Gln Lys Val Leu Pro Lys His Ser
            500                 505                 510

Leu Leu Tyr Glu Lys Phe Thr Val Tyr Asn Glu Leu Thr Lys Val Lys
            515                 520                 525

Tyr Lys Thr Glu Gln Gly Lys Thr Ala Phe Phe Asp Ala Asn Met Lys
            530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
                565                 570                 575

Val Asp Leu Thr Gly Leu Asp Lys Glu Asn Lys Val Phe Asn Ala Ser
            580                 585                 590

Tyr Gly Thr Tyr His Asp Leu Cys Lys Ile Leu Asp Lys Asp Phe Leu
            595                 600                 605

Asp Asn Ser Lys Asn Glu Lys Ile Leu Glu Asp Ile Val Leu Thr Leu
            610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                645                 650                 655

Tyr Thr Gly Trp Gly Arg Leu Ser Ala Glu Leu Ile His Gly Ile Arg
            660                 665                 670

Asn Lys Glu Ser Arg Lys Thr Ile Leu Asp Tyr Leu Ile Asp Asp Gly
            675                 680                 685

Asn Ser Asn Arg Asn Phe Met Gln Leu Ile Asn Asp Asp Ala Leu Ser
            690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
                725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
            755                 760                 765

Phe Thr Asn Gln Gly Arg Arg Asn Ser Gln Gln Arg Leu Lys Gly Leu
            770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
                805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys

```
                    835              840              845
Asp Asn Ser Ile Asp Asn Arg Val Leu Thr Ser Ser Lys Glu Asn Arg
            850              855              860

Gly Lys Ser Asp Asp Val Pro Ser Lys Asp Val Val Arg Lys Met Lys
865              870              875              880

Ser Tyr Trp Ser Lys Leu Leu Ser Ala Lys Leu Ile Thr Gln Arg Lys
                885              890              895

Phe Asp Asn Leu Thr Lys Ala Glu Arg Gly Gly Leu Thr Asp Asp Asp
            900              905              910

Lys Ala Gly Phe Ile Lys Arg Gln Leu Val Glu Thr Arg Gln Ile Thr
            915              920              925

Lys His Val Ala Arg Ile Leu Asp Glu Arg Phe Asn Thr Glu Thr Asp
930              935              940

Glu Asn Asn Lys Lys Ile Arg Gln Val Lys Ile Val Thr Leu Lys Ser
945              950              955              960

Asn Leu Val Ser Asn Phe Arg Lys Glu Phe Glu Leu Tyr Lys Val Arg
                965              970              975

Glu Ile Asn Asp Tyr His His Ala His Asp Ala Tyr Leu Asn Ala Val
            980              985              990

Ile Gly Lys Ala Leu Leu Gly Val Tyr Pro Gln Leu Glu Pro Glu Phe
            995              1000             1005

Val Tyr Gly Asp Tyr Pro His Phe His Gly His Lys Glu Asn Lys
    1010             1015             1020

Ala Thr Ala Lys Lys Phe Phe Tyr Ser Asn Ile Met Asn Phe Phe
    1025             1030             1035

Lys Lys Asp Asp Val Arg Thr Asp Lys Asn Gly Glu Ile Ile Trp
    1040             1045             1050

Lys Lys Asp Glu His Ile Ser Asn Ile Lys Lys Val Leu Ser Tyr
    1055             1060             1065

Pro Gln Val Asn Ile Val Lys Lys Val Glu Glu Gln Thr Gly Gly
    1070             1075             1080

Phe Ser Lys Glu Ser Ile Leu Pro Lys Gly Asn Ser Asp Lys Leu
    1085             1090             1095

Ile Pro Arg Lys Thr Lys Lys Phe Tyr Trp Asp Thr Lys Lys Tyr
    1100             1105             1110

Gly Gly Phe Asp Ser Pro Ile Val Ala Tyr Ser Ile Leu Val Ile
    1115             1120             1125

Ala Asp Ile Glu Lys Gly Lys Ser Lys Lys Leu Lys Thr Val Lys
    1130             1135             1140

Ala Leu Val Gly Val Thr Ile Met Glu Lys Met Thr Phe Glu Arg
    1145             1150             1155

Asp Pro Val Ala Phe Leu Glu Arg Lys Gly Tyr Arg Asn Val Gln
    1160             1165             1170

Glu Glu Asn Ile Ile Lys Leu Pro Lys Tyr Ser Leu Phe Lys Leu
    1175             1180             1185

Glu Asn Gly Arg Lys Arg Leu Leu Ala Ser Ala Arg Glu Leu Gln
    1190             1195             1200

Lys Gly Asn Glu Ile Val Leu Pro Asn His Leu Gly Thr Leu Leu
    1205             1210             1215

Tyr His Ala Lys Asn Ile His Lys Val Asp Glu Pro Lys His Leu
    1220             1225             1230

Asp Tyr Val Asp Lys His Lys Asp Glu Phe Lys Glu Leu Leu Asp
    1235             1240             1245
```

```
Val Val Ser Asn Phe Ser Lys Lys Tyr Thr Leu Ala Glu Gly Asn
    1250                1255                1260

Leu Glu Lys Ile Lys Glu Leu Tyr Ala Gln Asn Asn Gly Glu Asp
    1265                1270                1275

Leu Lys Glu Leu Ala Ser Ser Phe Ile Asn Leu Leu Thr Phe Thr
    1280                1285                1290

Ala Ile Gly Ala Pro Ala Thr Phe Lys Phe Phe Asp Lys Asn Ile
    1295                1300                1305

Asp Arg Lys Arg Tyr Thr Ser Thr Thr Glu Ile Leu Asn Ala Thr
    1310                1315                1320

Leu Ile His Gln Ser Ile Thr Gly Leu Tyr Glu Thr Arg Ile Asp
    1325                1330                1335

Leu Asn Lys Leu Gly Gly Asp
    1340                1345
```

<210> SEQ ID NO 4
<211> LENGTH: 984
<212> TYPE: PRT
<213> ORGANISM: Campylobacter jejuni

<400> SEQUENCE: 4

```
Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
                20                  25                  30

Thr Lys Val Glu Asn Pro Lys Thr Gly Glu Ser Leu Ala Leu Pro Arg
            35                  40                  45

Arg Leu Ala Arg Ser Ala Arg Lys Arg Leu Ala Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
    210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
```

```
                260                 265                 270
Asn Leu Leu Asn Asn Leu Lys Asn Thr Glu Gly Ile Leu Tyr Thr Lys
            275                 280                 285

Asp Asp Leu Asn Ala Leu Leu Asn Glu Val Leu Lys Asn Gly Thr Leu
290                 295                 300

Thr Tyr Lys Gln Thr Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Leu
                340                 345                 350

Asn Glu Ile Ala Lys Asp Ile Thr Leu Ile Lys Asp Glu Ile Lys Leu
            355                 360                 365

Lys Lys Ala Leu Ala Lys Tyr Asp Leu Asn Gln Asn Gln Ile Asp Ser
            370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
            435                 440                 445

Asn Pro Val Val Leu Arg Ala Ile Lys Glu Tyr Arg Lys Val Leu Asn
450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
            515                 520                 525

Leu Phe Lys Glu Gln Lys Glu Phe Cys Ala Tyr Ser Gly Glu Lys Ile
            530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
            595                 600                 605

Lys Asn Leu Pro Thr Lys Gln Lys Arg Ile Leu Asp Lys Asn Tyr
            610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
            675                 680                 685
```

```
Ala Leu Arg His Thr Trp Gly Phe Ser Ala Lys Asp Arg Asn Asn His
        690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
                740                 745                 750

Arg Lys Phe Phe Glu Pro Phe Ser Gly Phe Arg Gln Lys Val Leu Asp
            755                 760                 765

Lys Ile Asp Glu Ile Phe Val Ser Lys Pro Glu Arg Lys Lys Pro Ser
        770                 775                 780

Gly Ala Leu His Glu Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
    850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
        915                 920                 925

Glu Thr Leu Ser Lys Asn Gln Lys Ile Leu Phe Lys Asn Ala Asn Glu
    930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980

<210> SEQ ID NO 5
<211> LENGTH: 1082
<212> TYPE: PRT
<213> ORGANISM: Neisseria meningitides

<400> SEQUENCE: 5

Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
```

```
            65                  70                  75                  80
Arg Thr Arg Arg Leu Leu Lys Arg Glu Gly Val Leu Gln Ala Ala Asn
                    85                  90                  95

Phe Asp Glu Asn Gly Leu Ile Lys Ser Leu Pro Asn Thr Pro Trp Gln
                100                 105                 110

Leu Arg Ala Ala Ala Leu Asp Arg Lys Leu Thr Pro Leu Glu Trp Ser
                115                 120                 125

Ala Val Leu Leu His Leu Ile Lys His Arg Gly Tyr Leu Ser Gln Arg
            130                 135                 140

Lys Asn Glu Gly Glu Thr Ala Asp Lys Glu Leu Gly Ala Leu Leu Lys
145                 150                 155                 160

Gly Val Ala Gly Asn Ala His Ala Leu Gln Thr Gly Asp Phe Arg Thr
                    165                 170                 175

Pro Ala Glu Leu Ala Leu Asn Lys Phe Glu Lys Glu Ser Gly His Ile
                180                 185                 190

Arg Asn Gln Arg Ser Asp Tyr Ser His Thr Phe Ser Arg Lys Asp Leu
                195                 200                 205

Gln Ala Glu Leu Ile Leu Leu Phe Glu Lys Gln Lys Glu Phe Gly Asn
            210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                    245                 250                 255

His Cys Thr Phe Glu Pro Ala Glu Pro Lys Ala Ala Lys Asn Thr Tyr
                260                 265                 270

Thr Ala Glu Arg Phe Ile Trp Leu Thr Lys Leu Asn Asn Leu Arg Ile
                275                 280                 285

Leu Glu Gln Gly Ser Glu Arg Pro Leu Thr Asp Thr Glu Arg Ala Thr
            290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                    325                 330                 335

Tyr Gly Lys Asp Asn Ala Glu Ala Ser Thr Leu Met Glu Met Lys Ala
                340                 345                 350

Tyr His Ala Ile Ser Arg Ala Leu Glu Lys Glu Gly Leu Lys Asp Lys
                355                 360                 365

Lys Ser Pro Leu Asn Leu Ser Pro Glu Leu Gln Asp Glu Ile Gly Thr
            370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                    405                 410                 415

Phe Asp Lys Phe Val Gln Ile Ser Leu Lys Ala Leu Arg Arg Ile Val
                420                 425                 430

Pro Leu Met Glu Gln Gly Lys Arg Tyr Asp Glu Ala Cys Ala Glu Ile
                435                 440                 445

Tyr Gly Asp His Tyr Gly Lys Lys Asn Thr Glu Glu Lys Ile Tyr Leu
            450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                    485                 490                 495
```

```
Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
            515                 520                 525

Asp Arg Glu Lys Ala Ala Lys Phe Arg Glu Tyr Phe Pro Asn Phe
            530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
            595                 600                 605

Ser Glu Asn Gln Asn Lys Gly Asn Gln Thr Pro Tyr Glu Tyr Phe Asn
            610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
            675                 680                 685

Gly Lys Gly Lys Lys Arg Val Phe Ala Ser Asn Gly Gln Ile Thr Asn
690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Val Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
            755                 760                 765

Lys Thr His Phe Pro Gln Pro Trp Glu Phe Phe Ala Gln Glu Val Met
            770                 775                 780

Ile Arg Val Phe Gly Lys Pro Asp Gly Lys Pro Glu Phe Glu Glu Ala
785                 790                 795                 800

Asp Thr Leu Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
            835                 840                 845

Ser Ala Lys Arg Leu Asp Glu Gly Val Ser Val Leu Arg Val Pro Leu
            850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910
```

```
Ala Gly Asn Arg Thr Gln Gln Val Lys Ala Val Arg Val Glu Gln Val
            915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Asp Trp Gln Leu Ile Asp
                980                 985                 990

Asp Ser Phe Asn Phe Lys Phe Ser Leu His Pro Asn Asp Leu Val Glu
            995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Val Arg
    1070                1075                1080

<210> SEQ ID NO 6
<211> LENGTH: 1629
<212> TYPE: PRT
<213> ORGANISM: Francisella tularensis

<400> SEQUENCE: 6

Met Asn Phe Lys Ile Leu Pro Ile Ala Ile Asp Leu Gly Val Lys Asn
1               5                   10                  15

Thr Gly Val Phe Ser Ala Phe Tyr Gln Lys Gly Thr Ser Leu Glu Arg
            20                  25                  30

Leu Asp Asn Lys Asn Gly Lys Val Tyr Glu Leu Ser Lys Asp Ser Tyr
        35                  40                  45

Thr Leu Leu Met Asn Asn Arg Thr Ala Arg Arg His Gln Arg Arg Gly
    50                  55                  60

Ile Asp Arg Lys Gln Leu Val Lys Arg Leu Phe Lys Leu Ile Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
            100                 105                 110

Pro Glu Tyr Leu Asn Ile Val Pro Glu Gln Val Lys Ala Ile Leu Met
        115                 120                 125

Asp Ile Phe Asp Asp Tyr Asn Gly Glu Asp Asp Leu Asp Ser Tyr Leu
    130                 135                 140

Lys Leu Ala Thr Glu Gln Glu Ser Lys Ile Ser Glu Ile Tyr Asn Lys
145                 150                 155                 160

Leu Met Gln Lys Ile Leu Glu Phe Lys Leu Met Lys Leu Cys Thr Asp
                165                 170                 175

Ile Lys Asp Asp Lys Val Ser Thr Lys Thr Leu Lys Glu Ile Thr Ser
            180                 185                 190

Tyr Glu Phe Glu Leu Leu Ala Asp Tyr Leu Ala Asn Tyr Ser Glu Ser
        195                 200                 205
```

```
Leu Lys Thr Gln Lys Phe Ser Tyr Thr Asp Lys Gln Gly Asn Leu Lys
    210                 215                 220

Glu Leu Ser Tyr Tyr His His Asp Lys Tyr Asn Ile Gln Glu Phe Leu
225                 230                 235                 240

Lys Arg His Ala Thr Ile Asn Asp Arg Ile Leu Asp Thr Leu Leu Thr
                245                 250                 255

Asp Asp Leu Asp Ile Trp Asn Phe Asn Phe Glu Lys Phe Asp Phe Asp
            260                 265                 270

Lys Asn Glu Glu Lys Leu Gln Asn Gln Glu Asp Lys Asp His Ile Gln
        275                 280                 285

Ala His Leu His His Phe Val Phe Ala Val Asn Lys Ile Lys Ser Glu
    290                 295                 300

Met Ala Ser Gly Gly Arg His Arg Ser Gln Tyr Phe Gln Glu Ile Thr
305                 310                 315                 320

Asn Val Leu Asp Glu Asn Asn His Gln Glu Gly Tyr Leu Lys Asn Phe
                325                 330                 335

Cys Glu Asn Leu His Asn Lys Lys Tyr Ser Asn Leu Ser Val Lys Asn
            340                 345                 350

Leu Val Asn Leu Ile Gly Asn Leu Ser Asn Leu Glu Leu Lys Pro Leu
        355                 360                 365

Arg Lys Tyr Phe Asn Asp Lys Ile His Ala Lys Ala Asp His Trp Asp
    370                 375                 380

Glu Gln Lys Phe Thr Glu Thr Tyr Cys His Trp Ile Leu Gly Glu Trp
385                 390                 395                 400

Arg Val Gly Val Lys Asp Gln Asp Lys Lys Asp Gly Ala Lys Tyr Ser
                405                 410                 415

Tyr Lys Asp Leu Cys Asn Glu Leu Lys Gln Lys Val Thr Lys Ala Gly
            420                 425                 430

Leu Val Asp Phe Leu Leu Glu Leu Asp Pro Cys Arg Thr Ile Pro Pro
        435                 440                 445

Tyr Leu Asp Asn Asn Asn Arg Lys Pro Pro Lys Cys Gln Ser Leu Ile
    450                 455                 460

Leu Asn Pro Lys Phe Leu Asp Asn Gln Tyr Pro Asn Trp Gln Gln Tyr
465                 470                 475                 480

Leu Gln Glu Leu Lys Lys Leu Gln Ser Ile Gln Asn Tyr Leu Asp Ser
                485                 490                 495

Phe Glu Thr Asp Leu Lys Val Leu Lys Ser Ser Lys Asp Gln Pro Tyr
            500                 505                 510

Phe Val Glu Tyr Lys Ser Ser Asn Gln Gln Ile Ala Ser Gly Gln Arg
        515                 520                 525

Asp Tyr Lys Asp Leu Asp Ala Arg Ile Leu Gln Phe Ile Phe Asp Arg
    530                 535                 540

Val Lys Ala Ser Asp Glu Leu Leu Asn Glu Ile Tyr Phe Gln Ala
545                 550                 555                 560

Lys Lys Leu Lys Gln Lys Ala Ser Ser Glu Leu Lys Leu Glu Ser
                565                 570                 575

Ser Lys Lys Leu Asp Glu Val Ile Ala Asn Ser Gln Leu Ser Gln Ile
            580                 585                 590

Leu Lys Ser Gln His Thr Asn Gly Ile Phe Glu Gln Gly Thr Phe Leu
        595                 600                 605

His Leu Val Cys Lys Tyr Tyr Lys Gln Arg Gln Arg Ala Arg Asp Ser
    610                 615                 620
```

```
Arg Leu Tyr Ile Met Pro Glu Tyr Arg Tyr Asp Lys Lys Leu His Lys
625                 630                 635                 640

Tyr Asn Asn Thr Gly Arg Phe Asp Asp Asn Gln Leu Leu Thr Tyr
            645                 650                 655

Cys Asn His Lys Pro Arg Gln Lys Arg Tyr Gln Leu Leu Asn Asp Leu
            660                 665                 670

Ala Gly Val Leu Gln Val Ser Pro Asn Phe Leu Lys Asp Lys Ile Gly
            675                 680                 685

Ser Asp Asp Asp Leu Phe Ile Ser Lys Trp Leu Val Glu His Ile Arg
690                 695                 700

Gly Phe Lys Lys Ala Cys Glu Asp Ser Leu Lys Ile Gln Lys Asp Asn
705                 710                 715                 720

Arg Gly Leu Leu Asn His Lys Ile Asn Ile Ala Arg Asn Thr Lys Gly
                725                 730                 735

Lys Cys Glu Lys Glu Ile Phe Asn Leu Ile Cys Lys Ile Glu Gly Ser
                740                 745                 750

Glu Asp Lys Lys Gly Asn Tyr Lys His Gly Leu Ala Tyr Glu Leu Gly
                755                 760                 765

Val Leu Leu Phe Gly Glu Pro Asn Glu Ala Ser Lys Pro Glu Phe Asp
770                 775                 780

Arg Lys Ile Lys Lys Phe Asn Ser Ile Tyr Ser Phe Ala Gln Ile Gln
785                 790                 795                 800

Gln Ile Ala Phe Ala Glu Arg Lys Gly Asn Ala Asn Thr Cys Ala Val
                805                 810                 815

Cys Ser Ala Asp Asn Ala His Arg Met Gln Gln Ile Lys Ile Thr Glu
                820                 825                 830

Pro Val Glu Asp Asn Lys Asp Lys Ile Ile Leu Ser Ala Lys Ala Gln
                835                 840                 845

Arg Leu Pro Ala Ile Pro Thr Arg Ile Val Asp Gly Ala Val Lys Lys
                850                 855                 860

Met Ala Thr Ile Leu Ala Lys Asn Ile Val Asp Asp Asn Trp Gln Asn
865                 870                 875                 880

Ile Lys Gln Val Leu Ser Ala Lys His Gln Leu His Ile Pro Ile Ile
                885                 890                 895

Thr Glu Ser Asn Ala Phe Glu Phe Glu Pro Ala Leu Ala Asp Val Lys
                900                 905                 910

Gly Lys Ser Leu Lys Asp Arg Lys Lys Ala Leu Glu Arg Ile Ser
                915                 920                 925

Pro Glu Asn Ile Phe Lys Asp Lys Asn Asn Arg Ile Lys Glu Phe Ala
                930                 935                 940

Lys Gly Ile Ser Ala Tyr Ser Gly Ala Asn Leu Thr Asp Gly Asp Phe
945                 950                 955                 960

Asp Gly Ala Lys Glu Glu Leu Asp His Ile Ile Pro Arg Ser His Lys
                965                 970                 975

Lys Tyr Gly Thr Leu Asn Asp Glu Ala Asn Leu Ile Cys Val Thr Arg
                980                 985                 990

Gly Asp Asn Lys Asn Lys Gly Asn Arg Ile Phe Cys Leu Arg Asp Leu
                995                 1000                1005

Ala Asp Asn Tyr Lys Leu Lys Gln Phe Glu Thr Thr Asp Asp Leu
    1010                1015                1020

Glu Ile Glu Lys Lys Ile Ala Asp Thr Ile Trp Asp Ala Asn Lys
    1025                1030                1035

Lys Asp Phe Lys Phe Gly Asn Tyr Arg Ser Phe Ile Asn Leu Thr
```

```
                1040                1045                1050
Pro Gln Glu Gln Lys Ala Phe Arg His Ala Leu Phe Leu Ala Asp
        1055                1060                1065
Glu Asn Pro Ile Lys Gln Ala Val Ile Arg Ala Ile Asn Asn Arg
        1070                1075                1080
Asn Arg Thr Phe Val Asn Gly Thr Gln Arg Tyr Phe Ala Glu Val
        1085                1090                1095
Leu Ala Asn Asn Ile Tyr Leu Arg Ala Lys Lys Glu Asn Leu Asn
        1100                1105                1110
Thr Asp Lys Ile Ser Phe Asp Tyr Phe Gly Ile Pro Thr Ile Gly
        1115                1120                1125
Asn Gly Arg Gly Ile Ala Glu Ile Arg Gln Leu Tyr Glu Lys Val
        1130                1135                1140
Asp Ser Asp Ile Gln Ala Tyr Ala Lys Gly Asp Lys Pro Gln Ala
        1145                1150                1155
Ser Tyr Ser His Leu Ile Asp Ala Met Leu Ala Phe Cys Ile Ala
        1160                1165                1170
Ala Asp Glu His Arg Asn Asp Gly Ser Ile Gly Leu Glu Ile Asp
        1175                1180                1185
Lys Asn Tyr Ser Leu Tyr Pro Leu Asp Lys Asn Thr Gly Glu Val
        1190                1195                1200
Phe Thr Lys Asp Ile Phe Ser Gln Ile Lys Ile Thr Asp Asn Glu
        1205                1210                1215
Phe Ser Asp Lys Lys Leu Val Arg Lys Lys Ala Ile Glu Gly Phe
        1220                1225                1230
Asn Thr His Arg Gln Met Thr Arg Asp Gly Ile Tyr Ala Glu Asn
        1235                1240                1245
Tyr Leu Pro Ile Leu Ile His Lys Glu Leu Asn Glu Val Arg Lys
        1250                1255                1260
Gly Tyr Thr Trp Lys Asn Ser Glu Glu Ile Lys Ile Phe Lys Gly
        1265                1270                1275
Lys Lys Tyr Asp Ile Gln Gln Leu Asn Asn Leu Val Tyr Cys Leu
        1280                1285                1290
Lys Phe Val Asp Lys Pro Ile Ser Ile Asp Ile Gln Ile Ser Thr
        1295                1300                1305
Leu Glu Glu Leu Arg Asn Ile Leu Thr Thr Asn Asn Ile Ala Ala
        1310                1315                1320
Thr Ala Glu Tyr Tyr Ile Asn Leu Lys Thr Gln Lys Leu His
        1325                1330                1335
Glu Tyr Tyr Ile Glu Asn Tyr Asn Thr Ala Leu Gly Tyr Lys Lys
        1340                1345                1350
Tyr Ser Lys Glu Met Glu Phe Leu Arg Ser Leu Ala Tyr Arg Ser
        1355                1360                1365
Glu Arg Val Lys Ile Lys Ser Ile Asp Asp Val Lys Gln Val Leu
        1370                1375                1380
Asp Lys Asp Ser Asn Phe Ile Ile Gly Lys Ile Thr Leu Pro Phe
        1385                1390                1395
Lys Lys Glu Trp Gln Arg Leu Tyr Arg Glu Trp Gln Asn Thr Thr
        1400                1405                1410
Ile Lys Asp Asp Tyr Glu Phe Leu Lys Ser Phe Phe Asn Val Lys
        1415                1420                1425
Ser Ile Thr Lys Leu His Lys Lys Val Arg Lys Asp Phe Ser Leu
        1430                1435                1440
```

Pro Ile Ser Thr Asn Glu Gly Lys Phe Leu Val Lys Arg Lys Thr
    1445                1450                1455

Trp Asp Asn Asn Phe Ile Tyr Gln Ile Leu Asn Asp Ser Asp Ser
    1460                1465                1470

Arg Ala Asp Gly Thr Lys Pro Phe Ile Pro Ala Phe Asp Ile Ser
    1475                1480                1485

Lys Asn Glu Ile Val Glu Ala Ile Ile Asp Ser Phe Thr Ser Lys
    1490                1495                1500

Asn Ile Phe Trp Leu Pro Lys Asn Ile Glu Leu Gln Lys Val Asp
    1505                1510                1515

Asn Lys Asn Ile Phe Ala Ile Asp Thr Ser Lys Trp Phe Glu Val
    1520                1525                1530

Glu Thr Pro Ser Asp Leu Arg Asp Ile Gly Ile Ala Thr Ile Gln
    1535                1540                1545

Tyr Lys Ile Asp Asn Asn Ser Arg Pro Lys Val Arg Val Lys Leu
    1550                1555                1560

Asp Tyr Val Ile Asp Asp Ser Lys Ile Asn Tyr Phe Met Asn
    1565                1570                1575

His Ser Leu Leu Lys Ser Arg Tyr Pro Asp Lys Val Leu Glu Ile
    1580                1585                1590

Leu Lys Gln Ser Thr Ile Ile Glu Phe Glu Ser Ser Gly Phe Asn
    1595                1600                1605

Lys Thr Ile Lys Glu Met Leu Gly Met Lys Leu Ala Gly Ile Tyr
    1610                1615                1620

Asn Glu Thr Ser Asn Asn
    1625

<210> SEQ ID NO 7
<211> LENGTH: 1056
<212> TYPE: PRT
<213> ORGANISM: Pasteurella multocida

<400> SEQUENCE: 7

Met Gln Thr Thr Asn Leu Ser Tyr Ile Leu Gly Leu Asp Leu Gly Ile
1               5                   10                  15

Ala Ser Val Gly Trp Ala Val Val Glu Ile Asn Glu Asn Glu Asp Pro
            20                  25                  30

Ile Gly Leu Ile Asp Val Gly Val Arg Ile Phe Glu Arg Ala Glu Val
            35                  40                  45

Pro Lys Thr Gly Glu Ser Leu Ala Leu Ser Arg Arg Leu Ala Arg Ser
    50                  55                  60

Thr Arg Arg Leu Ile Arg Arg Arg Ala His Arg Leu Leu Leu Ala Lys
65                  70                  75                  80

Arg Phe Leu Lys Arg Glu Gly Ile Leu Ser Thr Ile Asp Leu Glu Lys
                85                  90                  95

Gly Leu Pro Asn Gln Ala Trp Glu Leu Arg Val Ala Gly Leu Glu Arg
            100                 105                 110

Arg Leu Ser Ala Ile Glu Trp Gly Ala Val Leu Leu His Leu Ile Lys
            115                 120                 125

His Arg Gly Tyr Leu Ser Lys Arg Lys Asn Glu Ser Gln Thr Asn Asn
        130                 135                 140

Lys Glu Leu Gly Ala Leu Leu Ser Gly Val Ala Gln Asn His Gln Leu
145                 150                 155                 160

Leu Gln Ser Asp Asp Tyr Arg Thr Pro Ala Glu Leu Ala Leu Lys Lys

```
                    165                 170                 175
Phe Ala Lys Glu Glu Gly His Ile Arg Asn Gln Arg Gly Ala Tyr Thr
                180                 185                 190
His Thr Phe Asn Arg Leu Asp Leu Leu Ala Glu Leu Asn Leu Leu Phe
            195                 200                 205
Ala Gln Gln His Gln Phe Gly Asn Pro His Cys Lys Glu His Ile Gln
        210                 215                 220
Gln Tyr Met Thr Glu Leu Leu Met Trp Gln Lys Pro Ala Leu Ser Gly
225                 230                 235                 240
Glu Ala Ile Leu Lys Met Leu Gly Lys Cys Thr His Glu Lys Asn Glu
                245                 250                 255
Phe Lys Ala Ala Lys His Thr Tyr Ser Ala Glu Arg Phe Val Trp Leu
            260                 265                 270
Thr Lys Leu Asn Asn Leu Arg Ile Leu Glu Asp Gly Ala Glu Arg Ala
        275                 280                 285
Leu Asn Glu Glu Glu Arg Gln Leu Leu Ile Asn His Pro Tyr Glu Lys
    290                 295                 300
Ser Lys Leu Thr Tyr Ala Gln Val Arg Lys Leu Leu Gly Leu Ser Glu
305                 310                 315                 320
Gln Ala Ile Phe Lys His Leu Arg Tyr Ser Lys Glu Asn Ala Glu Ser
                325                 330                 335
Ala Thr Phe Met Glu Leu Lys Ala Trp His Ala Ile Arg Lys Ala Leu
            340                 345                 350
Glu Asn Gln Gly Leu Lys Asp Thr Trp Gln Asp Leu Ala Lys Lys Pro
        355                 360                 365
Asp Leu Leu Asp Glu Ile Gly Thr Ala Phe Ser Leu Tyr Lys Thr Asp
    370                 375                 380
Glu Asp Ile Gln Gln Tyr Leu Thr Asn Lys Val Pro Asn Ser Val Ile
385                 390                 395                 400
Asn Ala Leu Leu Val Ser Leu Asn Phe Asp Lys Phe Ile Glu Leu Ser
                405                 410                 415
Leu Lys Ser Leu Arg Lys Ile Leu Pro Leu Met Glu Gln Gly Lys Arg
            420                 425                 430
Tyr Asp Gln Ala Cys Arg Glu Ile Tyr Gly His His Tyr Gly Glu Ala
        435                 440                 445
Asn Gln Lys Thr Ser Gln Leu Leu Pro Ala Ile Pro Ala Gln Glu Ile
    450                 455                 460
Arg Asn Pro Val Val Leu Arg Thr Leu Ser Gln Ala Arg Lys Val Ile
465                 470                 475                 480
Asn Ala Ile Ile Arg Gln Tyr Gly Ser Pro Ala Arg Val His Ile Glu
                485                 490                 495
Thr Gly Arg Glu Leu Gly Lys Ser Phe Lys Glu Arg Arg Glu Ile Gln
            500                 505                 510
Lys Gln Gln Glu Asp Asn Arg Thr Lys Arg Glu Ser Ala Val Gln Lys
        515                 520                 525
Phe Lys Glu Leu Phe Ser Asp Phe Ser Ser Glu Pro Lys Ser Lys Asp
    530                 535                 540
Ile Leu Lys Phe Arg Leu Tyr Glu Gln Gln His Gly Lys Cys Leu Tyr
545                 550                 555                 560
Ser Gly Lys Glu Ile Asn Ile His Arg Leu Asn Glu Lys Gly Tyr Val
                565                 570                 575
Glu Ile Asp His Ala Leu Pro Phe Ser Arg Thr Trp Asp Asp Ser Phe
            580                 585                 590
```

```
        Asn Asn Lys Val Leu Val Leu Ala Ser Glu Asn Gln Asn Lys Gly Asn
                595                 600                 605
        Gln Thr Pro Tyr Glu Trp Leu Gln Gly Lys Ile Asn Ser Glu Arg Trp
                610                 615                 620
        Lys Asn Phe Val Ala Leu Val Leu Gly Ser Gln Cys Ser Ala Ala Lys
        625                 630                 635                 640
        Lys Gln Arg Leu Leu Thr Gln Val Ile Asp Asp Asn Lys Phe Ile Asp
                            645                 650                 655
        Arg Asn Leu Asn Asp Thr Arg Tyr Ile Ala Arg Phe Leu Ser Asn Tyr
                        660                 665                 670
        Ile Gln Glu Asn Leu Leu Leu Val Gly Lys Asn Lys Lys Asn Val Phe
                    675                 680                 685
        Thr Pro Asn Gly Gln Ile Thr Ala Leu Leu Arg Ser Arg Trp Gly Leu
                690                 695                 700
        Ile Lys Ala Arg Glu Asn Asn Asn Arg His His Ala Leu Asp Ala Ile
        705                 710                 715                 720
        Val Val Ala Cys Ala Thr Pro Ser Met Gln Gln Lys Ile Thr Arg Phe
                            725                 730                 735
        Ile Arg Phe Lys Glu Val His Pro Tyr Lys Ile Glu Asn Arg Tyr Glu
                        740                 745                 750
        Met Val Asp Gln Glu Ser Gly Glu Ile Ile Ser Pro His Phe Pro Glu
                    755                 760                 765
        Pro Trp Ala Tyr Phe Arg Gln Glu Val Asn Ile Arg Val Phe Asp Asn
                770                 775                 780
        His Pro Asp Thr Val Leu Lys Glu Met Leu Pro Asp Arg Pro Gln Ala
        785                 790                 795                 800
        Asn His Gln Phe Val Gln Pro Leu Phe Val Ser Arg Ala Pro Thr Arg
                            805                 810                 815
        Lys Met Ser Gly Gln Gly His Met Glu Thr Ile Lys Ser Ala Lys Arg
                        820                 825                 830
        Leu Ala Glu Gly Ile Ser Val Leu Arg Ile Pro Leu Thr Gln Leu Lys
                    835                 840                 845
        Pro Asn Leu Leu Glu Asn Met Val Asn Lys Glu Arg Glu Pro Ala Leu
                850                 855                 860
        Tyr Ala Gly Leu Lys Ala Arg Leu Ala Glu Phe Asn Gln Asp Pro Ala
        865                 870                 875                 880
        Lys Ala Phe Ala Thr Pro Phe Tyr Lys Gln Gly Gly Gln Gln Val Lys
                            885                 890                 895
        Ala Ile Arg Val Glu Gln Val Gln Lys Ser Gly Val Leu Val Arg Glu
                        900                 905                 910
        Asn Asn Gly Val Ala Asp Asn Ala Ser Ile Val Arg Thr Asp Val Phe
                    915                 920                 925
        Ile Lys Asn Asn Lys Phe Phe Leu Val Pro Ile Tyr Thr Trp Gln Val
                930                 935                 940
        Ala Lys Gly Ile Leu Pro Asn Lys Ala Ile Val Ala His Lys Asn Glu
        945                 950                 955                 960
        Asp Glu Trp Glu Glu Met Asp Glu Gly Ala Lys Phe Lys Phe Ser Leu
                            965                 970                 975
        Phe Pro Asn Asp Leu Val Glu Leu Lys Thr Lys Lys Glu Tyr Phe Phe
                        980                 985                 990
        Gly Tyr Tyr Ile Gly Leu Asp Arg Ala Thr Gly Asn Ile Ser Leu Lys
                    995                 1000                1005
```

| Glu | His | Asp | Gly | Glu | Ile | Ser | Lys | Gly | Lys | Asp | Gly | Val | Tyr | Arg |
|-----|-----|-----|-----|-----|-----|-----|-----|-----|-----|-----|-----|-----|-----|-----|
| 1010| | | | | 1015| | | | | 1020| | | | |

| Val | Gly | Val | Lys | Leu | Ala | Leu | Ser | Phe | Glu | Lys | Tyr | Gln | Val | Asp |
|-----|-----|-----|-----|-----|-----|-----|-----|-----|-----|-----|-----|-----|-----|-----|
| 1025| | | | | 1030| | | | | 1035| | | | |

| Glu | Leu | Gly | Lys | Asn | Arg | Gln | Ile | Cys | Arg | Pro | Gln | Gln | Arg | Gln |
|-----|-----|-----|-----|-----|-----|-----|-----|-----|-----|-----|-----|-----|-----|-----|
| 1040| | | | | 1045| | | | | 1050| | | | |

| Pro | Val | Arg |
|-----|-----|-----|
| 1055| | |

<210> SEQ ID NO 8
<211> LENGTH: 4104
<212> TYPE: DNA
<213> ORGANISM: Streptococcus pyogenes

<400> SEQUENCE: 8

```
atggacaaga agtacagcat cggcctcgac atcggcacca actcggtggg ctgggccgtc      60
atcacggacg aatataaggt cccgtcgaag aagttcaagg tcctcggcaa tacagaccgc     120
cacagcatca agaaaaactt gatcggcgcc ctcctgttcg atagcggcga gaccgcggag     180
gcgaccaggc tcaagaggac cgccaggaga cggtacacta ggcgcaagaa caggatctgc     240
tacctgcagg agatcttcag caacgagatg gcgaaggtgg acgactcctt cttccaccgc     300
ctggaggaat cattcctggt ggaggaggac aagaagcatg agcggcaccc aatcttcggc     360
aacatcgtcg acgaggtggc ctaccacgag aagtacccga caatctacca cctccggaag     420
aaactggtgg acagcacaga caaggcggac ctccggctca tctaccttgc cctcgcgcat     480
atgatcaagt tccgcggcca cttcctcatc gagggcgacc tgaacccgga caactccgac     540
gtggacaagc tgttcatcca gctcgtgcag acgtacaatc aactgttcga ggagaaccct     600
ataaacgcta gcgccgtgga cgccaaggcc atcctctcgg ccaggctctc gaaatcaaga     660
aggctggaga accttatcgc gcagttgcca ggcgaaaaga gaacggcct  cttcggcaac     720 cttattgcgc tcagcctcgg cctgacgccg aacttcaaat caaacttcga cctcgcggag     780
gacgccaagc tccagctctc aaaggacacc tacgacgacg acctcgacaa cctcctggcc     840
cagataggag accagtacgc ggacctcttc ctcgccgcca gaacctctcg cgacgctatc     900
ctgctcagcg acatccttcg ggtcaacacc gaaattacca aggcaccgct gtccgccagc     960
atgattaaac gctacgacga gcaccatcag gacctcacgc tgctcaaggc actcgtccgc    1020
cagcagctcc ccgagaagta caaggagatc ttcttcgacc aatcaaaaaa cggctacgcg    1080
ggatatatcg acggcggtgc cagccaggaa gagttctaca gttcatcaa  ccaatcctg     1140 gagaagatgg acggcaccga ggagttgctg gtcaagctca caggagga   cctcctcagg    1200 aagcaggaga ccttcgacaa cggctccatc ccgcatcaga tccacctggg cgaactgcat    1260
gccatcctgc ggcgccagga ggacttctac ccgttcctga aggataaccg ggagaagatc    1320
gagaagatct tgacgttccg catcccatac tacgtgggcc cgctggctcg cggcaactcc    1380
cggttcgcct ggatgacccg gaagtcggag gagaccatca cccctggaa  ctttgaggag    1440 gtggtcgata agggcgctag cgctcagagc ttcatcgagc gcatgaccaa cttcgataaa    1500
aacctgccca tgaaaaagt  cctccccaag cactcgctgc tctacgagta cttcaccgtg    1560
tacaacgagc tcaccaaggt caaatacgtc accgagggca tgcggaagcc ggcgttcctg    1620
agcggcgagc agaagaaggc gatagtggac ctcctcttca gaccaacag  gaaggtgacc    1680 gtgaagcaat taaagagga  ctacttcaag aaaatagagt gcttcgactc cgtggagatc    1740
tcgggcgtgg aggatcggtt caacgcctca ctcggcacgt atcacgacct cctcaagatc    1800
```

-continued

| | |
|---|---|
| attaaagaca aggacttcct cgacaacgag gagaacgagg acatcctcga ggacatcgtc | 1860 |
| ctcaccctga ccctgttcga ggaccgcgaa atgatcgagg agaggctgaa gacctacgcg | 1920 |
| cacctgttcg acgacaaggt catgaaacag ctcaagaggc gccgctacac tggttgggga | 1980 |
| aggctgtccc gcaagctcat taatggcatc agggacaagc agagcggcaa gaccatcctg | 2040 |
| gacttcctca gtccgacgg gttcgccaac cgcaacttca tgcagctcat tcacgacgac | 2100 |
| tcgctcacgt tcaaggaaga catccagaag gcacaggtga gcgggcaggg tgactccctc | 2160 |
| cacgaacaca tcgccaacct ggccggctcg ccggccatta aaagggcat cctgcagacg | 2220 |
| gtcaaggtcg tcgacgagct cgtgaaggtg atgggccggc acaagcccga aaatatcgtc | 2280 |
| atagagatgg ccaggagaa ccagaccacc caaaagggc agaagaactc gcgcgagcgg | 2340 |
| atgaaacgga tcgaggaggg cattaaagag ctcgggtccc agatcctgaa ggagcacccc | 2400 |
| gtggaaaata cccagctcca gaatgaaaag ctctacctct actacctgca gaacggccgc | 2460 |
| gacatgtacg tggaccagga gctggacatt aatcggctat cggactacga cgtcgaccac | 2520 |
| atcgtgccgc agtcgttcct caaggacgat agcatcgaca acaaggtgct cacccggtcg | 2580 |
| gataaaaatc ggggcaagag cgacaacgtg cccagcgagg aggtcgtgaa gaagatgaaa | 2640 |
| aactactggc gccagctcct caacgcgaaa ctgatcaccc agcgcaagtt cgacaacctg | 2700 |
| acgaaggcgg aacgcggtgg cttgagcgaa ctcgataagg cgggcttcat aaaaaggcag | 2760 |
| ctggtcgaga cgcgccagat cacgaagcat gtcgcccaga tcctggacag ccgcatgaat | 2820 |
| actaagtacg atgaaaacga caagctgatc cgggaggtga aggtgatcac gctgaagtcc | 2880 |
| aagctcgtgt cggacttccg caaggacttc cagttctaca aggtccgcga gatcaacaac | 2940 |
| taccaccacg cccacgacgc ctacctgaat gcggtggtcg ggaccgccct gatcaagaag | 3000 |
| tacccgaagc tggagtcgga gttcgtgtac ggcgactaca aggtctacga cgtgcgcaaa | 3060 |
| atgatcgcca gtccgagca ggagatcggc aaggccacgg caaaatactt cttctactcg | 3120 |
| aacatcatga acttcttcaa gaccgagatc accctcgcga acggcgagat ccgcaagcgc | 3180 |
| ccgctcatcg aaaccaacgg cgagacgggc gagatcgtct gggataaggg ccgggatttc | 3240 |
| gcgacggtcc gcaaggtgct ctccatgccg caagtcaata tcgtgaaaaa gacggaggtc | 3300 |
| cagacgggcg ggttcagcaa ggagtccatc ctcccgaagc gcaactccga caagctcatc | 3360 |
| gcgaggaaga aggattggga cccgaaaaaa tatggcggct tcgacagccc gaccgtcgca | 3420 |
| tacagcgtcc tcgtcgtggc gaaggtggag aagggcaagt caaagaagct caagtccgtg | 3480 |
| aaggagctgc tcgggatcac gattatggag cggtcctcct tcgagaagaa cccgatcgac | 3540 |
| ttcctagagg ccaagggata taaggaggtc aagaaggacc tgattattaa actgccgaag | 3600 |
| tactcgctct tcgagctgga aaacggccgc aagaggatgc tcgcctccgc aggcgagttg | 3660 |
| cagaagggca acgagctcgc cctcccgagc aaatacgtca atttcctgta cctcgctagc | 3720 |
| cactatgaaa agctcaaggg cagcccggag gacaacgagc agaagcagct cttcgtggag | 3780 |
| cagcacaagc attacctgga cgagatcatc gagcagatca gcgagttctc gaagcgggtg | 3840 |
| atcctcgccg acgcgaacct ggacaaggtg ctgtcggcat ataacaagca ccgcgacaaa | 3900 |
| ccaatacgcg agcaggccga aaatatcatc cacctcttca ccctcaccaa cctcggcgct | 3960 |
| ccggcagcct tcaagtactt cgacaccacg attgaccgga agcggtacac gagcacgaag | 4020 |
| gaggtgctcg atgcgacgct gatccaccag agcatcacag ggctctatga aacacgcatc | 4080 |
| gacctgagcc agctgggcgg agac | 4104 |

<210> SEQ ID NO 9
<211> LENGTH: 4155
<212> TYPE: DNA
<213> ORGANISM: Streptococcus pyogenes

<400> SEQUENCE: 9

| | |
|---|---:|
| atggcaccga agaagaagcg caaggtgatg gacaagaagt acagcatcgg cctcgacatc | 60 |
| ggcaccaact cggtgggctg ggccgtcatc acggacgaat ataaggtccc gtcgaagaag | 120 |
| ttcaaggtcc tcggcaatac agaccgccac agcatcaaga aaaacttgat cggcgccctc | 180 |
| ctgttcgata gcgcgagac cgcggaggcg accaggctca agaggaccgc caggagacgg | 240 |
| tacactaggc gcaagaacag gatctgctac ctgcaggaga tcttcagcaa cgagatggcg | 300 |
| aaggtggacg actccttctt ccaccgcctg gaggaatcat tcctggtgga ggaggacaag | 360 |
| aagcatgagc ggcacccaat cttcggcaac atcgtcgacg aggtggccta ccacgagaag | 420 |
| tacccgacaa tctaccacct ccggaagaaa ctggtggaca gcacagacaa ggcggacctc | 480 |
| cggctcatct accttgccct cgcgcatatg atcaagttcc gcggccactt cctcatcgag | 540 |
| ggcgacctga cccggacaa ctccgacgtg gacaagctgt tcatccagct cgtgcagacg | 600 |
| tacaatcaac tgttcgagga aaccccata acgctagcg gcgtggacgc caaggccatc | 660 |
| ctctcggcca ggctctcgaa atcaagaagg ctggagaacc ttatcgcgca gttgccaggc | 720 |
| gaaaagaaga acgcctcttt cggcaacctt attgcgctca gcctcggcct gacgccgaac | 780 |
| ttcaaatcaa acttcgacct cgcggaggac gccaagctcc agctctcaaa ggacacctac | 840 |
| gacgacgacc tcgacaacct cctggcccag ataggagacc agtacgcgga cctcttcctc | 900 |
| gccgccaaga acctctccga cgctatcctg ctcagcgaca tccttcgggt caacaccgaa | 960 |
| attaccaagg caccgctgtc cgccagcatg attaaacgct acgacgagca ccatcaggac | 1020 |
| ctcacgctgc tcaaggcact cgtccgccag cagctccccg agaagtacaa ggagatcttc | 1080 |
| ttcgaccaat caaaaaacgg ctacgcggga tatatcgacg gcggtgccag ccaggaagag | 1140 |
| ttctacaagt tcatcaaacc aatcctggag aagatggacg gcaccgagga gttgctggtc | 1200 |
| aagctcaaca gggaggacct cctcaggaag cagaggacct cgacaacgg ctccatcccg | 1260 |
| catcagatcc acctgggcga actgcatgcc atcctgcggc gccaggagga cttctacccg | 1320 |
| ttcctgaagg ataaccggga gaagatcgag aagatcttga cgttccgcat cccatactac | 1380 |
| gtgggcccgc tggctcgcgg caactcccgg ttcgcctgga tgacccggaa gtcggaggag | 1440 |
| accatcacac cctggaactt tgaggaggtg gtcgataagg cgctagcgc tcagagcttc | 1500 |
| atcgagcgca tgaccaactt cgataaaaac ctgcccaatg aaaaagtcct ccccaagcac | 1560 |
| tcgctgctct acgagtactt caccgtgtac aacgagctca ccaaggtcaa atacgtcacc | 1620 |
| gagggcatgc ggaagccggc gttcctgagc ggcgagcaga agaaggcgat agtggacctc | 1680 |
| ctcttcaaga ccaacaggaa ggtgaccgtg aagcaattaa agaggacta cttcaagaaa | 1740 |
| atagagtgct tcgactccgt ggagatctcg ggcgtggagg atcggttcaa cgcctcactc | 1800 |
| ggcacgtatc acgacctcct caagatcatt aaagacaagg acttcctcga caacgaggag | 1860 |
| aacgaggaca tcctcgagga catcgtcctc accctgaccc tgttcgagga ccgcgaaatg | 1920 |
| atcgaggaga ggctgaagac ctacgcgcac ctgttcgacg acaaggtcat gaaacagctc | 1980 |
| aagaggcgcc gctacactgg ttggggaagg ctgtcccgca agctcattaa tggcatcagg | 2040 |
| gacaagcaga gcggcaagac catcctggac ttcctcaagt ccgacgggtt cgccaaccgc | 2100 |
| aacttcatgc agctcattca cgacgactcg ctcacgttca aggaagacat ccagaaggca | 2160 |

```
caggtgagcg ggcagggtga ctccctccac gaacacatcg ccaacctggc cggctcgccg    2220
gccattaaaa agggcatcct gcagacggtc aaggtcgtcg acgagctcgt gaaggtgatg    2280
ggccggcaca agcccgaaaa tatcgtcata gagatggcca gggagaacca gaccacccaa    2340
aaagggcaga agaactcgcg cgagcggatg aaacggatcg aggagggcat taaagagctc    2400
gggtcccaga tcctgaagga gcaccccgtg gaaaatatcc agctccagaa tgaaaagctc    2460
tacctctact acctgcagaa cggccgcgac atgtacgtgg accaggagct ggacattaat    2520
cggctatcgg actacgacgt cgaccacatc gtgccgcagt cgttcctcaa ggacgatagc    2580
atcgacaaca aggtgctcac ccggtcggat aaaaatcggg gcaagagcga caacgtgccc    2640
agcgaggagg tcgtgaagaa gatgaaaaac tactggcgcc agctcctcaa cgcgaaactg    2700
atcacccagc gcaagttcga caacctgacg aaggcggaac gcggtggctt gagcgaactc    2760
gataaggcgg gcttcataaa aaggcagctg gtcgagacgc gccagatcac gaagcatgtc    2820
gcccagatcc tggacagccg catgaatact aagtacgatg aaaacgacaa gctgatccgg    2880
gaggtgaagg tgatcacgct gaagtccaag ctcgtgtcgg acttccgcaa ggacttccag    2940
ttctacaagg tccgcgagat caacaactac caccacgccc acgacgccta cctgaatgcg    3000
gtggtcggga ccgccctgat caagaagtac ccgaagctgg agtcggagtt cgtgtacggc    3060
gactacaagg tctacgacgt gcgcaaaatg atcgccaagt ccgagcagga gatcggcaag    3120
gccacggcaa atactctctt ctactcgaac atcatgaact tcttcaagac cgagatcacc    3180
ctcgcgaacg gcgagatccg caagcgcccg ctcatcgaaa ccaacggcga gacgggcgag    3240
atcgtctggg ataagggccg ggatttcgcg acggtccgca aggtgctctc catgccgcaa    3300
gtcaatatcg tgaaaaagac ggaggtccag acgggcgggt tcagcaagga gtccatcctc    3360
ccgaagcgca actccgacaa gctcatcgcg aggaagaagg attgggaccc gaaaaaatat    3420
ggcggcttcg acagcccgac cgtcgcatac agcgtcctcg tcgtggcgaa ggtggagaag    3480
ggcaagtcaa agaagctcaa gtccgtgaag gagctgctcg ggatcacgat tatggagcgg    3540
tcctccttcg agaagaaccc gatcgacttc ctagaggcca agggatataa ggaggtcaag    3600
aaggacctga ttattaaact gccgaagtac tcgctcttcg agctggaaaa cggccgcaag    3660
aggatgctcg cctccgcagg cgagttgcag aagggcaacg agctcgccct cccgagcaaa    3720
tacgtcaatt tcctgtacct cgctagccac tatgaaaagc tcaagggcag cccggaggac    3780
aacgagcaga agcagctctt cgtggagcag cacaagcatt acctggacga gatcatcgag    3840
cagatcagcg agttctcgaa gcgggtgatc ctcgccgacg cgaacctgga caaggtgctg    3900
tcggcatata caagcaccg cgacaaacca atacgcgagc aggccgaaaa tatcatccac    3960
ctcttcaccc tcaccaacct cggcgctccg gcagccttca gtacttcga caccacgatt    4020 gaccggaagc ggtacacgag cacgaaggag gtgctcgatg cgacgctgat ccaccagagc    4080
atcacagggc tctatgaaac acgcatcgac ctgagccagc tgggcggaga caagaagaag    4140
aagctcaagc tctag                                                    4155
```

<210> SEQ ID NO 10
<211> LENGTH: 1384
<212> TYPE: PRT
<213> ORGANISM: Streptococcus pyogenes

<400> SEQUENCE: 10

```
Met Ala Pro Lys Lys Arg Lys Val Met Asp Lys Lys Tyr Ser Ile
1               5                   10                  15
```

```
Gly Leu Asp Ile Gly Thr Asn Ser Val Gly Trp Ala Val Ile Thr Asp
             20                  25                  30

Glu Tyr Lys Val Pro Ser Lys Lys Phe Lys Val Leu Gly Asn Thr Asp
             35                  40                  45

Arg His Ser Ile Lys Lys Asn Leu Ile Gly Ala Leu Leu Phe Asp Ser
 50                  55                  60

Gly Glu Thr Ala Glu Ala Thr Arg Leu Lys Arg Thr Ala Arg Arg
 65                  70                  75                  80

Tyr Thr Arg Arg Lys Asn Arg Ile Cys Tyr Leu Gln Glu Ile Phe Ser
                 85                  90                  95

Asn Glu Met Ala Lys Val Asp Asp Ser Phe Phe His Arg Leu Glu Glu
             100                 105                 110

Ser Phe Leu Val Glu Glu Asp Lys Lys His Glu Arg His Pro Ile Phe
             115                 120                 125

Gly Asn Ile Val Asp Glu Val Ala Tyr His Glu Lys Tyr Pro Thr Ile
 130                 135                 140

Tyr His Leu Arg Lys Lys Leu Val Asp Ser Thr Asp Lys Ala Asp Leu
145                 150                 155                 160

Arg Leu Ile Tyr Leu Ala Leu Ala His Met Ile Lys Phe Arg Gly His
                 165                 170                 175

Phe Leu Ile Glu Gly Asp Leu Asn Pro Asp Asn Ser Asp Val Asp Lys
             180                 185                 190

Leu Phe Ile Gln Leu Val Gln Thr Tyr Asn Gln Leu Phe Glu Glu Asn
             195                 200                 205

Pro Ile Asn Ala Ser Gly Val Asp Ala Lys Ala Ile Leu Ser Ala Arg
 210                 215                 220

Leu Ser Lys Ser Arg Arg Leu Glu Asn Leu Ile Ala Gln Leu Pro Gly
225                 230                 235                 240

Glu Lys Lys Asn Gly Leu Phe Gly Asn Leu Ile Ala Leu Ser Leu Gly
                 245                 250                 255

Leu Thr Pro Asn Phe Lys Ser Asn Phe Asp Leu Ala Glu Asp Ala Lys
             260                 265                 270

Leu Gln Leu Ser Lys Asp Thr Tyr Asp Asp Leu Asp Asn Leu Leu
             275                 280                 285

Ala Gln Ile Gly Asp Gln Tyr Ala Asp Leu Phe Leu Ala Ala Lys Asn
 290                 295                 300

Leu Ser Asp Ala Ile Leu Leu Ser Asp Ile Leu Arg Val Asn Thr Glu
305                 310                 315                 320

Ile Thr Lys Ala Pro Leu Ser Ala Ser Met Ile Lys Arg Tyr Asp Glu
                 325                 330                 335

His His Gln Asp Leu Thr Leu Leu Lys Ala Leu Val Arg Gln Gln Leu
             340                 345                 350

Pro Glu Lys Tyr Lys Glu Ile Phe Phe Asp Gln Ser Lys Asn Gly Tyr
             355                 360                 365

Ala Gly Tyr Ile Asp Gly Gly Ala Ser Gln Glu Glu Phe Tyr Lys Phe
 370                 375                 380

Ile Lys Pro Ile Leu Glu Lys Met Asp Gly Thr Glu Glu Leu Leu Val
385                 390                 395                 400

Lys Leu Asn Arg Glu Asp Leu Leu Arg Lys Gln Arg Thr Phe Asp Asn
                 405                 410                 415

Gly Ser Ile Pro His Gln Ile His Leu Gly Glu Leu His Ala Ile Leu
             420                 425                 430
```

```
Arg Arg Gln Glu Asp Phe Tyr Pro Phe Leu Lys Asp Asn Arg Glu Lys
            435                 440                 445

Ile Glu Lys Ile Leu Thr Phe Arg Ile Pro Tyr Tyr Val Gly Pro Leu
    450                 455                 460

Ala Arg Gly Asn Ser Arg Phe Ala Trp Met Thr Arg Lys Ser Glu Glu
465                 470                 475                 480

Thr Ile Thr Pro Trp Asn Phe Glu Glu Val Val Asp Lys Gly Ala Ser
            485                 490                 495

Ala Gln Ser Phe Ile Glu Arg Met Thr Asn Phe Asp Lys Asn Leu Pro
            500                 505                 510

Asn Glu Lys Val Leu Pro Lys His Ser Leu Leu Tyr Glu Tyr Phe Thr
            515                 520                 525

Val Tyr Asn Glu Leu Thr Lys Val Lys Tyr Val Thr Glu Gly Met Arg
    530                 535                 540

Lys Pro Ala Phe Leu Ser Gly Glu Gln Lys Lys Ala Ile Val Asp Leu
545                 550                 555                 560

Leu Phe Lys Thr Asn Arg Lys Val Thr Val Lys Gln Leu Lys Glu Asp
            565                 570                 575

Tyr Phe Lys Lys Ile Glu Cys Phe Asp Ser Val Glu Ile Ser Gly Val
            580                 585                 590

Glu Asp Arg Phe Asn Ala Ser Leu Gly Thr Tyr His Asp Leu Leu Lys
            595                 600                 605

Ile Ile Lys Asp Lys Asp Phe Leu Asp Asn Glu Glu Asn Glu Asp Ile
            610                 615                 620

Leu Glu Asp Ile Val Leu Thr Leu Thr Leu Phe Glu Asp Arg Glu Met
625                 630                 635                 640

Ile Glu Glu Arg Leu Lys Thr Tyr Ala His Leu Phe Asp Asp Lys Val
                    645                 650                 655

Met Lys Gln Leu Lys Arg Arg Arg Tyr Thr Gly Trp Gly Arg Leu Ser
                    660                 665                 670

Arg Lys Leu Ile Asn Gly Ile Arg Asp Lys Gln Ser Gly Lys Thr Ile
            675                 680                 685

Leu Asp Phe Leu Lys Ser Asp Gly Phe Ala Asn Arg Asn Phe Met Gln
690                 695                 700

Leu Ile His Asp Asp Ser Leu Thr Phe Lys Glu Asp Ile Gln Lys Ala
705                 710                 715                 720

Gln Val Ser Gly Gln Gly Asp Ser Leu His Glu His Ile Ala Asn Leu
                725                 730                 735

Ala Gly Ser Pro Ala Ile Lys Lys Gly Ile Leu Gln Thr Val Lys Val
            740                 745                 750

Val Asp Glu Leu Val Lys Val Met Gly Arg His Lys Pro Glu Asn Ile
            755                 760                 765

Val Ile Glu Met Ala Arg Glu Asn Gln Thr Thr Gln Lys Gly Gln Lys
770                 775                 780

Asn Ser Arg Glu Arg Met Lys Arg Ile Glu Glu Gly Ile Lys Glu Leu
785                 790                 795                 800

Gly Ser Gln Ile Leu Lys Glu His Pro Val Glu Asn Thr Gln Leu Gln
                805                 810                 815

Asn Glu Lys Leu Tyr Leu Tyr Tyr Leu Gln Asn Gly Arg Asp Met Tyr
            820                 825                 830

Val Asp Gln Glu Leu Asp Ile Asn Arg Leu Ser Asp Tyr Asp Val Asp
            835                 840                 845

His Ile Val Pro Gln Ser Phe Leu Lys Asp Asp Ser Ile Asp Asn Lys
```

```
                850             855             860
Val Leu Thr Arg Ser Asp Lys Asn Arg Gly Lys Ser Asp Asn Val Pro
865                 870             875                 880

Ser Glu Glu Val Val Lys Lys Met Lys Asn Tyr Trp Arg Gln Leu Leu
                885             890                 895

Asn Ala Lys Leu Ile Thr Gln Arg Lys Phe Asp Asn Leu Thr Lys Ala
            900             905             910

Glu Arg Gly Gly Leu Ser Glu Leu Asp Lys Ala Gly Phe Ile Lys Arg
            915             920             925

Gln Leu Val Glu Thr Arg Gln Ile Thr Lys His Val Ala Gln Ile Leu
        930             935             940

Asp Ser Arg Met Asn Thr Lys Tyr Asp Glu Asn Asp Lys Leu Ile Arg
945             950             955             960

Glu Val Lys Val Ile Thr Leu Lys Ser Lys Leu Val Ser Asp Phe Arg
            965             970             975

Lys Asp Phe Gln Phe Tyr Lys Val Arg Glu Ile Asn Asn Tyr His His
            980             985             990

Ala His Asp Ala Tyr Leu Asn Ala Val Val Gly Thr Ala Leu Ile Lys
        995             1000            1005

Lys Tyr Pro Lys Leu Glu Ser Glu Phe Val Tyr Gly Asp Tyr Lys
        1010            1015            1020

Val Tyr Asp Val Arg Lys Met Ile Ala Lys Ser Glu Gln Glu Ile
        1025            1030            1035

Gly Lys Ala Thr Ala Lys Tyr Phe Phe Tyr Ser Asn Ile Met Asn
        1040            1045            1050

Phe Phe Lys Thr Glu Ile Thr Leu Ala Asn Gly Glu Ile Arg Lys
        1055            1060            1065

Arg Pro Leu Ile Glu Thr Asn Gly Glu Thr Gly Glu Ile Val Trp
        1070            1075            1080

Asp Lys Gly Arg Asp Phe Ala Thr Val Arg Lys Val Leu Ser Met
        1085            1090            1095

Pro Gln Val Asn Ile Val Lys Lys Thr Glu Val Gln Thr Gly Gly
        1100            1105            1110

Phe Ser Lys Glu Ser Ile Leu Pro Lys Arg Asn Ser Asp Lys Leu
        1115            1120            1125

Ile Ala Arg Lys Lys Asp Trp Asp Pro Lys Lys Tyr Gly Gly Phe
        1130            1135            1140

Asp Ser Pro Thr Val Ala Tyr Ser Val Leu Val Val Ala Lys Val
        1145            1150            1155

Glu Lys Gly Lys Ser Lys Lys Leu Lys Ser Val Lys Glu Leu Leu
        1160            1165            1170

Gly Ile Thr Ile Met Glu Arg Ser Ser Phe Glu Lys Asn Pro Ile
        1175            1180            1185

Asp Phe Leu Glu Ala Lys Gly Tyr Lys Glu Val Lys Lys Asp Leu
        1190            1195            1200

Ile Ile Lys Leu Pro Lys Tyr Ser Leu Phe Glu Leu Glu Asn Gly
        1205            1210            1215

Arg Lys Arg Met Leu Ala Ser Ala Gly Glu Leu Gln Lys Gly Asn
        1220            1225            1230

Glu Leu Ala Leu Pro Ser Lys Tyr Val Asn Phe Leu Tyr Leu Ala
        1235            1240            1245

Ser His Tyr Glu Lys Leu Lys Gly Ser Pro Glu Asp Asn Glu Gln
        1250            1255            1260
```

```
Lys Gln Leu Phe Val Glu Gln His Lys His Tyr Leu Asp Glu Ile
    1265                1270                1275
Ile Glu Gln Ile Ser Glu Phe Ser Lys Arg Val Ile Leu Ala Asp
    1280                1285                1290
Ala Asn Leu Asp Lys Val Leu Ser Ala Tyr Asn Lys His Arg Asp
    1295                1300                1305
Lys Pro Ile Arg Glu Gln Ala Glu Asn Ile Ile His Leu Phe Thr
    1310                1315                1320
Leu Thr Asn Leu Gly Ala Pro Ala Ala Phe Lys Tyr Phe Asp Thr
    1325                1330                1335
Thr Ile Asp Arg Lys Arg Tyr Thr Ser Thr Lys Glu Val Leu Asp
    1340                1345                1350
Ala Thr Leu Ile His Gln Ser Ile Thr Gly Leu Tyr Glu Thr Arg
    1355                1360                1365
Ile Asp Leu Ser Gln Leu Gly Gly Asp Lys Lys Lys Leu Lys
    1370                1375                1380

Leu
```

<210> SEQ ID NO 11
<211> LENGTH: 404
<212> TYPE: DNA
<213> ORGANISM: Trichoderma reesei

<400> SEQUENCE: 11

```
aaaaaacact agtaagtact tacttatgta ttattaacta ctttagctaa cttctgcagt    60
actacctaag aggctagggg tagttttata gcagacttat agctattatt tttatttagt   120
aaagtgcttt taaagtaagg tctttttat  agcacttttt atttattata atatatatta   180
tataataatt ttaagcctgg aatagtaaag aggcttatat aataatttat agtaataaaa   240
gcttagcagc tgtaatataa ttcctaaaga aacagcatga atggtatta tgtaagagct    300
atagtctaaa ggcactctgc tggataaaaa tagtggctat aagtctgctg caaaactacc   360
cccaacctcg taggtatata agtactgttt gatggtagtc tatc                   404
```

<210> SEQ ID NO 12
<211> LENGTH: 146
<212> TYPE: DNA
<213> ORGANISM: Trichoderma reesei

<400> SEQUENCE: 12

```
aattcctaaa gaaacagcat gaatggtat tatgtaagag ctatagtcta aaggcactct    60
gctgataaa aatagtggct ataagtctgc tgcaaaacta cccccaacct cgtaggtata   120
taagtactgt tgatggtag tctatc                                        146
```

<210> SEQ ID NO 13
<211> LENGTH: 138
<212> TYPE: DNA
<213> ORGANISM: Artificial Sequence
<220> FEATURE:
<223> OTHER INFORMATION: Synthetic construct

<400> SEQUENCE: 13

```
atgcaccatc atcatcatca ttcttctggt ctggtgccac gcggttctgg tatgaaagaa    60
accgctgctg ctaaattcga acgccagcac atggacagcc agatctggg taccgacgac   120
gacgacaagg ccatggcc                                                138
```

<210> SEQ ID NO 14
<211> LENGTH: 21
<212> TYPE: DNA
<213> ORGANISM: SV40

<400> SEQUENCE: 14
ccaaaaaaga aacgcaaggt t                                              21

<210> SEQ ID NO 15
<211> LENGTH: 4104
<212> TYPE: DNA
<213> ORGANISM: Escherichia coli

<400> SEQUENCE: 15

| | | | | | |
|---|---|---|---|---|---|
| atggataaaa | aatacagcat | tggtctggat | atcggaacca | acagcgttgg | gtgggcagta | 60 |
| ataacagatg | aatacaaagt | gccgtcaaaa | aatttaagg | ttctggggaa | tacagatcgc | 120 |
| cacagcataa | aaagaatct | gattgggca | ttgctgtttg | attcgggtga | dacagctgag | 180 |
| gccacgcgtc | tgaaacgtac | agcaagaaga | cgttacacac | gtcgtaaaaa | tcgtatttgc | 240 |
| tacttacagg | aaattttttc | taacgaaatg | gccaaggtag | atgatagttt | cttccatcgt | 300 |
| ctcgaagaat | cttttctggt | tgaggaagat | aaaaaacacg | aacgtcaccc | tatctttggc | 360 |
| aatatcgtgg | atgaagtggc | ctatcatgaa | aaatacccta | cgatttatca | tcttcgcaag | 420 |
| aagttggttg | atagtacgga | caaagcggat | ctgcgtttaa | tctatcttgc | gttagcgcac | 480 |
| atgatcaaat | tcgtggtca | tttcttaatt | gaaggtgatc | tgaatcctga | taactctgat | 540 |
| gtggacaaat | tgtttataca | attagtgcaa | acctataatc | agctgttcga | ggaaaacccc | 600 |
| attaatgcct | ctggagttga | tgccaaagcg | attttaagcg | cgagactttc | taagtcccgg | 660 |
| cgtctggaga | atctgatcgc | ccagttacca | ggggaaaaga | aaaatggtct | gtttggtaat | 720 |
| ctgattgccc | tcagtctggg | gcttaccccg | aacttcaaat | ccaattttga | cctggctgag | 780 |
| gacgcaaagc | tgcagctgag | caaagatact | tatgatgatg | acctcgacaa | tctgctcgcc | 840 |
| cagattggtg | accaatatgc | ggatctgttt | ctggcagcga | gaatctttc | ggatgctatc | 900 |
| ttgctgtcgg | atattctgcg | tgttaatacc | gaaatcacca | aagcgcctct | gtctgcaagt | 960 |
| atgatcaaga | gatacgacga | gcaccaccag | gacctgactc | ttcttaaggc | actggtacgc | 1020 |
| caacagcttc | cggagaaata | caagaaata | ttcttcgacc | agtccaagaa | tggttacgcg | 1080 |
| ggctacatcg | atggtggtgc | atcacaggaa | gagttctata | aatttattaa | accaatcctt | 1140 |
| gagaaaatgg | atggcacgga | agagttactt | gttaaactta | accgcgaaga | cttgcttaga | 1200 |
| aagcaacgta | cattcgacaa | cggctccatc | ccacaccaga | ttcatttagg | tgaacttcac | 1260 |
| gccatcttgc | gcagacaaga | agatttctat | cccttcttaa | aagacaatcg | ggagaaaatc | 1320 |
| gagaagatcc | tgacgttccg | cattccctat | tatgtcggtc | ccctggcacg | tggtaattct | 1380 |
| cggtttgcct | ggatgacgcg | caaaagtgag | gaaaccatca | ccccttggaa | ctttgaagaa | 1440 |
| gtcgtggata | aaggtgctag | cgcgcagtct | tttatagaaa | gaatgacgaa | cttcgataaa | 1500 |
| aacttgccca | acgaaaaagt | cctgcccaag | cactctctt | tatatgagta | ctttactgtg | 1560 |
| tacaacgaac | tgactaaagt | gaaatacgtt | acgaaggta | tgcgcaaacc | tgcctttctt | 1620 |
| agtggcgagc | agaaaaaagc | aattgtcgat | cttctcttta | aaacgaatcg | caaggtaact | 1680 |
| gtaaaacagc | tgaaggaaga | ttatttcaaa | aagatcgaat | gctttgattc | tgtcgagatc | 1740 |
| tcgggtgtcg | aagatcgttt | caacgcttcc | ttagggacct | atcatgattt | gctgaagata | 1800 |
| ataaaagaca | aagactttct | cgacaatgaa | gaaaatgaag | atattctgga | ggatattgtt | 1860 |

```
ttgaccttga ccttattcga agatagagag atgatcgagg agcgcttaaa aacctatgcc    1920
cacctgtttg atgacaaagt catgaagcaa ttaaagcgcc gcagatatac ggggtggggc    1980
cgcttgagcc gcaagttgat taacggtatt agagacaagc agagcggaaa aactatcctg    2040
gatttcctca aatctgacgg atttgcgaac cgcaatttta tgcagcttat acatgatgat    2100
tcgcttacat tcaaagagga tattcagaag gctcaggtgt ctgggcaagg tgattcactc    2160
cacgaacata tagcaaattt ggccggctct cctgcgatta agaaggggat cctgcaaaca    2220
gttaaagttg tggatgaact tgtaaaagta atgggccgcc acaagccgga gaatatcgtg    2280
atagaaatgg cgcgcgagaa tcaaacgaca caaaaaggtc aaaagaactc aagagagaga    2340
atgaagcgca ttgaggaggg gataaaggaa cttggatctc aaattctgaa agaacatcca    2400
gttgaaaaca ctcagctgca aaatgaaaaa ttgtacctgt actacctgca gaatggaaga    2460
gacatgtacg tggatcagga attggatatc aatagactct cggactatga cgtagatcac    2520
attgtccctc agagcttcct caaggatgat tctatagata taaagtact tacgagatcg    2580 gacaaaaatc gcggtaaatc ggataacgtc ccatcggagg aagtcgttaa aaagatgaaa    2640
aactattggc gtcaactgct gaacgccaag ctgatcacac agcgtaagtt tgataatctg    2700
actaaagccg aacgcggtgg tcttagtgaa ctcgataaag caggatttat aaaacggcag    2760
ttagtagaaa cgcgccaaat tacgaaacac gtggctcaga tcctcgattc tagaatgaat    2820
acaaagtacg atgaaaacga taaactgatc cgtgaagtaa aagtcattac cttaaaatct    2880
aaacttgtgt ccgatttccg caaagatttt cagttttaca aggtccggga atcaataac    2940 tatcaccatg cacatgatgc atatttaaat gcggttgtag gcacggccct tattaagaaa    3000
taccctaaac tcgaaagtga gtttgtttat ggggattata aagtgtatga cgttcgcaaa    3060
atgatcgcga aatcagaaca ggaaatcggt aaggctaccg ctaaatactt ttttttattcc    3120 aacattatga atttttttaa gaccgaaata actctcgcga atggtgaaat ccgtaaacgg    3180
cctcttatag aaaccaatgg tgaaacggga gaaatcgttt gggataaagg tcgtgacttt    3240
gccaccgttc gtaaagtcct ctcaatgccg caagttaaca ttgtcaagaa gacgaagtt    3300 caaacagggg gattctccaa agaatctatc ctgccgaagc gtaacagtga taaacttatt    3360
gccagaaaaa aagattggga tccaaaaaaaa tacggaggct tgattcccc taccgtcgcg    3420 tatagtgtgc tggtggttgc taaagtcgag aaagggaaaa gcagaaaatt gaaatcagtt    3480
aaagaactgc tgggtattac aattatggaa agatcgtcct ttgagaaaaa tccgatcgac    3540 ttttttagagg ccaagggggta taaggaagtg aaaaaagatc tcatcatcaa attaccgaag    3600 tatagtctttt ttgagctgga aaacggcaga aaaagaatgc tggcctccgc gggcgagtta    3660
cagaagggaa atgagctggc gctgccttcc aaatatgtta attttctgta ccttgccagt    3720
cattatgaga aactgaaggg cagccccgaa gataacgaac agaaacaatt attcgtggaa    3780
cagcataagc actatttaga tgaaattata gagcaaatta gtgaattttc taagcgcgtt    3840
atcctcgcgg atgctaattt agacaaagta ctgtcagctt ataataaaca tcgggataag    3900
ccgattagag aacaggccga aaatatcatt catttgttta ccttaaccaa ccttggagca    3960
ccagctgcct tcaaatattt cgataccaca attgatcgta aacggtatac aagtacaaaa    4020
gaagtcttgg acgcaaccct cattcatcaa tctattactg gattatatga gacacgcatt    4080
gatctttcac agctgggcgg agac                                           4104
```

<210> SEQ ID NO 16

```
<211> LENGTH: 21
<212> TYPE: DNA
<213> ORGANISM: Trichoderma reesei

<400> SEQUENCE: 16
aagaagaaaa aactgaaact g                                              21

<210> SEQ ID NO 17
<211> LENGTH: 4284
<212> TYPE: DNA
<213> ORGANISM: Artificial Sequence
<220> FEATURE:
<223> OTHER INFORMATION: Synthetic construct

<400> SEQUENCE: 17
atgcaccatc atcatcatca ttcttctggt ctggtgccac gcggttctgg tatgaaagaa      60
accgctgctg ctaaattcga acgccagcac atggacagcc agatctgggt accgacgac     120 gacgacaagg ccatggcccc aaaaaagaaa cgcaaggtta tggataaaaa atacagcatt     180
ggtctggata tcggaaccaa cagcgttggg tgggcagtaa taacagatga atacaaagtg     240
ccgtcaaaaa aatttaaggt tctggggaat acagatcgcc acagcataaa aagaatctg     300 attggggcat tgctgtttga ttcgggtgag acagctgagg ccacgcgtct gaaacgtaca     360
gcaagaagac gttacacacg tcgtaaaaat cgtatttgct acttacagga aatttttct     420 aacgaaatgg ccaaggtaga tgatagtttc ttccatcgtc tcgaagaatc ttttctggtt     480
gaggaagata aaaacacga acgtcaccct atctttggca atatcgtgga tgaagtggcc     540
tatcatgaaa ataccctac gatttatcat cttcgcaaga agttggttga tagtacggac     600
aaagcggatc tgcgtttaat ctatcttgcg ttagcgcaca tgatcaaatt tcgtggtcat     660
ttcttaattg aaggtgatct gaatcctgat aactctgatg tggacaaatt gtttatacaa     720
ttagtgcaaa cctataatca gctgttcgag gaaaaccca ttaatgcctc tggagttgat     780
gccaaagcga ttttaagcgc gagactttct aagtcccggc gtctggagaa tctgatcgcc     840
cagttaccag gggaaaagaa aaatggtctg tttggtaatc tgattgccct cagtctgggg     900
cttaccccga acttcaaatc caattttgac ctggctgagg acgcaaagct gcagctgagc     960
aaagatactt atgatgatga cctcgacaat ctgctcgccc agattggtga ccaatatgcg    1020
gatctgtttc tggcagcgaa gaatctttcg gatgctatct tgctgtcgga tattctgcgt    1080
gttaataccg aaatcaccaa agcgcctctg tctgcaagta tgatcaagag atacgacgag    1140
caccaccagg aacctgactct tcttaaggca ctggtacgcc aacagcttcc ggagaaatac    1200
aaagaaatat tcttcgacca gtccaagaat ggttacgcgg gctacatcga tggtggtgca    1260
tcacaggaag agttctataa atttattaaa ccaatccttg agaaaatgga tggcacggaa    1320
gagttacttg ttaaacttaa ccgcgaagac ttgcttagaa agcaacgtac attcgacaac    1380
ggctccatcc cacaccagat tcatttaggt gaacttcacg ccatcttgcg cagacaagaa    1440
gatttctatc ccttcttaaa agacaatcgg gagaaaatcg agaagatcct gacgttccgc    1500
attccctatt atgtcggtcc cctggcacgt ggtaattctc ggtttgcctg atgacgcgc    1560 aaaagtgagg aaaccatcac cccttggaac tttgaagaag tcgtggataa aggtgctagc    1620
gcgcagtctt ttatagaaag aatgacgaac ttcgataaaa acttgccaa cgaaaaagtc    1680 ctgcccaagc actctctttt tatatgagtac tttactgtgt acaacgaact gactaaagtg    1740
aaatacgtta cggaaggtat gcgcaaacct gcctttctta gtggcgagca gaaaaaagca    1800
attgtcgatc ttctctttaa aacgaatcgc aaggtaactg taaaacagct gaaggaagat    1860
```

```
tatttcaaaa agatcgaatg ctttgattct gtcgagatct cgggtgtcga agatcgtttc    1920
aacgcttcct tagggaccta tcatgatttg ctgaagataa taaaagacaa agactttctc    1980
gacaatgaag aaaatgaaga tattctggag gatattgttt tgaccttgac cttattcgaa    2040
gatagagaga tgatcgagga gcgcttaaaa acctatgccc acctgtttga tgacaaagtc    2100
atgaagcaat taaagcgccg cagatatacg gggtggggcc gcttgagccg caagttgatt    2160
aacggtatta gagacaagca gagcggaaaa actatcctgg atttcctcaa atctgacgga    2220
tttgcgaacc gcaattttat gcagcttata catgatgatt cgcttacatt caaagaggat    2280
attcagaagg ctcaggtgtc tgggcaaggt gattcactcc acgaacatat agcaaatttg    2340
gccggctctc ctgcgattaa aaggggatc ctgcaaacag ttaaagttgt ggatgaactt    2400
gtaaaagtaa tgggccgcca aagccggag aatatcgtga tagaaatggc gcgcgagaat    2460
caaacgacac aaaaaggtca aaagaactca agagagagaa tgaagcgcat tgaggagggg    2520
ataaaggaac ttggatctca aattctgaaa gaacatccag ttgaaaacac tcagctgcaa    2580
aatgaaaaat tgtacctgta ctacctgcag aatggaagag acatgtacgt ggatcaggaa    2640
ttggatatca atagactctc ggactatgac gtagatcaca ttgtccctca gagcttcctc    2700
aaggatgatt ctatagataa taaagtactt acgagatcgg acaaaaatcg cggtaaatcg    2760
gataacgtcc catcggagga agtcgttaaa aagatgaaaa actattggcg tcaactgctg    2820
aacgccaagc tgatcacaca gcgtaagttt gataatctga ctaaagccga acgcggtggt    2880
cttagtgaac tcgataaagc aggatttata aaacggcagt tagtagaaac gcgccaaatt    2940
acgaaacacg tggctcagat cctcgattct agaatgaata caaagtacga tgaaaacgat    3000
aaactgatcc gtgaagtaaa agtcattacc ttaaaatcta aacttgtgtc cgatttccgc    3060
aaagattttc agttttacaa ggtccgggaa atcaataact atcaccatgc acatgatgca    3120
tatttaaatg cggttgtagg cacggccctt attaagaaat accctaaaact cgaaagtgag    3180 tttgtttatg gggattataa agtgtatgac gttcgcaaaa tgatcgcgaa atcagaacag    3240
gaaatcggta aggctaccgc taaatacttt tttattcca acattatgaa ttttttttaag    3300 accgaaataa ctctcgcgaa tggtgaaatc cgtaaacggc tcttataga aaccaatggt    3360 gaaacgggag aaatcgtttg ggataaaggt cgtgactttg ccaccgttcg taaagtcctc    3420
tcaatgccgc aagttaacat tgtcaagaag acggaagttc aaacaggggg attctccaaa    3480
gaatctatcc tgccgaagcg taacagtgat aaacttattg ccagaaaaaa agattgggat    3540
ccaaaaaaat acgagggctt tgattcccct accgtcgcgt atagtgtgct ggtggttgct    3600
aaagtcgaga aagggaaaag caagaaattg aaatcagtta agaactgct gggtattaca    3660 attatgaaa gatcgtcctt tgagaaaaat ccgatcgact ttttagaggc caaggggtat    3720
aaggaagtga aaaagatct catcatcaaa ttaccgaagt atagtctttt tgagctggaa    3780
aacggcagaa aaagaatgct ggcctccgcg ggcgagttac agaagggaaa tgagctggcg    3840
ctgccttcca aatatgttaa ttttctgtac cttgccagtc attatgagaa actgaagggc    3900
agccccgaag ataacgaaca gaaacaatta ttcgtggaac agcataagca ctatttagat    3960
gaaattatag agcaaattag tgaattttct aagcgcgtta tcctcgcgga tgctaattta    4020
gacaaagtac tgtcagctta taataaacat cgggataagc cgattagaga acaggccgaa    4080
aatatcattc atttgtttac cttaaccaac cttggagcac cagctgcctt caaatatttc    4140
gataccacaa ttgatcgtaa acggtataca agtacaaaag aagtcttgga cgcaacccctc    4200
```

```
attcatcaat ctattactgg attatatgag acacgcattg atctttcaca gctgggcgga    4260
gacaagaaga aaaaactgaa actg                                           4284
```

<210> SEQ ID NO 18
<211> LENGTH: 46
<212> TYPE: PRT
<213> ORGANISM: Artificial Sequence
<220> FEATURE:
<223> OTHER INFORMATION: Synthetic construct

<400> SEQUENCE: 18

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys Ala Met Ala
        35                  40                  45

<210> SEQ ID NO 19
<211> LENGTH: 7
<212> TYPE: PRT
<213> ORGANISM: SV40

<400> SEQUENCE: 19

Pro Lys Lys Lys Arg Lys Val
1               5

<210> SEQ ID NO 20
<211> LENGTH: 7
<212> TYPE: PRT
<213> ORGANISM: Trichoderma reesei

<400> SEQUENCE: 20

Lys Lys Lys Lys Leu Lys Leu
1               5

<210> SEQ ID NO 21
<211> LENGTH: 1428
<212> TYPE: PRT
<213> ORGANISM: Artificial Sequence
<220> FEATURE:
<223> OTHER INFORMATION: protein expressed from Synthetic construct

<400> SEQUENCE: 21

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys Ala Met Ala Pro Lys
        35                  40                  45

Lys Lys Arg Lys Val Met Asp Lys Lys Tyr Ser Ile Gly Leu Asp Ile
    50                  55                  60

Gly Thr Asn Ser Val Gly Trp Ala Val Ile Thr Asp Glu Tyr Lys Val
65                  70                  75                  80

Pro Ser Lys Lys Phe Lys Val Leu Gly Asn Thr Asp Arg His Ser Ile
                85                  90                  95

Lys Lys Asn Leu Ile Gly Ala Leu Leu Phe Asp Ser Gly Glu Thr Ala
            100                 105                 110

Glu Ala Thr Arg Leu Lys Arg Thr Ala Arg Arg Arg Tyr Thr Arg Arg
        115                 120                 125

```
Lys Asn Arg Ile Cys Tyr Leu Gln Glu Ile Phe Ser Asn Glu Met Ala
            130                 135                 140
Lys Val Asp Asp Ser Phe Phe His Arg Leu Glu Glu Ser Phe Leu Val
145                 150                 155                 160
Glu Glu Asp Lys Lys His Glu Arg His Pro Ile Phe Gly Asn Ile Val
                165                 170                 175
Asp Glu Val Ala Tyr His Glu Lys Tyr Pro Thr Ile Tyr His Leu Arg
                180                 185                 190
Lys Lys Leu Val Asp Ser Thr Asp Lys Ala Asp Leu Arg Leu Ile Tyr
            195                 200                 205
Leu Ala Leu Ala His Met Ile Lys Phe Arg Gly His Phe Leu Ile Glu
            210                 215                 220
Gly Asp Leu Asn Pro Asp Asn Ser Asp Val Asp Lys Leu Phe Ile Gln
225                 230                 235                 240
Leu Val Gln Thr Tyr Asn Gln Leu Phe Glu Glu Asn Pro Ile Asn Ala
                245                 250                 255
Ser Gly Val Asp Ala Lys Ala Ile Leu Ser Ala Arg Leu Ser Lys Ser
                260                 265                 270
Arg Arg Leu Glu Asn Leu Ile Ala Gln Leu Pro Gly Glu Lys Lys Asn
            275                 280                 285
Gly Leu Phe Gly Asn Leu Ile Ala Leu Ser Leu Gly Leu Thr Pro Asn
            290                 295                 300
Phe Lys Ser Asn Phe Asp Leu Ala Glu Asp Ala Lys Leu Gln Leu Ser
305                 310                 315                 320
Lys Asp Thr Tyr Asp Asp Asp Leu Asp Asn Leu Leu Ala Gln Ile Gly
                325                 330                 335
Asp Gln Tyr Ala Asp Leu Phe Leu Ala Ala Lys Asn Leu Ser Asp Ala
                340                 345                 350
Ile Leu Leu Ser Asp Ile Leu Arg Val Asn Thr Glu Ile Thr Lys Ala
            355                 360                 365
Pro Leu Ser Ala Ser Met Ile Lys Arg Tyr Asp Glu His His Gln Asp
            370                 375                 380
Leu Thr Leu Leu Lys Ala Leu Val Arg Gln Gln Leu Pro Glu Lys Tyr
385                 390                 395                 400
Lys Glu Ile Phe Phe Asp Gln Ser Lys Asn Gly Tyr Ala Gly Tyr Ile
                405                 410                 415
Asp Gly Gly Ala Ser Gln Glu Glu Phe Tyr Lys Phe Ile Lys Pro Ile
                420                 425                 430
Leu Glu Lys Met Asp Gly Thr Glu Glu Leu Leu Val Lys Leu Asn Arg
            435                 440                 445
Glu Asp Leu Leu Arg Lys Gln Arg Thr Phe Asp Asn Gly Ser Ile Pro
450                 455                 460
His Gln Ile His Leu Gly Glu Leu His Ala Ile Leu Arg Arg Gln Glu
465                 470                 475                 480
Asp Phe Tyr Pro Phe Leu Lys Asp Asn Arg Glu Lys Ile Glu Lys Ile
                485                 490                 495
Leu Thr Phe Arg Ile Pro Tyr Tyr Val Gly Pro Leu Ala Arg Gly Asn
            500                 505                 510
Ser Arg Phe Ala Trp Met Thr Arg Lys Ser Glu Glu Thr Ile Thr Pro
            515                 520                 525
Trp Asn Phe Glu Glu Val Val Asp Lys Gly Ala Ser Ala Gln Ser Phe
530                 535                 540
Ile Glu Arg Met Thr Asn Phe Asp Lys Asn Leu Pro Asn Glu Lys Val
```

```
545                 550                 555                 560
Leu Pro Lys His Ser Leu Leu Tyr Glu Tyr Phe Thr Val Tyr Asn Glu
                565                 570                 575
Leu Thr Lys Val Lys Tyr Val Thr Glu Gly Met Arg Lys Pro Ala Phe
                580                 585                 590
Leu Ser Gly Glu Gln Lys Lys Ala Ile Val Asp Leu Leu Phe Lys Thr
                595                 600                 605
Asn Arg Lys Val Thr Val Lys Gln Leu Lys Glu Asp Tyr Phe Lys Lys
                610                 615                 620
Ile Glu Cys Phe Asp Ser Val Glu Ile Ser Gly Val Glu Asp Arg Phe
625                 630                 635                 640
Asn Ala Ser Leu Gly Thr Tyr His Asp Leu Leu Lys Ile Ile Lys Asp
                645                 650                 655
Lys Asp Phe Leu Asp Asn Glu Glu Asn Glu Asp Ile Leu Glu Asp Ile
                660                 665                 670
Val Leu Thr Leu Thr Leu Phe Glu Asp Arg Glu Met Ile Glu Glu Arg
                675                 680                 685
Leu Lys Thr Tyr Ala His Leu Phe Asp Asp Lys Val Met Lys Gln Leu
                690                 695                 700
Lys Arg Arg Arg Tyr Thr Gly Trp Gly Arg Leu Ser Arg Lys Leu Ile
705                 710                 715                 720
Asn Gly Ile Arg Asp Lys Gln Ser Gly Lys Thr Ile Leu Asp Phe Leu
                725                 730                 735
Lys Ser Asp Gly Phe Ala Asn Arg Asn Phe Met Gln Leu Ile His Asp
                740                 745                 750
Asp Ser Leu Thr Phe Lys Glu Asp Ile Gln Lys Ala Gln Val Ser Gly
                755                 760                 765
Gln Gly Asp Ser Leu His Glu His Ile Ala Asn Leu Ala Gly Ser Pro
                770                 775                 780
Ala Ile Lys Lys Gly Ile Leu Gln Thr Val Lys Val Val Asp Glu Leu
785                 790                 795                 800
Val Lys Val Met Gly Arg His Lys Pro Glu Asn Ile Val Ile Glu Met
                805                 810                 815
Ala Arg Glu Asn Gln Thr Thr Gln Lys Gly Gln Lys Asn Ser Arg Glu
                820                 825                 830
Arg Met Lys Arg Ile Glu Glu Gly Ile Lys Glu Leu Gly Ser Gln Ile
                835                 840                 845
Leu Lys Glu His Pro Val Glu Asn Thr Gln Leu Gln Asn Glu Lys Leu
                850                 855                 860
Tyr Leu Tyr Tyr Leu Gln Asn Gly Arg Asp Met Tyr Val Asp Gln Glu
865                 870                 875                 880
Leu Asp Ile Asn Arg Leu Ser Asp Tyr Asp Val Asp His Ile Val Pro
                885                 890                 895
Gln Ser Phe Leu Lys Asp Asp Ser Ile Asp Asn Lys Val Leu Thr Arg
                900                 905                 910
Ser Asp Lys Asn Arg Gly Lys Ser Asp Asn Val Pro Ser Glu Glu Val
                915                 920                 925
Val Lys Lys Met Lys Asn Tyr Trp Arg Gln Leu Leu Asn Ala Lys Leu
                930                 935                 940
Ile Thr Gln Arg Lys Phe Asp Asn Leu Thr Lys Ala Glu Arg Gly Gly
945                 950                 955                 960
Leu Ser Glu Leu Asp Lys Ala Gly Phe Ile Lys Arg Gln Leu Val Glu
                965                 970                 975
```

```
Thr Arg Gln Ile Thr Lys His Val Ala Gln Ile Leu Asp Ser Arg Met
            980                 985                 990

Asn Thr Lys Tyr Asp Glu Asn Asp  Lys Leu Ile Arg Glu  Val Lys Val
            995                 1000                1005

Ile Thr Leu Lys Ser Lys Leu  Val Ser Asp Phe Arg  Lys Asp Phe
         1010               1015                1020

Gln Phe Tyr Lys Val Arg Glu  Ile Asn Asn Tyr His  His Ala His
         1025               1030                1035

Asp Ala Tyr Leu Asn Ala Val  Val Gly Thr Ala Leu  Ile Lys Lys
         1040               1045                1050

Tyr Pro Lys Leu Glu Ser Glu  Phe Val Tyr Gly Asp  Tyr Lys Val
         1055               1060                1065

Tyr Asp Val Arg Lys Met Ile  Ala Lys Ser Glu Gln  Glu Ile Gly
         1070               1075                1080

Lys Ala Thr Ala Lys Tyr Phe  Phe Tyr Ser Asn Ile  Met Asn Phe
         1085               1090                1095

Phe Lys Thr Glu Ile Thr Leu  Ala Asn Gly Glu Ile  Arg Lys Arg
         1100               1105                1110

Pro Leu Ile Glu Thr Asn Gly  Glu Thr Gly Glu Ile  Val Trp Asp
         1115               1120                1125

Lys Gly Arg Asp Phe Ala Thr  Val Arg Lys Val Leu  Ser Met Pro
         1130               1135                1140

Gln Val Asn Ile Val Lys Lys  Thr Glu Val Gln Thr  Gly Gly Phe
         1145               1150                1155

Ser Lys Glu Ser Ile Leu Pro  Lys Arg Asn Ser Asp  Lys Leu Ile
         1160               1165                1170

Ala Arg Lys Lys Asp Trp Asp  Pro Lys Lys Tyr Gly  Gly Phe Asp
         1175               1180                1185

Ser Pro Thr Val Ala Tyr Ser  Val Leu Val Val Ala  Lys Val Glu
         1190               1195                1200

Lys Gly Lys Ser Lys Lys Leu  Lys Ser Val Lys Glu  Leu Leu Gly
         1205               1210                1215

Ile Thr Ile Met Glu Arg Ser  Ser Phe Glu Lys Asn  Pro Ile Asp
         1220               1225                1230

Phe Leu Glu Ala Lys Gly Tyr  Lys Glu Val Lys Lys  Asp Leu Ile
         1235               1240                1245

Ile Lys Leu Pro Lys Tyr Ser  Leu Phe Glu Leu Glu  Asn Gly Arg
         1250               1255                1260

Lys Arg Met Leu Ala Ser Ala  Gly Glu Leu Gln Lys  Gly Asn Glu
         1265               1270                1275

Leu Ala Leu Pro Ser Lys Tyr  Val Asn Phe Leu Tyr  Leu Ala Ser
         1280               1285                1290

His Tyr Glu Lys Leu Lys Gly  Ser Pro Glu Asp Asn  Glu Gln Lys
         1295               1300                1305

Gln Leu Phe Val Glu Gln His  Lys His Tyr Leu Asp  Glu Ile Ile
         1310               1315                1320

Glu Gln Ile Ser Glu Phe Ser  Lys Arg Val Ile Leu  Ala Asp Ala
         1325               1330                1335

Asn Leu Asp Lys Val Leu Ser  Ala Tyr Asn Lys His  Arg Asp Lys
         1340               1345                1350

Pro Ile Arg Glu Gln Ala Glu  Asn Ile Ile His Leu  Phe Thr Leu
         1355               1360                1365
```

```
Thr Asn Leu Gly Ala Pro Ala Ala Phe Lys Tyr Phe Asp Thr Thr
    1370            1375                1380
Ile Asp Arg Lys Arg Tyr Thr Ser Thr Lys Glu Val Leu Asp Ala
1385                1390                1395
Thr Leu Ile His Gln Ser Ile Thr Gly Leu Tyr Glu Thr Arg Ile
    1400            1405                1410
Asp Leu Ser Gln Leu Gly Gly Asp Lys Lys Lys Leu Lys Leu
    1415            1420                1425

<210> SEQ ID NO 22
<211> LENGTH: 4889
<212> TYPE: DNA
<213> ORGANISM: Trichoderma reesei

<400> SEQUENCE: 22
gactgtctcc accatgtaat ttttccctgc gactccatat aacgccggat cgtgaaattt      60
tcttctttct tttccttcct tctcaacaaa caacggatct gtgctttgcg gtccctgcg     120
ttcacgcgtc agggtcgact gctctgcagc tcgataactc catggagcca tcaacttgct    180
atggtgtcaa tcatcctatc gacaggtcca agaacaagcc ggcctccggc tgcctcattc    240
gctgtcgcaa gacggcttga gtgttgtggc tggaggattc gggggcccca tattccaacc    300
ctttttttcca aggccgtcgg ccggtgaggt tgaggaaaac catgggttgc ctacatatta   360
tcgatgctgg tgtttggtag tagcaatgtt tgcggtggca gtttgagccg agcctcgtct    420
tgggcttctg acccaggcaa cgccatctga ctagctgcgc cgaaggaagg atgattcatt    480
gtacgacgcc agtcaatgga atcttcaagt aaaagcccga cgaaccgacc atgtcagata    540
tcagaattct cctggctggt ggggttggtt ggagactgct tacggagtcg atgcctcgtg    600
actgtcatgg ccgcgtccag cctcctggga ctctgtccga tattatgaca cgagtaaagc    660
ctgcatgatg tcagtttgct gcgtctcatg tcgagaacaa cacacctggt gctacatagg    720
caatactacc tcgtagcttc aaagttgact gttttgcttt gatgtctttg atcatgccca    780
tccatccctt gtcttgcagt gcatgtggat ctctacgtcc agacggggag aaagcttgtc    840
tgtgataaag tacgatgatg cattgatgcc tgtggctacg gccctttat cccccatcgtc    900
atgcatctct atattaatcc aggagactct cctcctggca tgggtgagta caagtgacga    960
ggacatgtag aagcagagcc acgcaacgtc ttgacatctg tacctatttt gggccaaaaa   1020
tcgagaccca ccagctcgtc ctaccttaca tgtgaagatc ttagcccaca atcctactgt   1080
tttactagta ttactgcaca gctgtcatca cgagtcctcg gttgcttgtg aaacccagct   1140
cagctcctga gcacatgcag taacgccgac tcggcgtcat ttcgccacac ccaatttgga   1200
cctgagggat gctggaagct gctgagcaga tcccgttacc gattcatggc actactacat   1260
ccatacgcag caaacatggg cttgggcttg gcttctcaat gcaaaattgc ccgcaaaagt   1320
cccggcattg tcgatgcaga gatgcagatt tcagcgggcg attctagggt agggcgacta   1380
ctactactaa taccacctag tcagtatgta tctagcaccg gaggctaggc ggttagtgga   1440
cgggaacctg gtcattccat cgcaaccagg atcccgcact tcgttgcgct tctgccccca   1500
cggggcggga gttggcagag gcagaatgcg gagcagcccc ttgtctgccc tggcgggggc   1560
ctgttgaagc aagcagacga gagcagagcg gttgagaagc ggtggttgac gcttgacggt   1620
acgaagacga gcgagaatcc cgttaagccg aggctgggct ccccccccg tcatcatcat   1680
gcccatcctc ctcttccagc ccactcgtct ccctgcctcg tcgcctcccc tcctcccc     1740
gattagctgc gcatgttctc ctgacagcgt gactaatgac gcgttgccag cccattcgcc   1800
```

```
tgacgcatcc cggcatctga gtctagctcg tcacgctggc aatcttggcc caggcagagc  1860
agcaagacgg cgggcatgat tgggccgtgc cctggcgggc atcagctggc catccgctgc  1920
cacccgagac cgcatcaccg acttgtcgga tctctccgag cagcaggagg ctgatcctgg  1980
ccggcgagac gattgaaaag ggctgccggg cccggagcag gacagcggcg agagcgagcg  2040
agagagagga aaagaagaag gtcgactgtc ttattttcag ccagccccgg ctcaacagaa  2100
gcagaggaga aggcgaacga cgtcaacgac gacgacgacg acgacgaaga cggtgaagtc  2160
cgttagttga agatccttgc cgtcacaaca ccatctcgtg gatattgctt tccctgccg   2220 ttgcgttgcc acctgttccc tctttctctt cccccttct tcctcattcc gagcgctact   2280
ggttcctact ccgcagcctt cggttgtgcc tttctctttg tcgaccattg caccgcccgt   2340
cgcggcactt gggccccgga gaattcggcc cttcgcagc attttggccc tcagttcccc   2400
atggggacgg tccacacttc ctctcttggc cctgcagacc ttttgtcgtc ggtccgagtc   2460
ggaagaagct cagtcttgag cgcttgagta gcatctacgc gcgaatcact ggacaaagtc   2520
ggcaagacga agccgtcgtc gcctgctgct gctgctgtta ctgcgacagg cgctccgact   2580
gggggcatcg gcataataaa aagatgcccg ccttcgccat ggacctggcc atgagccact   2640
cggcatcggc tctctctctc aacgcttcct ctcacacatc ctccttcatt ccgcccatca   2700
tgcacgtcct gtcgactgcg gtgctgctcg gctccgttgc cgttcaaaag gtcctgggaa   2760
gaccaggatc aagcggtctg tccgacgtca ccaagaggtc tgttgacgac ttcatcagca   2820
ccgagacgcc tattgcactg aacaatcttc tttgcaatgt tggtcctgat ggatgccgtg   2880
cattcggcac atcagctggt gcggtgattg catctcccag cacaattgac ccggactgta   2940
agttggcctt gatgaaccat atcatatatc gccgagaagt ggaccgcgtg ctgagactga   3000
gacagactat tacatgtgga cgcgagatag cgctcttgtc ttcaagaacc tcatcgaccg   3060
cttcaccgaa acgtacgatg cgggcctgca gcgccgcatc gagcagtaca ttactgccca   3120
ggtcactctc cagggcctct ctaacccctc gggctccctc gcggacggct ctggtctcgg   3180
cgagcccaag tttgagttga ccctgaagcc tttcaccggc aactgggggtc gaccgcagcg   3240 ggatggccca gctctgcgag ccattgcctt gattggatac tcaaagtggc tcatcaacaa   3300
caactatcag tcgactgtgt ccaacgtcat ctggcctatt gtgcgcaacg acctcaacta   3360
tgttgcccag tactggtcag tgcttgcttg ctcttgaatt acgtctttgc ttgtgtgtct   3420
aatgcctcca ccacaggaac caaaccggct ttgacctctg ggaagaagtc aatgggagct   3480
cattctttac tgttgccaac cagcaccgag gtatgaagca atcctcgac attcgctgct   3540 actgcacatg agcattgtta ctgaccagct ctacagcact tgtcgagggc gccactcttg   3600
ctgccactct tggccagtcg ggaagcgctt attcatctgt tgctccccag gttttgtgct   3660
ttctccaacg attctgggtg tcgtctggtg gatacgtcga ctccaacagt atgtcttttc   3720
actgtttata tgagattggc caatactgat agctcgcctc tagtcaacac caacgagggc   3780
aggactggca aggatgtcaa ctccgtcctg acttccatcc acaccttcga tcccaacctt   3840
ggctgtgacg caggcacctt ccagccatgc agtgacaaag cgctctccaa cctcaaggtt   3900
gttgtcgact ccttccgctc catctacggc gtgaacaagg gcattcctgc cggtgctgcc   3960
gtcgccattg gccggtatgc agaggatgtg tactacaacg gcaacccttg gtatcttgct   4020
acatttgctg ctgccgagca gctgtacgat gccatctacg tctggaagaa gacgggctcc   4080
atcacggtga ccgccacctc cctggccttc ttccaggagc ttgttcctgg cgtgacggcc   4140
```

```
gggacctact ccagcagctc ttcgaccttt accaacatca tcaacgccgt ctcgacatac      4200
gccgatggct tcctcagcga ggctgccaag tacgtccccg ccgacggttc gctggccgag      4260
cagtttgacc gcaacagcgg cactccgctg tctgcgcttc acctgacgtg gtcgtacgcc      4320
tcgttcttga cagccacggc ccgtcgggct ggcatcgtgc cccctcgtg ggccaacagc       4380 agcgctagca cgatcccctc gacgtgctcc ggcgcgtccg tggtcggatc ctactcgcgt      4440
cccaccgcca cgtcattccc tccgtcgcag acgcccaagc ctggcgtgcc ttccggtact      4500
ccctacacgc ccctgccctg cgcgaccca acctccgtgg ccgtcacctt ccacgagctc       4560
gtgtcgacac agtttggcca gacggtcaag gtggcgggca acgccgcggc cctgggcaac      4620
tggagcacga gcgccgccgt ggctctggac gccgtcaact atgccgataa ccacccctg      4680 tggattggga cggtcaacct cgaggctgga gacgtcgtgg agtacaagta catcaatgtg      4740
ggccaagatg gctccgtgac ctgggagagt gatcccaacc acacttacac ggttcctgcg      4800
gtggcttgtg tgacgcaggt tgtcaaggag gacacctggc agtcgtaatg aatcggcaag      4860
gggtagtact agtagacttg tagtctgcc                                       4889

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
gactgtctcc accatgtaat ttttc                                           25

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
ggcagactac aagtctacta gtactac                                         27

<210> SEQ ID NO 25
<211> LENGTH: 20
<212> TYPE: DNA
<213> ORGANISM: Trichoderma reesei

<400> SEQUENCE: 25
tcctgacttc catccacacc                                                 20

<210> SEQ ID NO 26
<211> LENGTH: 511
<212> TYPE: DNA
<213> ORGANISM: Trichoderma reesei

<400> SEQUENCE: 26
gagcacatgc agtaacgccg actcggcgtc atttcgccac acccaatttg gacctgaggg      60
atgctggaag ctgctgagca gatcccgtta ccgattcatg gcactactac atccatacgc     120
agcaaacatg ggcttgggct tggcttctca atgcaaaatt gcccgcaaaa gtcccggcat     180
tgtcgatgca gagatgcaga tttcagcggg cgattctagg gtaggcgac tactactact      240 aataccacct agtcagtatg tatctagcac cggaggctag gcggttagtg gacgggaacc     300
tggtcattcc atcgcaacca ggatcccgca cttcgttgcg cttctgcccc cacggggcgg     360
```

```
gagttggcag aggcagaatg cggagcagcc ccttgtctgc cctggccggg gcctgttgaa    420
gcaagcagac gagagcagag cggttgagaa gcggtggttg acgcttgacg gtacgaagac    480
gagcgagaat cccgttaagc cgaggctggg c                                   511
```

```
<210> SEQ ID NO 27
<211> LENGTH: 114
<212> TYPE: DNA
<213> ORGANISM: Artificial Sequence
<220> FEATURE:
<223> OTHER INFORMATION: Synthetic construct

<400> SEQUENCE: 27
```

```
taatacgact cactataggg tgtggatgga agtcaggagt tttagagcta gaaatagcaa     60
gttaaaataa ggctagtccg ttatcaactt gaaaaagtgg caccgagtcg gtgc          114
```

```
<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
```

```
cttttttacgg ttcctggc                                                  18
```

```
<210> SEQ ID NO 29
<211> LENGTH: 16
<212> TYPE: DNA
<213> ORGANISM: Artificial Sequence
<220> FEATURE:
<223> OTHER INFORMATION: primer

<400> SEQUENCE: 29
```

```
aaaagcaccg actcgg                                                     16
```

```
<210> SEQ ID NO 30
<211> LENGTH: 2240
<212> TYPE: DNA
<213> ORGANISM: Artificial Sequence
<220> FEATURE:
<223> OTHER INFORMATION: Synthetic construct

<400> SEQUENCE: 30
```

```
ctcgagttta aagtgacaa catgctctca aagcgctcat ggctggcaca agcctggaaa     60
gaaccaacac aaagcatact gcagcaaatc agctgaattc gtcaccaatt aagtgaacat    120
caacctgaag gcagagtatg aggccagaag cacatctgga tcgcagatca tggattgccc    180
ctcttgttga agatgagaat ctagaaagat ggcggggtat gagataagag cgatgggggg    240
gcacatcatc ttccaagaca aacaacccttt gcagagtcag gcaatttttc gtataagagc    300
aggaggaggg agtccagtca tttcatcagc ggtaaaatca ctctagacaa tcttcaagat    360
gagttctgcc ttgggtgact tatagccatc atcataccta gacagaagct tgtgggatac    420
taagaccaac gtacaagctc gcactgtacg ctttgacttc catgtgaaaa ctcgatacgg    480
cgcgcctcta aattttatag ctcaaccact ccaatccaac ctctgcatcc ctctcactcg    540
tcctgatcta ctgttcaaat cagagaataa ggacactatc caaatccaac agaatggcta    600
ccacctccca gctgcctgcc tacaagcagg acttcctcaa atccgccatc gacgcggcg    660 tcctcaagtt tggcagcttc gagctcaagt ccaagcggat atccccctac ttcttcaacg    720
```

```
cgggcgaatt ccacacggcg cgcctcgccg gcgccatcgc ctccgccttt gcaaagacca    780
tcatcgaggc ccaggagaag gccggcctag agttcgacat cgtcttcggc ccggcctaca    840
agggcatccc gctgtgctcc gccatcacca tcaagctcgg cgagctggcg ccccagaacc    900
tggaccgcgt ctcctactcg tttgaccgca aggaggccaa ggaccacggc gagggcggca    960
acatcgtcgg cgcttcgctc aagggcaaga gggtcctgat tgtcgacgac gtcatcaccg   1020
ccggcaccgc caagagggac gccattgaga agatcaccaa ggagggcggc atcgtcgccg   1080
gcatcgtcgt ggccctggac cgcatggaga agctccccgc tgcggatggc gacgactcca   1140
agcctggacc gagtgccatt ggcgagctga ggaaggagta cggcatcccc atctttgcca   1200
tcctcactct ggatgacatt atcgatggca tgaagggctt tgctacccct gaggatatca   1260
agaacacgga ggattaccgt gccaagtaca aggcgactga ctgattgagg cgttcaatgt   1320
cagaagggag agaaagactg aaaaggtgga agaagaggc aaattgttgt tattattatt   1380
attctatctc gaatcttcta gatcttgtcg taaataaaca agcgtaacta gctagcctcc   1440
gtacaactgc ttgaatttga tacccgtatg gagggcagtt attttatttt gttttttcaag   1500
attttccatt cgccgttgaa ctcgtctcac atcgcgtgta ttgcccggtt gccatgtgt    1560
tctcctacta ccccaagtcc ctcacggggtt gtctcacttt ctttctcctt tatcctccct   1620
attttttttc aagtcagcga cagagcagtc atatggggat acgtgcaact gggactcaca   1680
acaggccatc ttatggccta atagccgcg ttggatccac tagtcaattg agcacatgca   1740
gtaacgccga ctcggcgtca tttcgccaca cccaatttgg acctgaggga tgctggaagc   1800
tgctgagcag atcccgttac cgattcatgg cactactaca tccatacgca gcaaacatgg   1860
gcttgggctt ggcttctcaa tgcaaaattg cccgcaaaag tcccggcatt gtcgatgcag   1920
agatgcagat ttcagcgggc gattctaggg tagggcgact actactacta ataccaccta   1980
gtcagtatgt atctagcacc ggaggctagg cggttagtgg acgggaacct ggtcattcca   2040
tcgcaaccag gatcccgcac ttcgttgcgc ttctgccccc acggggcggg agttggcaga   2100
ggcagaatgc ggagcagccc cttgtctgcc ctggccgggg cctgttgaag caagcagacg   2160
agagcagagc ggttgagaag cggtggttga cgcttgacgg tacgaagacg agcgagaatc   2220
ccgttaagcc gaggctgggc                                               2240
```

<210> SEQ ID NO 31
<211> LENGTH: 593
<212> TYPE: DNA
<213> ORGANISM: Trichoderma reesei

<400> SEQUENCE: 31

```
ctcgagttta taagtgacaa catgctctca aagcgctcat ggctggcaca agcctggaaa     60
gaaccaacac aaagcatact gcagcaaatc agctgaattc gtcaccaatt aagtgaacat    120
caacctgaag gcagagtatg aggccagaag cacatctgga tcgcagatca tggattgccc    180
ctcttgttga agatgagaat ctagaaagat ggcggggtat gagataagag cgatgggggg    240
gcacatcatc ttccaagaca aacaaccttt gcagagtcag gcaattttc gtataagagc     300
aggaggaggg agtccagtca tttcatcagc ggtaaaatca ctctagacaa tcttcaagat    360
gagttctgcc ttgggtgact tatagccatc atcataccta gacagaagct tgtgggatac    420
taagaccaac gtacaagctc gcactgtacg ctttgacttc catgtgaaaa ctcgatacgg    480
cgcgcctcta aatttttatag ctcaaccact ccaatccaac ctctgcatcc ctctcactcg    540
tcctgatcta ctgttcaaat cagagaataa ggacactatc caaatccaac aga           593
```

<210> SEQ ID NO 32
<211> LENGTH: 711
<212> TYPE: DNA
<213> ORGANISM: Trichoderma reesei

<400> SEQUENCE: 32

```
atggctacca cctcccagct gcctgcctac aagcaggact tcctcaaatc cgccatcgac      60
ggcggcgtcc tcaagtttgg cagcttcgag ctcaagtcca gcggatatc ccctacttc      120
ttcaacgcgg gcgaattcca cacggcgcgc ctcgccggcg ccatcgcctc cgcctttgca      180
aagaccatca tcgaggccca ggagaaggcc ggcctagagt tcgacatcgt cttcggcccg      240
gcctacaagg gcatcccgct gtgctccgcc atcaccatca agctcggcga gctggcgccc      300
cagaacctgg accgcgtctc ctactcgttt gaccgcaagg aggccaagga ccacggcgag      360
ggcggcaaca tcgtcggcgc ttcgctcaag gcaagaggg tcctgattgt cgacgacgtc      420
atcaccgccg gcaccgccaa gagggacgcc attgagaaga tcaccaagga gggcggcatc      480
gtcgccggca tcgtcgtggc cctggaccgc atggagaagc tccccgctgc ggatggcgac      540
gactccaagc ctggaccgag tgccattggc gagctgagga aggagtacgg catccccatc      600
tttgccatcc tcactctgga tgacattatc gatggcatga agggctttgc taccccctgag   660
gatatcaaga acacggagga ttaccgtgcc aagtacaagg cgactgactg a              711
```

<210> SEQ ID NO 33
<211> LENGTH: 426
<212> TYPE: DNA
<213> ORGANISM: Trichoderma reesei

<400> SEQUENCE: 33

```
ttgaggcgtt caatgtcaga agggagagaa agactgaaaa ggtggaaaga agaggcaaat      60
tgttgttatt attattattc tatctcgaat cttctagatc ttgtcgtaaa taaacaagcg     120
taactagcta gcctccgtac aactgcttga atttgatacc cgtatggagg gcagttattt     180
tatttttgttt ttcaagattt tccattcgcc gttgaactcg tctcacatcg cgtgtattgc    240
ccggttgccc atgtgttctc ctactacccc aagtccctca cgggttgtct cactttcttt     300
ctcctttatc ctccctattt tttttcaagt cagcgacaga gcagtcatat ggggatacgt     360
gcaactggga ctcacaacag gccatcttat ggcctaatag ccggcgttgg atccactagt     420
caattg                                                                 426
```

<210> SEQ ID NO 34
<211> LENGTH: 510
<212> TYPE: DNA
<213> ORGANISM: Trichoderma reesei

<400> SEQUENCE: 34

```
agcacatgca gtaacgccga ctcggcgtca tttcgccaca cccaatttgg acctgaggga      60
tgctggaagc tgctgagcag atcccgttac cgattcatgg cactactaca tccatacgca    120
gcaaacatgg gcttgggctt ggcttctcaa tgcaaaattg cccgcaaaag tcccggcatt    180
gtcgatgcag agatgcagat ttcagcgggc gattctaggt tagggcgact actactacta    240
ataccaccta gtcagtatgt atctagcacc ggaggctagg cggttagtgg acgggaacct    300
ggtcattcca tcgcaaccag gatcccgcac ttcgttgcgc ttctgccccc acggggcggg   360
agttggcaga ggcagaatgc ggagcagccc cttgtctgcc ctggccgggg cctgttgaag   420
```

| | |
|---|---|
| caagcagacg agagcagagc ggttgagaag cggtggttga cgcttgacgg tacgaagacg | 480 |
| agcgagaatc ccgttaagcc gaggctgggc | 510 |

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35

| | |
|---|---|
| ggtgtttggt agtagcaatg | 20 |

<210> SEQ ID NO 36
<211> LENGTH: 27
<212> TYPE: DNA
<213> ORGANISM: Artificial Sequence
<220> FEATURE:
<223> OTHER INFORMATION: primer

<400> SEQUENCE: 36

| | |
|---|---|
| ggcagactac aagtctacta gtactac | 27 |

<210> SEQ ID NO 37
<211> LENGTH: 2372
<212> TYPE: DNA
<213> ORGANISM: Trichoderma reesei

<400> SEQUENCE: 37

| | |
|---|---|
| ggtgtttggt agtagcaatg tttgcggtgg cagtttgagc cgagcctcgt cttgggcttc | 60 |
| tgacccaggc aacgccatct gactagctgc gccgaaggaa ggatgattca ttgtacgacg | 120 |
| ccagtcaatg gaatcttcaa gtaaaagccc gacgaaccga ccatgtcaga tatcagaatt | 180 |
| ctcctggctg gtggggttgg ttggagactg cttacggagt cgatgcctcg tgactgtcat | 240 |
| ggccgcgtcc agcctcctgg gactctgtcc gatattatga cacgagtaaa gcctgcatga | 300 |
| tgtcagtttg ctgcgtctca tgtcgagaac aacacacctg gtgctacata ggcaatacta | 360 |
| cctcgtagct tcaaagttga ctgttttgct ttgatgtctt tgatcatgcc catccatccc | 420 |
| ttgtcttgca gtgcatgtgg atctctacgt ccagacgggg agaaagcttg tctgtgataa | 480 |
| agtacgatga tgcattgatg cctgtggcta cggcccttt atccccatcg tcatgcatct | 540 |
| ctatattaat ccaggagact ctcctcctgg catgggtgag tacaagtgac gaggacatgt | 600 |
| agaagcagag ccacgcaacg tcttgacatc tgtacctatt ttgggccaaa aatcgagacc | 660 |
| caccagctcg tcctacctta catgtgaaga tcttagccca caatcctact gttttactag | 720 |
| tattactgca cagctgtcat cacgagtcct cggttgcttg tgaaacccag ctcagctcct | 780 |
| gagcacatgc agtaacgccg actcggcgtc atttcgccac acccaatttg gacctgaggg | 840 |
| atgctggaag ctgctgagca gatcccgtta ccgattcatg gcactactac atccatacgc | 900 |
| agcaaacatg ggcttgggct tggcttctca atgcaaaatt gcccgcaaaa gtcccggcat | 960 |
| tgtcgatgca gagatgcaga tttcagcggg cgattctagg gtagggcgac tactactact | 1020 |
| aataccacct agtcagtatg tatctagcac cggaggctag gcggttagtg gacgggaacc | 1080 |
| tggtcattcc atcgcaacca ggatcccgca cttcgttgcg cttctgcccc cacggggcgg | 1140 |
| gagttggcag aggcagaatg cggagcagcc ccttgtctgc cctggccggg gcctgttgaa | 1200 |
| gcaagcagac gagagcagag cggttgagaa gcggtggttg acgcttgacg gtacgaagac | 1260 |
| gagcgagaat cccgttaagc cgaggctggg ctgacttcca tccacacctt cgatcccaac | 1320 |

-continued

```
cttggctgtg acgcaggcac cttccagcca tgcagtgaca aagcgctctc caacctcaag    1380
gttgttgtcg actccttccg ctccatctac ggcgtgaaca agggcattcc tgccggtgct    1440
gccgtcgcca ttggccggta tgcagaggat gtgtactaca acggcaaccc ttggtatctt    1500
gctacatttg ctgctgccga gcagctgtac gatgccatct acgtctggaa gaagacgggc    1560
tccatcacgg tgaccgccac ctccctggcc ttcttccagg agcttgttcc tggcgtgacg    1620
gccgggacct actccagcag ctcttcgacc tttaccaaca tcatcaacgc cgtctcgaca    1680
tacgccgatg gcttcctcag cgaggctgcc aagtacgtcc ccgccgacgg ttcgctggcc    1740
gagcagtttg accgcaacag cggcactccg ctgtctgcgc ttcacctgac gtggtcgtac    1800
gcctcgttct tgacagccac ggcccgtcgg gctggcatcg tgcccccctc gtgggccaac    1860
agcagcgcta gcacgatccc ctcgacgtgc tccggcgcgt ccgtggtcgg atcctactcg    1920
cgtcccaccg ccacgtcatt ccctccgtcg cagacgccca agcctggcgt gccttccggt    1980
actccctaca cgcccctgcc ctgcgcgacc ccaacctccg tggccgtcac cttccacgag    2040
ctcgtgtcga cacagtttgg ccagacggtc aaggtggcgg caacgccgc ggccctgggc     2100
aactggagca cgagcgccgc cgtggctctg acgccgtca actatgccga taaccacccc     2160
ctgtggattg ggacggtcaa cctcgaggct ggagacgtcg tggagtacaa gtacatcaat    2220
gtgggccaag atggctccgt gacctgggag agtgatccca accacactta cacggttcct    2280
gcggtggctt gtgtgacgca ggttgtcaag gaggacacct ggcagtcgta atgaatcggc    2340
aagggggtagt actagtagac ttgtagtctg cc                                 2372
```

```
<210> SEQ ID NO 38
<211> LENGTH: 1291
<212> TYPE: DNA
<213> ORGANISM: Trichoderma reesei

<400> SEQUENCE: 38
ggtgtttggt agtagcaatg tttgcggtgg cagtttgagc cgagcctcgt cttgggcttc      60
tgacccaggc aacgccatct gactagctgc gccgaaggaa ggatgattca ttgtacgacg     120
ccagtcaatg gaatcttcaa gtaaaagccc gacgaaccga ccatgtcaga tatcagaatt     180
ctcctggctg gtggggttgg ttggagactg cttacggagt cgatgcctcg tgactgtcat     240
ggccgcgtcc agcctcctgg gactctgtcc gatattatga cacgagtaaa gcctgcatga     300
tgtcagtttg ctgcgtctca tgtcgagaac aacacacctg gtgctacata ggcaatacta     360
cctcgtagct tcaaagttga ctgttttgct ttgatgtctt tgatcatgcc catccatccc     420
ttgtcttgca gtgcatgtgg atctctacgt ccagacgggg agaaagcttg tctgtgataa     480
agtacgatga tgcattgatg cctgtggcta cggccctttt atccccatcg tcatgcatct     540
ctatattaat ccaggagact ctcctcctgg catgggtgag tacaagtgac gaggacatgt     600
agaagcagag ccacgcaacg tcttgacatc tgtacctatt tgggccaaa atcgagacc      660
caccagctcg tcctacctta catgtgaaga tcttagccca caatcctact gttttactag     720
tattactgca cagctgtcat cacgagtcct cggttgcttg tgaaacccag ctcagctcct     780
gagcacatgc agtaacgccg actcggcgtc atttcgccac acccaatttg gacctgaggg     840
atgctggaag ctgctgagca gatcccgtta ccgattcatg gcactactac atccatacgc     900
agcaaacatg ggcttgggct tggcttctca atgcaaaatt gcccgcaaaa gtcccggcat     960
tgtcgatgca gagatgcaga tttcagcggg cgattctagg gtagggcgac tactactact    1020
```

```
aataccacct agtcagtatg tatctagcac cggaggctag gcggttagtg gacgggaacc    1080
tggtcattcc atcgcaacca ggatcccgca cttcgttgcg cttctgcccc cacggggcgg    1140
gagttggcag aggcagaatg cggagcagcc ccttgtctgc cctggccggg gcctgttgaa    1200
gcaagcagac gagagcagag cggttgagaa gcggtggttg acgcttgacg gtacgaagac    1260
gagcgagaat cccgttaagc cgaggctggg c                                   1291

<210> SEQ ID NO 39
<211> LENGTH: 41
<212> TYPE: DNA
<213> ORGANISM: Trichoderma reesei

<400> SEQUENCE: 39
tgaatcggca aggggtagta ctagtagact tgtagtctgc c                         41

<210> SEQ ID NO 40
<211> LENGTH: 1040
<212> TYPE: DNA
<213> ORGANISM: Trichoderma reesei

<400> SEQUENCE: 40
tgacttccat ccacaccttc gatcccaacc ttggctgtga cgcaggcacc ttccagccat      60
gcagtgacaa agcgctctcc aacctcaagg ttgttgtcga ctccttccgc tccatctacg     120
gcgtgaacaa gggcattcct gccggtgctg ccgtcgccat tggccggtat gcagaggatg     180
tgtactacaa cggcaaccct tggtatcttg ctacatttgc tgctgccgag cagctgtacg     240
atgccatcta cgtctggaag aagacgggct ccatcacggt gaccgccacc tccctggcct     300
tcttccagga gcttgttcct ggcgtgacgg ccgggaccta ctccagcagc tcttcgacct     360
ttaccaacat catcaacgcc gtctcgacat acgccgatgg cttcctcagc gaggctgcca     420
agtacgtccc cgccgacggt tcgctggccg agcagtttga ccgcaacagc ggcactccgc     480
tgtctgcgct tcacctgacg tggtcgtacg cctcgttctt gacagccacg gcccgtcggg     540
ctggcatcgt gccccctcg tgggccaaca gcagcgctag cacgatcccc tcgacgtgct     600
ccggcgcgtc cgtggtcgga tcctactcgc gtcccaccgc cacgtcattc cctccgtcgc     660
agacgcccaa gcctggcgtg ccttccggta ctccctacac gccccctgccc tgcgcgaccc     720 caacctccgt ggccgtcacc ttccacgagc tcgtgtcgac acagtttggc cagacggtca     780
aggtggcggg caacgccgcg gccctgggca actggagcac gagcgccgcc gtggctctgg     840
acgccgtcaa ctatgccgat aaccacccc tgtggattgg gacggtcaac ctcgaggctg     900
gagacgtcgt ggagtacaag tacatcaatg tgggccaaga tggctccgtg acctgggaga     960
gtgatcccaa ccacacttac acggttcctg cggtggcttg tgtgacgcag gttgtcaagg    1020
aggacacctg gcagtcgtaa                                                1040

<210> SEQ ID NO 41
<211> LENGTH: 510
<212> TYPE: DNA
<213> ORGANISM: Trichoderma reesei

<400> SEQUENCE: 41
agcacatgca gtaacgccga ctcggcgtca tttcgccaca cccaatttgg acctgaggga     60
tgctggaagc tgctgagcag atcccgttac cgattcatgg cactactaca tccatacgca    120
gcaaacatgg gcttgggctt ggcttctcaa tgcaaaattg cccgcaaaag tcccggcatt    180
gtcgatgcag agatgcagat ttcagcgggc gattctaggg tagggcgact actactacta    240
```

-continued

```
ataccaccta gtcagtatgt atctagcacc ggaggctagg cggttagtgg acgggaacct    300
ggtcattcca tcgcaaccag gatcccgcac ttcgttgcgc ttctgccccc acggggcggg    360
agttggcaga ggcagaatgc ggagcagccc cttgtctgcc ctggccgggg cctgttgaag    420
caagcagacg agagcagagc ggttgagaag cggtggttga cgcttgacgg tacgaagacg    480
agcgagaatc ccgttaagcc gaggctgggc                                     510
```

FUNGAL GENOME MODIFICATION SYSTEMS AND METHODS OF USE

CROSS-REFERENCE TO RELATED APPLICATIONS

The present application claims priority to PCT Patent Appln. Ser. Nos. PCT/CN2014/093916, PCT/CN2014/093914, and PCT/CN2014/093918, all filed Dec. 16, 2014, which are hereby incorporated by reference in their entireties.

SEQUENCE LISTING

The sequence listing submitted via EFS, in compliance with 37 C.F.R. § 1.52(e), is incorporated herein by reference. The sequence listing text file submitted via EFS contains the file "40532-WO-PCT-5(2015-831)_ST25.txt" created on Dec. 11, 2015, which is 146 kilobytes in size.

BACKGROUND

Bacteria and archaea have evolved adaptive immune defenses termed clustered regularly interspaced short palindromic repeats (CRISPR)/CRISPR-associated (Cas) systems that can introduce double strand beaks in DNA in a sequence-specific manner. Cas systems perform their functions through the activity of a ribonucleoprotein complex that includes short RNA sequences (tracrRNA and crRNA) and an RNA dependent endonuclease (Cas endonuclease) that targets a specific DNA sequence (through homology to a portion of the crRNA, called the variable targeting domain) and generates double strand breaks in the target. CRISPR loci were first recognized in *E. coli* (Ishino et al. (1987) J. Bacteriol. 169:5429-5433; Nakata et al. (1989) J. Bacteriol. 171:3553-3556), with similar interspersed short sequence repeats being subsequently identified in a number of bacterial species, including but not limited to *Haloferax mediterranei, Streptococcus pyogenes, Anabaena*, and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307:26-30; Mojica et al. (1995) Mol. Microbiol. 17:85-93).

It is well known that inducing cleavage at a specific target site in genomic DNA can be used to introduce modifications at or near that site. For example, homologous recombination for gene targeting has been shown to be enhanced when the targeted DNA site contains a double-strand break (see, e.g., Rudin et al., Genetics 122:519-534; Smih et al., Nucl. Acids Res. 23:5012-5019). Given the site-specific nature of Cas systems, genome modification/engineering technologies based on these systems have been described, including in mammalian cells (see, e.g., Hsu et al.; Cell vol. 157, p 1262-1278, 5 Jun. 2014 entitled "Development and Applications of CRISPR-Cas9 for Genome Engineering"). The power of the Cas-based genome engineering comes from the ability to target virtually any specific location within a complex genome by designing a recombinant crRNA (or equivalently functional polynucleotide) in which the DNA-targeting region (variable targeting domain) of the crRNA is homologous to the desired target site in the genome and combining it with a Cas endonuclease (through any convenient means) into a functional complex in a host cell.

Although Cas-based genome engineering technologies have been applied to a number of different host cell types, the efficient use of such systems in fungal cells has proven to be difficult. Thus, there still remains a need for developing efficient and effective Cas-based genome engineering methods and compositions for modifying/altering a genomic target site in a fungal cell.

BRIEF SUMMARY

Compositions and methods are provided that relate to employing a guide RNA/Cas endonuclease system for inserting a donor DNA at a target site in the genome of a fungal cell, e.g., a filamentous fungal cell.

Aspects of the present disclosure are drawn to methods for inserting a donor DNA at a target site in the genome of a fungal cell. In some embodiments, the method includes: a) introducing into a population of fungal cells a Cas endonuclease, a guide RNA, and a donor DNA, wherein the Cas endonuclease and guide RNA are capable of forming a complex that enables the Cas endonuclease to introduce a double-strand break at a target site in a genomic locus of the genome of the fungal cells; and b) identifying at least one fungal cell from the population in which insertion of the donor DNA at the target site in the genomic locus has occurred, where the Cas endonuclease, the guide RNA, or both are introduced transiently into the population of fungal cells.

In certain embodiments, the insertion has not occurred via a homologous recombination between the donor DNA and the genome of the fungal cells.

In certain embodiments, the donor DNA does not comprise a sequence homologous to a genomic sequence in the genomic locus. In some embodiments, the donor DNA does not comprise a sequence that is homologous to a genomic sequence over at least 150, 200, 250, 300, 350, 400, 450, or 500 nucleotides length. In some embodiments, the donor DNA does not comprise a sequence that is homologous to a genomic sequence over at least 200 nucleotides length.

In certain embodiments, the insertion of the donor DNA interrupts the expression or function of the genomic locus. In certain other embodiments, the insertion does not interrupt the expression or function of the genomic locus.

In some embodiments of the method, the donor DNA comprises a gene of interest. In certain embodiments, the donor DNA comprises an expression cassette encoding a gene product of interest.

In some embodiments, the gene of interest or the expression cassette encodes a protein of interest. In certain embodiments, the protein of interest is an enzyme. In particular embodiments, the protein of interest is a hemicellulase, a peroxidase, a protease, a cellulase, a xylanase, a lipase, a phospholipase, an esterase, a cutinase, a pectinase, a keratinase, a reductase, an oxidase, a phenol oxidase, a lipoxygenase, a ligninase, a pullulanase, a tannase, a pentosanase, a mannanase, a beta-glucanase, an arabinosidase, a hyaluronidase, a chondroitinase, a laccase, an amylase, a glucoamylase, a variant thereof, a functional fragment thereof, or a hybrid or mixture of two or more thereof. In yet other particular embodiments, the protein of interest is a peptide hormone, a growth factor, a clotting factor, a chemokine, a cytokine, a lymphokine, an antibody, a receptor, an adhesion molecule, a microbial antigen, a variant thereof, a functional fragment thereof, or a hybrid or mixture of two or more thereof.

In certain embodiments, the gene of interest or the expression cassette encodes a phenotypic marker, e.g., a detectable marker, a selectable marker, a dominant heterologous selectable marker, a reporter gene, an auxotrophic marker, an antibiotic resistance marker, etc. (see description below). Any convenient phenotypic marker may be used.

In some embodiments of the method, the donor DNA comprises, or further comprises (e.g., in the embodiments where the donor DNA comprises a gene of interest or an expression cassette), a sequence homologous to a genomic sequence in the genomic locus (sometimes referred to herein as a "repeat sequence"), but the repeat sequence is not used for insertion of the donor DNA at the target site in the genomic locus. In some embodiments, the repeat sequence is at least about 150, 200, 300, 400, or 500 nucleotides long. In certain embodiments, the genomic sequence (i.e., the sequence to which the repeat sequence in the donor DNA is homologous) and the target site flank a genomic deletion target region. The genomic deletion target region is one defined by the user. In certain embodiments, the insertion of the donor DNA results in the genomic sequence and the sequence homologous to the genomic sequence (comprised in the donor DNA) flanking a loop-out target region comprising the genomic deletion target region. The genomic sequence and the sequence homologous to the genomic sequence are sometimes both referred to as the "repeat sequences" herein. In some embodiments where the donor DNA comprises an expression cassette encoding a phenotypic marker, the genomic sequence and the sequence homologous to the genomic sequence flank a loop-out target region that includes the genomic deletion target region and the phenotypic marker, e.g., a selectable marker. (See FIG. 1 for a schematic diagram showing examples of the donor DNA and genomic locus structural features).

In certain embodiments, the method is one that results in the deletion of a genomic sequence (a genomic deletion target region) from the genome of the fungal cell. In such aspects of the present disclosure, the method further includes: c) culturing the fungal cell having the donor DNA inserted at the target site under conditions that promote or allow loop-out of the loop-out target region (i.e., the region between the genomic sequence and the repeat sequence in the donor DNA that is homologous to the genomic sequence), and d) identifying at least one fungal cell in the culture in which loop-out of the loop-out target region has occurred. This can be achieved by culturing the fungal cell under conditions in which only fungal cells that have lost the selectable marker can grow because the selectable marker is part of the loop-out target region.

Another aspect of the present disclosure is drawn to a method for deleting a target region in the genome of a fungal cell, the method comprising: a) introducing into a population of fungal cells a Cas endonuclease, a guide RNA, and a donor DNA, wherein the Cas endonuclease and guide RNA are capable of forming a complex that enables the Cas endonuclease to introduce a double-strand break at a target site in the genome of the fungal cells and allowing the donor DNA to be inserted at the target cite, wherein the donor DNA comprises a sequence homologous to a genomic sequence of the fungal cells, and wherein the genomic sequence and the target site flank the target region in the fungal cell genome; b) culturing the population of fungal cells under conditions that allow homologous recombination between the genomic sequence and the sequence homologous to the genomic sequence; and c) identifying at least one fungal cell in the culture in which deletion of the target region has occurred; wherein the Cas endonuclease, the guide RNA, or both are introduced transiently into the population of fungal cells. The sequence on the donor DNA homologous to the genomic sequence of the fungal cells is sometimes referred to herein as a "repeat sequence". In some embodiments, the repeat sequence is not used for insertion of the donor DNA at the target site in the genomic locus. In some embodiments, the repeat sequence is at least about 150, 200, 300, 400, or 500 nucleotides long.

In certain embodiments of the method of deleting a target region in the genome of a fungal cell, the method further comprises, between steps a) and b), a step of identifying at least one fungal cell from the population in which insertion of the donor DNA at the target site has occurred. In some embodiments of the method, the donor DNA is not inserted at the target site via a homologous recombination between the donor DNA and the fungal cell genome.

In certain embodiments of the methods described herein, the Cas endonuclease is a Type II Cas9 endonuclease or variant thereof. In some embodiments, the Cas9 endonuclease or variant thereof comprises a full length Cas9 or a functional fragment thereof from a species selected from the group consisting of: *Streptococcus* sp., *S. pyogenes*, *S. mutans*, *S. thermophilus*, *Campylobacter* sp., *C. jejuni*, *Neisseria* sp., *N. meningitides*, *Francisella* sp., *F. novicida*, *Pasteurella* sp., and *P. multocida*. In specific embodiments, Cas9 endonucleases or variants thereof containing an amino acid sequence that has at least 70% identity to any one of SEQ ID NOs:1 to 7 may be employed, e.g., at least 80% identity, at least 90% identity, at least 95% identity, at least 96% identity, at least 97% identity, at least 98% identity, at least 99% identity, and including up to 100% identity to any one of SEQ ID NOs:1 to 7. In other embodiments, the Cas endonuclease or variant thereof is a Cpf1 endonuclease of the Type II CRISPR-Cas system.

In certain embodiments, introducing the Cas endonuclease and/or the guide RNA into the fungal cells includes introducing one or more DNA constructs comprising expressions cassettes for the Cas endonuclease, the guide RNA, or both into the fungal cells. The one or more DNA constructs, once in the fungal cells, express the Cas endonuclease and/or the guide RNA.

In certain embodiments, the introducing step includes directly introducing a Cas endonuclease polypeptide, a guide RNA, or both into the fungal cells. Any combination of direct introduction and using DNA constructs can be employed (e.g., introducing a DNA construct with an expression cassette for a Cas endonuclease into the fungal cell and directly introducing a guide RNA into the cell, either simultaneously or sequentially as desired).

In certain embodiments of the methods described herein, the Cas expression cassette in the DNA construct includes a Cas endonuclease encoding gene that is optimized for expression in the fungal cell. For example, a Cas endonuclease encoding gene that is optimized for expression in filamentous fungal cells includes a sequence that has at least 70% sequence identity to SEQ ID NO:8 (encoding Cas9 from *S. pyogenes*; SEQ ID NO:1).

In some instances, the Cas endonuclease is operably linked to one or more nuclear targeting signal (also referred to as a nuclear localization signal/sequence; NLS). SEQ ID NO:9 and SEQ ID NO:10 provide an example of a filamentous fungal cell optimized Cas9 gene with NLS sequences at the N- and C-termini and the encoded amino acid sequence, respectively. Many different NLSs are known in eukaryotes. They include monopartite, bipartite and tripartite types. Any convenient NLS can be used, the monopartite type being somewhat more convenient with examples including the SV40 NLS, a NLS derived from the *T. reesei* blr2 (blue light regulator 2) gene, or a combination of both.

In certain embodiments, the expression cassette for the guide RNA comprises a DNA polymerase III dependent promoter functional in a Euascomycete or Pezizomycete, the promoter operably linked to the DNA encoding the guide RNA. In some instances, the promoter is derived from a *Trichoderma* U6 snRNA gene. In some embodiments, the promoter comprises a nucleotide sequence with at least 60%, 65%, 70%, 75%, 80%, 85%, 90%, 95%, 96%, 97%, 98%, or 99% identity to SEQ ID NO: 11 or 12. In some embodiments, the promoter comprises the sequence of SEQ ID NO: 11 or 12. In certain embodiments, the DNA encoding the guide RNA comprises an intron sequence from a *Trichoderma* U6 snRNA gene.

Fungal cells that find use in the subject methods can be filamentous fungal cells. In some embodiments, the fungal cell is a Eumycotina or Pezizomycotina fungal cell. In certain embodiments, the fungal cell is a species selected from the group consisting of *Trichoderma, Penicillium, Aspergillus, Humicola, Chrysosporium, Fusarium, Neurospora, Myceliophthora, Thermomyces, Hypocrea,* and *Emericella*. In some embodiments, the filamentous fungal cell is selected from *Trichoderma reesei, P. chrysogenum, M. thermophila, Thermomyces lanuginosus, A. oryzae* and *A. niger*. Other fungal cells, including species of yeast, can also be employed.

The target site selected by a user of the disclosed methods can be located within a region of a gene of interest selected from the group consisting of: an open reading frame, a promoter, a regulatory sequence, a terminator sequence, a regulatory element sequence, a splice site, a coding sequence, a polyubiquitination site, an intron site, and an intron enhancing motif. Examples of genes of interest include genes encoding acetyl esterases, aminopeptidases, amylases, arabinases, arabinofuranosidases, carboxypeptidases, catalases, cellulases, chitinases, cutinase, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, transferases, transport proteins, transglutaminases, xylanases, hexose oxidases, and combinations thereof. Target genes encoding regulatory proteins such as a transcription factor, a repressor, protein that modifies other proteins such as kinases, proteins involved in post-translational modification (e.g., glycosylation) can be subjected to Cas mediated editing as well as genes involved in cell signaling, morphology, growth rate, and protein secretion. No limitation in this regard is intended.

In some embodiments of the methods, the step of identifying a fungal cell having a genomic modification at the site of interest includes culturing the population of cells from step (a) under conditions to select for or screen for the modification at the target site. Such conditions include antibiotic selection conditions, conditions that select for or screen for auxotrophic cells, and the like.

Aspects of the present disclosure are drawn to recombinant fungal cells produced by the methods described above as well as those for use as parental host cells in performing the methods.

Additional embodiments of the methods and compositions of the present disclosure are shown herein.

BRIEF DESCRIPTION OF THE DRAWINGS

The disclosure can be more fully understood from the following detailed description and the accompanying drawings, which form a part of this application.

DETAILED DESCRIPTION

Figure 1:
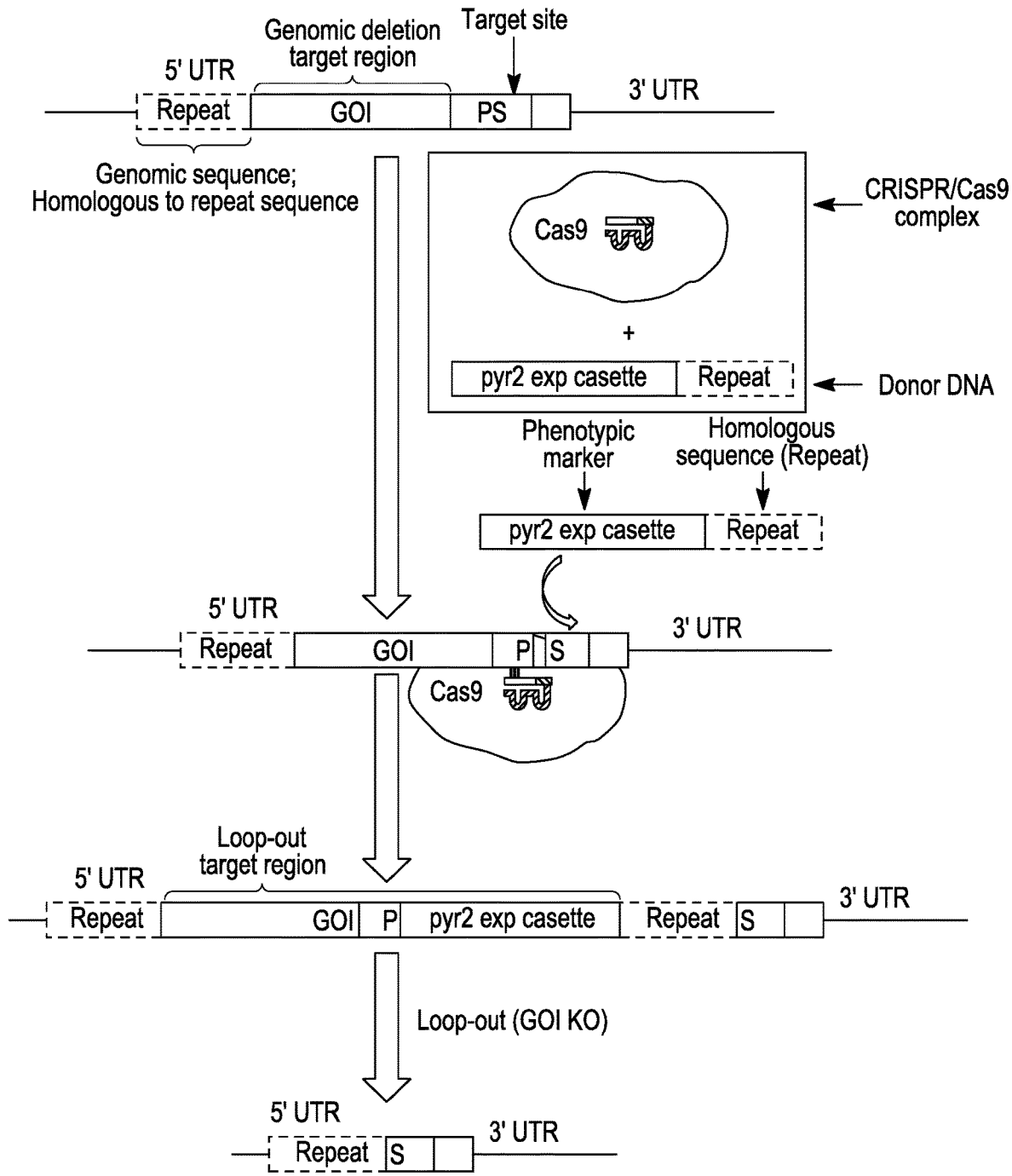
FIG. 1. Work flow of the application of pure SpyCas9 mediated DNA insertion for gene deletion in *T. reesei*.

The present disclosure includes compositions and methods that find use in inserting a donor DNA at a target site in the genome of a fungal cell. The methods employ a functional guide RNA/Cas endonuclease complex which recognizes a desired target site and introduces a double strand break at the site, which thereby allows insertion of a donor DNA at the target site.

Before the present compositions and methods are described in greater detail, it is to be understood that the present compositions and methods are not limited to particular embodiments described, and as such may, of course, vary. It is also to be understood that the terminology used herein is for the purpose of describing particular embodiments only, and is not intended to be limiting, since the scope of the present compositions and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present compositions and methods are not entitled to antedate such publication by virtue of prior invention. Further, the dates of publication provided may be different from the actual publication dates which may need to be independently confirmed.

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

Definitions

As used herein, a polypeptide referred to as a "Cas endonuclease" or having "Cas endonuclease activity" relates to a CRISPR associated (Cas) polypeptide encoded by a Cas gene where the Cas protein is capable of cutting a target DNA sequence when functionally coupled with one or more guide polynucleotides (see, e.g., U.S. Pat. No. 8,697,359 entitled "CRISPR-Cas systems and methods for altering expression of gene products"). Variants of Cas endonucleases that retain guide polynucleotide directed endonuclease activity are also included in this definition. The Cas endonucleases employed in the donor DNA insertion methods detailed herein are endonucleases that introduce double-strand breaks into the DNA at the target site. A Cas endonuclease is guided by the guide polynucleotide to recognize and cleave a specific target site in double stranded DNA, e.g., at a target site in the genome of a cell. Several different types of CRISPR-Cas systems have been described and can be classified as Type I, Type II, and Type III CRISPR-Cas systems (see, e.g., the description in Liu and Fan, CRISPR-Cas system: a powerful tool for genome editing. Plant Mol Biol (2014) 85:209-218). In certain embodiments, the Cas endonuclease or variant thereof is a Cas9 endonuclease of the Type II CRISPR-Cas system. The Cas9 endonuclease may be any convenient Cas9 endonuclease, including but not limited to Cas9 endonucleases, and functional fragments thereof, from the following bacterial species: *Streptococcus* sp. (e.g., *S. pyogenes, S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*). Numerous other species of Cas9 can be used. For example, functional Cas9 endonucleases or variants thereof containing an amino acid sequence that has at least 70% identity to any one of SEQ ID NOs:1 to 7 may be employed, e.g., at least 80% identity, at least 90% identity, at least 95% identity, at least 96% identity, at least 97% identity, at least 98% identity, at least 99% identity, and including up to 100% identity to any one of SEQ ID NOs:1 to 7. In other embodiments, the Cas endonuclease or variant thereof is a Cpf1 endonuclease of the Type II CRISPR-Cas system. Cpf1 mediates robust DNA interference with features distinct from Cas9. Cpf1 lacks tracrRNA and utilizes a T-rich protospacer-adjacent motif. It cleaves DNA via a staggered DNA double-stranded break. See, e.g., Zetsche et al., Cell (2015) 163:759-771.

As used herein, the term "guide polynucleotide" relates to a polynucleotide sequence that can form a complex with a Cas endonuclease and enables the Cas endonuclease to recognize and cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. In one embodiment, the size of the fragment of the crRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides). In certain embodiments, the RNA that guides the RNA/Cas9 endonuclease complex is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a crRNA or crRNA fragment and a tracrRNA or tracrRNA fragment of the type II CRISPR/Cas system that can form a complex with a type II Cas endonuclease, wherein the guide RNA/Cas endonuclease complex can direct the Cas endonuclease to a fungal cell genomic target site, enabling the Cas endonuclease to introduce a double strand break into the genomic target site.

One aspect of using a single guide polynucleotide versus a duplex guide polynucleotide is that only one expression cassette needs to be made to express the single guide polynucleotide in a target cell.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence is at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or is 100% complementary. The VT domain can be at least 12, 13, 14, 15, 16, 17, 18, 19, 20, 21, 22, 23, 24, 25, 26, 27, 28, 29 or 30 nucleotides in length. In some embodiments, the VT domain comprises a contiguous stretch of 12 to 30 nucleotides. The VT domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

As used herein, the term "guide polynucleotide/Cas endonuclease system" (and equivalents) includes a complex of a Cas endonuclease and a guide polynucleotide (single or double) that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is appropriately oriented at the 3' end of the target sequence.

The terms "functional fragment", "fragment that is functionally equivalent", "functionally equivalent fragment", and the like, are used interchangeably and refer to a portion or subsequence of a parent polypeptide that retains the qualitative enzymatic activity of the parent polypeptide. For example, a functional fragment of a Cas endonuclease retains the ability to create a double-strand break with a guide polynucleotide. It is noted here that a functional fragment may have altered quantitative enzymatic activity as compared to the parent polypeptide.

The terms "functional variant", "variant that is functionally equivalent", "functionally equivalent variant", and the like are used interchangeably and refer to a variant of a parent polypeptide that retains the qualitative enzymatic activity of the parent polypeptide. For example, a functional variant of a Cas endonuclease retains the ability to create a double-strand break with a guide polynucleotide. It is noted here that a functional variant may have altered quantitative enzymatic activity as compared to the parent polypeptide.

Fragments and variants can be obtained via any convenient method, including site-directed mutagenesis and synthetic construction.

The term "genome" as it applies to a fungal cell cells encompasses not only chromosomal DNA found within the nucleus, but organelle DNA found within subcellular components (e.g., mitochondria) of the cell.

A "codon-modified gene" or "codon-preferred gene" or "codon-optimized gene" is a gene having its frequency of codon usage designed to mimic the frequency of preferred codon usage of the host cell. The nucleic acid changes made to codon-optimize a gene are "synonymous", meaning that they do not alter the amino acid sequence of the encoded polypeptide of the parent gene. However, both native and variant genes can be codon-optimized for a particular host cell, and as such no limitation in this regard is intended.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. As is well-known in the art, promoters can be categorized according to their strength and/or the conditions under which they are active, e.g., constitutive promoters, strong promoters, weak promoters, inducible/repressible promoters, tissue-specific/developmentally regulated promoters, cell-cycle dependent promoters, etc.

"RNA transcript" refers to the product resulting from RNA polymerase-catalyzed transcription of a DNA sequence. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. "Sense" RNA refers to RNA transcript that includes the mRNA and can be translated into protein within a cell or in vitro. "Antisense RNA" refers to an RNA transcript that is complementary to all or part of a target primary transcript or mRNA, and that, under certain conditions, blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated into a polypeptide but yet has an effect on cellular processes. The terms "complement" and "reverse complement" are used interchangeably herein with respect to mRNA transcripts, and are meant to define the antisense RNA of the message.

As used herein, "functionally attached" or "operably linked" means that a regulatory region or functional domain of a polypeptide or polynucleotide sequence having a known or desired activity, such as a promoter, enhancer region, terminator, signal sequence, epitope tag, etc., is attached to or linked to a target (e.g., a gene or polypeptide) in such a manner as to allow the regulatory region or functional domain to control the expression, secretion or function of that target according to its known or desired activity. For example, a promoter is operably linked with a coding sequence when it is capable of regulating the expression of that coding sequence (i.e., the coding sequence is under the transcriptional control of the promoter).

Standard recombinant DNA and molecular cloning techniques used herein are well known in the art.

"PCR" or "polymerase chain reaction" is a technique for the synthesis of specific DNA segments and consists of a series of repetitive denaturation, annealing, and extension cycles and is well known in the art.

The term "recombinant," when used in reference to a biological component or composition (e.g., a cell, nucleic acid, polypeptide/enzyme, vector, etc.) indicates that the biological component or composition is in a state that is not found in nature. In other words, the biological component or composition has been modified by human intervention from its natural state. For example, a recombinant cell encompass a cell that expresses one or more genes that are not found in its native parent (i.e., non-recombinant) cell, a cell that expresses one or more native genes in an amount that is different than its native parent cell, and/or a cell that expresses one or more native genes under different conditions than its native parent cell. Recombinant nucleic acids may differ from a native sequence by one or more nucleotides, be operably linked to heterologous sequences (e.g., a heterologous promoter, a sequence encoding a non-native or variant signal sequence, etc.), be devoid of intronic sequences, and/or be in an isolated form. Recombinant polypeptides/enzymes may differ from a native sequence by one or more amino acids, may be fused with heterologous sequences, may be truncated or have internal deletions of amino acids, may be expressed in a manner not found in a native cell (e.g., from a recombinant cell that over-expresses the polypeptide due to the presence in the cell of an expression vector encoding the polypeptide), and/or be in an isolated form. It is emphasized that in some embodiments, a recombinant polynucleotide or polypeptide/enzyme has a sequence that is identical to its wild-type counterpart but is in a non-native form (e.g., in an isolated or enriched form).

The terms "plasmid", "vector" and "cassette" refer to an extra chromosomal element that carries a polynucleotide sequence of interest, e.g., a gene of interest to be expressed in a cell (an "expression vector" or "expression cassette"). Such elements are generally in the form of double-stranded DNA and may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. The polynucleotide sequence of interest may be a gene encoding a polypeptide or functional RNA that is to be expressed in the target cell. Expression cassettes/vectors generally contain a gene with operably linked elements that allow for expression of that gene in a host cell.

The term "expression", as used herein, refers to the production of a functional end-product (e.g., an mRNA, guide RNA, or a protein) in either precursor or mature form.

"Introduced" in the context of inserting a polynucleotide or polypeptide into a cell (e.g., a recombinant DNA construct/expression construct) refers to any method for performing such a task, and includes any means of "transfection", "transformation", "transduction", physical means, or the like, to achieve introduction of the desired biomolecule.

By "introduced transiently", "transiently introduced", "transient introduction", "transiently express" and the like is meant that a biomolecule is introduced into a host cell (or a population of host cells) in a non-permanent manner. With respect to double stranded DNA, transient introduction includes situations in which the introduced DNA does not integrate into the chromosome of the host cell and thus is not transmitted to all daughter cells during growth as well as situations in which an introduced DNA molecule that may have integrated into the chromosome is removed at a desired time using any convenient method (e.g., employing a cre-lox system, by removing positive selective pressure for an episomal DNA construct, by promoting looping out of all or part of the integrated polynucleotide from the chromosome using a selection media, etc.). No limitation in this regard is intended. In general, introduction of RNA (e.g., a guide RNA, a messenger RNA, ribozyme, etc.) or a polypeptide (e.g., a Cas polypeptide) into host cells is considered transient in that these biomolecules are not replicated and indefinitely passed down to daughter cells during cell growth. With respect to the Cas/guide RNA complex, transient introduction covers situations when either of the components is introduced transiently, as both biomolecules are needed to exert targeted Cas endonuclease activity. Thus, transient introduction of a Cas/guide RNA complex includes embodiments where either one or both of the Cas endonuclease and the guide RNA are introduced transiently. For example, a host cell having a genome-integrated expression cassette for the Cas endonuclease (and thus not transiently introduced) into which a guide RNA is transiently introduced can be said to have a transiently introduced Cas/guide RNA complex (or system) because the functional complex is present in the host cell in a transient manner. In certain embodiments, the introducing step includes: (i) obtaining a parental fungal cell population that stably expresses the Cas endonuclease, and (ii) transiently introducing the guide RNA into the parental fungal cell population. Conversely, the introducing step can include: (i) obtaining a parental fungal cell population that stably expresses the guide RNA, and (ii) transiently introducing the Cas endonuclease into the parental fungal cell population.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance (the resulting host cell is sometimes referred to herein as a "stable transformant"). In contrast, "transient transformation" refers to the transfer of a nucleic acid fragment into the nucleus, or other DNA-containing organelle, of a host organism resulting in gene expression without integration or stable inheritance (sometimes referred to herein as "unstable transformation", and the resulting host cell sometimes referred to herein as an "unstable transformant"). Host organisms containing the transformed nucleic acid fragments are referred to as "transgenic" organisms.

"Fungal cell", "fungi", "fungal host cell", and the like, as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., supra) and all mitosporic fungi (Hawksworth et al., supra). In certain embodiments, the fungal host cell is a yeast cell, where by "yeast" is meant ascosporogenous yeast (Endomycetales), basidiosporogenous yeast, and yeast belonging to the Fungi Imperfecti (Blastomycetes). As such, a yeast host cell includes a *Candida, Hansenula, Kluyveromyces, Pichia, Saccharomyces, Schizosaccharomyces*, or *Yarrowia* cell. Species of yeast include, but are not limited to, the following: *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis*, and *Yarrowia lipolytica* cell.

The term "filamentous fungal cell" includes all filamentous forms of the subdivision Eumycotina or Pezizomycotina. Suitable cells of filamentous fungal genera include, but are not limited to, cells of *Acremonium, Aspergillus, Chrysosporium, Corynascus, Chaetomium, Emericella, Fusarium, Gibberella, Humicola, Magnaporthe, Myceliophthora, Neurospora, Paecilomyces, Penicillium, Scytaldium, Talaromyces, Thermoascus, Thielavia, Tolypocladium, Hypocrea*, and *Trichoderma*.

Suitable cells of filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium cul-* morum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Hypocrea jecorina, Myceliophthora thermophila, Neurospora crassa, Neurospora intermedia, Penicillium purpurogenum, Penicillium canescens, Penicillium solitum, Penicillium funiculosum Phanerochaete chrysosporium, Talaromyces flavus, Thielavia terrestris, Trichoderma harzianum, Trichoderma koningii, Trichoderma longibrachiatum, Trichoderma reesei, and Trichoderma viride.

The terms "target site", "target sequence", "genomic target site", "genomic target sequence" (and equivalents) are used interchangeably herein and refer to a polynucleotide sequence in the genome of a fungal cell at which a Cas endonuclease cleavage is desired to promote a genome modification, e.g., insertion of a donor DNA and subsequent deletion of a genomic region of interest. The context in which this term is used, however, can slightly alter its meaning. For example, the target site for a Cas endonuclease is generally very specific and can often be defined to the exact nucleotide position, whereas in some cases the target site for a desired genome modification can be defined more broadly than merely the site at which DNA cleavage occurs, e.g., a genomic locus or region that is to be deleted from the genome. Thus, in certain cases, the genome modification that occurs via the activity of Cas/guide RNA DNA cleavage is described as occurring "at or near" the target site. The target site can be an endogenous site in the fungal cell genome, or alternatively, the target site can be heterologous to the fungal cell and thereby not be naturally occurring in the genome, or the target site can be found in a heterologous genomic location compared to where it occurs in nature.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The term "derived from" encompasses the terms "originated from," "obtained from," "obtainable from," "isolated from," and "created from," and generally indicates that one specified material find its origin in another specified material or has features that can be described with reference to the another specified material.

As used herein, the term "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm−5° C. (5° C. below the Tm of the probe); "high stringency" at about 5-10° C. below the Tm; "intermediate stringency" at about 10-20° C. below the Tm of the probe; and "low stringency" at about 20-25° C. below the Tm. Alternatively, or in addition, hybridization conditions can be based upon the salt or ionic strength conditions of hybridization, and/or upon one or more stringency washes, e.g.: 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

As used herein, the term "hybridization" refers to the process by which a strand of nucleic acid joins with a complementary strand through base pairing, as known in the art. More specifically, "hybridization" refers to the process by which one strand of nucleic acid forms a duplex with, i.e., base pairs with, a complementary strand, as occurs during blot hybridization techniques and PCR techniques. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while intermediate or low stringency hybridization can be used to identify or detect polynucleotide sequence homologs.

Intermediate and high stringency hybridization conditions are well known in the art. For example, intermediate stringency hybridizations may be carried out with an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/mL denatured sheared salmon sperm DNA, followed by washing the filters in 1×SSC at about 37-50° C. High stringency hybridization conditions may be hybridization at 65° C. and 0.1×SSC (where 1×SSC=0.15 M NaCl, 0.015 M Na citrate, pH 7.0). Alternatively, high stringency hybridization conditions can be carried out at about 42° C. in 50% formamide, 5×SSC, 5×Denhardt's solution, 0.5% SDS and 100 μg/mL denatured carrier DNA followed by washing two times in 2×SSC and 0.5% SDS at room temperature and two additional times in 0.1×SSC and 0.5% SDS at 42° C. And very high stringent hybridization conditions may be hybridization at 68° C. and 0.1×SSC. Those of skill in the art know how to adjust the temperature, ionic strength, etc. as necessary to accommodate factors such as probe length and the like.

The phrase "substantially similar" or "substantially identical," in the context of at least two nucleic acids or polypeptides, means that a polynucleotide or polypeptide comprises a sequence that has at least 90%, at least 91%, at least 92%, at least 93%, at least 94%, at least 95%, at least 96%, at least 97%, at least 98%, or even at least 99% identical to a parent or reference sequence, or does not include amino acid substitutions, insertions, deletions, or modifications made only to circumvent the present description without adding functionality.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) CABIOS 5:151-153; Higgins et al., (1992) Comput Appl Biosci 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) CABIOS 5:151-153; Higgins et al., (1992) Comput Appl Biosci 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) Proc. Natl. Acad. Sci. USA 89:10915). GAP uses the algorithm of Needleman and Wunsch, (1970) J Mol Biol 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" includes a nucleic acid fragment that encodes and is capable to express a functional molecule such as, but not limited to, a specific polypeptide (e.g., an enzyme) or a functional RNA molecule (e.g., a guide RNA, an anti-sense RNA, ribozyme, etc.), and includes regulatory sequences preceding (5' non-coding sequences) and/or following (3' non-coding sequences) the coding sequence. "Native gene" refers to a gene as found in nature with its own regulatory sequences. A recombinant gene refers to a gene that is regulated by a different gene's regulatory sequences which could be from a different organism or the same organism.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated fungal cell is a fungal cell comprising a mutated gene.

As used herein, a "targeted mutation" is a mutation in a native gene that was made by altering a target sequence within the native gene using a method involving a double-strand-break-inducing agent that is capable of inducing a double-strand break in the DNA of the target sequence as disclosed herein or known in the art.

The term "donor DNA" or "donor nucleic acid sequence" or "donor polynucleotide" refers to a polynucleotide that contains a polynucleotide sequence of interest that is to be inserted at a target site in the genome of a fungal cell, generally in conjunction with the activity of a Cas/guide polynucleotide complex (where the guide polynucleotide defines the target site, as detailed above). In certain embodiments, the donor DNA construct further comprises a sequence homologous to a genomic sequence in the genomic locus (also called a repeat sequence). By "homologous" is meant DNA sequences that are similar. For example, a "region homologous to a genomic sequence" that is found on the donor DNA is a region of DNA that has a similar sequence to a given "genomic sequence" in the fungal cell genome. Collectively, the sequence homologous to a genomic sequence in the genomic locus and the genomic sequence itself are sometimes referred to herein as "the repeat sequences". A homologous region can be of any length that is sufficient to promote or allow looping-out of the loop-out target region via homologous recombination between the repeat sequence and the homologous genomic sequence (which can be selected for under selective culture conditions). For example, the repeat sequence can comprise at least 50-55, 50-60, 50-65, 50-70, 50-75, 50-80, 50-85, 50-90, 50-95, 50-100, 50-200, 50-300, 50-400, 50-500, 50-600, 50-700, 50-800, 50-900, 50-1000, 50-1100, 50-1200, 50-1300, 50-1400, 50-1500, 50-1600, 50-1700, 50-1800, 50-1900, 50-2000, 50-2100, 50-2200, 50-2300, 50-2400, 50-2500, 50-2600, 50-2700, 50-2800, 50-2900, 50-3000, 50-3100 or more bases in length. "Sufficient homology" indicates that two polynucleotide sequences (e.g., direct repeat sequences in the donor DNA and the genome of fungal cell) have sufficient structural similarity to loop-out the sequence in between the repeat sequences, e.g., under appropriate selective culture conditions. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

As used herein, a "genomic region" or "genomic locus" is a segment of a chromosome in the genome of a fungal cell that is present on either side of the target site (e.g., including the genomic deletion target and the genomic repeat sequence that is homologous to the repeat sequence in a donor DNA) or, alternatively, also comprises a portion of the target site. The genomic region can comprise at least 50-55, 50-60, 50-65, 50-70, 50-75, 50-80, 50-85, 50-90, 50-95, 50-100, 50-200, 50-300, 50-400, 50-500, 50-600, 50-700, 50-800, 50-900, 50-1000, 50-1100, 50-1200, 50-1300, 50-1400, 50-1500, 50-1600, 50-1700, 50-1800, 50-1900, 50-2000, 50-2100, 50-2200, 50-2300, 50-2400, 50-2500, 50-2600, 50-2700, 50-2800, 50-2900, 50-3000, 50-3100 or more bases.

A "genomic deletion target" and equivalents is the sequence in the fungal genome that a user wants to delete according to aspects of the present disclosure (see FIG. 1). A "loop-out target region" and equivalents is the region between direct repeats (e.g., the genomic repeat sequence and the repeat sequence in the donor DNA that is homologous to the genomic repeat sequence) that is looped-out by homologous recombination between the direct repeats in the fungal genome. In certain embodiments, the loop-out target region includes the genomic deletion target and the selectable marker on the donor DNA inserted at the target site in the fugal genome. A phenotypic marker is a screenable or selectable marker that includes visual markers and selectable markers whether it is a positive or negative selectable marker. Any phenotypic marker can be used. Specifically, a selectable or screenable marker comprises a DNA segment that allows one to identify, select for, or screen for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds and antibiotics, such as, chlorimuron ethyl, benomyl, Basta, and hygromycin phosphotransferase (HPT); DNA segments that encode products which are otherwise lacking in the recipient cell (e.g., tRNA genes, auxotrophic markers, dominant heterologous marker-amdS); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Methods and Compositions for Modifying a Fungal Cell Genome

Methods are provided employing a guide RNA/Cas endonuclease system for inserting a donor DNA at a target site in the genome of a fungal cell, e.g., a filamentous fungal cell.

Aspects of the present disclosure include methods for donor DNA insertion at a target site in the genome of a fungal cell by transiently introducing a Cas endonuclease/guide polynucleotide complex into the cell along with a donor DNA. The Cas endonuclease/guide polynucleotide complex is capable of introducing a double-strand break at the target site in the genome of the fungal cell Introduction of the Cas endonuclease, guide polynucleotide, and the donor DNA can be done in any convenient manner, including transfection, transduction, transformation, electroporation, particle bombardment, cell fusion techniques, etc. Each of these components can be introduced simultaneously or sequentially as desired by the user. For example, a fungal cell can first be stably transfected with a Cas expression DNA construct followed by introduction of a guide polynucleotide into the stable transfectant (either directly or using a guide polynucleotide expressing DNA construct). This set up may even be advantageous as the user can generate a population of stable Cas transfectant fungal cells into which different guide polynucleotides can be introduced independently (in some cases, more than one guide polynucleotide can be introduced into the same cells should this be desired). In some embodiments, a Cas expressing fungal cell is obtained by the user, and thus the user does not need to introduce a recombinant DNA construct capable of expressing a Cas endonuclease into the cell, but rather only need introduce a guide polynucleotide into the Cas expressing cell.

In certain embodiments, a guide polynucleotide is introduced into the fungal cell by introducing a recombinant DNA construct that includes an expression cassette (or gene) encoding the guide polynucleotide. In some embodiments, the expression cassette is operably linked to a eukaryotic RNA pol III promoter. These promoters are of particular interest as transcription by RNA pol III does not lead to the addition of a 5' cap structure or polyadenylation that occurs upon transcription by RNA polymerase II from an RNA pol II dependent promoter. In certain embodiments, the RNA pol III promoter is a filamentous fungal cell U6 polymerase III promoter (e.g., SEQ ID NO:11 and functional variants thereof, e.g., SEQ ID NO:12).

When a double-strand break is induced in the genomic DNA of a host cell (e.g., by the activity of a Cas endonuclease/guide RNA complex at a target site, the complex having double-strand endonuclease activity), the cell's DNA repair mechanism is activated to repair the break which, due to its error-prone nature, can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9).

Surprisingly, we have found in filamentous fungi that non-homologous insertion of transformed DNA at the double-strand break is highly favored over simple end-joining between the two ends of the chromosomal DNA at a double-strand break. Therefore, in cases where the Cas endonuclease or guide RNA is provided by transformation with an expression cassette containing DNA construct or constructs, those DNA constructs, or fragments thereof, are inserted at the double-strand break at high frequency. This insertion occurs in the absence of homology between DNA sequences on the Cas endonuclease or guide RNA expression constructs and the sequences around the double-strand break.

This process can be exploited to provide an efficient mechanism to insert an entire donor DNA into a target site without the need for any homologous region.

DNA taken up by transformation may integrate in a stable fashion in the genome or it may be transiently maintained. In some embodiments, donor DNA stably integrated into the genome is desired but integration of Cas endonuclease expression cassette or guide RNA expression cassette is not. In such embodiments, this goal can be achieved by direct introduction of Cas endonuclease and/or guide RNA transiently or transient introduction of Cas endonuclease expression cassette and/or guide RNA expression cassette. One can select for or screen for stable transformants with regard to the integration of donor DNA (e.g., using a gene product/marker encoded by the donor DNA) and unstable transformants with regard to the integration of Cas endonuclease expression cassette or guide RNA expression cassette (e.g., loss of different gene products/markers which are encoded on the DNA constructs comprising the Cas endonuclease expression cassette or guide RNA expression cassette). In some other embodiments, especially in methods of deleting target sequences from host genome, even donor DNA may not be desired to be stably integrated into the genome, but just needs to be integrated transiently, until homologous recombination has occurred to loop-out the target region. In such cases, one can select for or screen for unstable transformants with regard to the integration of donor DNA (e.g., loss of the gene product/marker encoded by the donor DNA).

Transient maintenance can be recognized by an unstable phenotype. For example, DNA uptake can be recognized by selection for a marker gene present on the transforming DNA. After transformation and selection, the transformants may be grown under non-selective conditions for several generations before transfer back to selective conditions. A stable transformant will be able to grow after transfer back to selective conditions whereas an unstable transformant will be unable to grow after transfer back to selective conditions due to loss of the transforming DNA. We have demonstrated that it is possible to transiently express Cas endonuclease and/or guide RNA in fungal cells/unstable transformants.

In embodiments where unstable transformants are desired, a plasmid with telomere sequences to encourage autonomous replication can be used. Other types of plasmids that are designed for autonomous replication, such as those with autonomous replication sequences, centromere sequences or other sequences, can also be employed. Surprisingly, in *Trichoderma reesei* we have found that one can use plasmids with no known origin of replication, autonomous replication sequence, centromere or telomere sequences. By screening those transformants that show an unstable phenotype with respect to the selectable marker, efficient target site gene modification without vector DNA insertion is obtained (e.g., homologous recombination with a homologous region in a donor DNA).

Certain embodiments of the present disclosure include integrating a Cas endonuclease expression cassette and first selectable marker in the genome of a fungus, optionally flanked by repeats to allow subsequent removal (loop-out) of the expression cassette and first selectable marker, to produce a Cas endonuclease expressing host cell. These cells can be employed in numerous ways to obtain a genetic modification of interest, including insertion of a donor DNA at a target site.

For example, a Cas endonuclease expressing host cell can be transformed with a DNA construct including a guide RNA expression cassette containing a second selectable marker (and optionally a separate donor DNA). Host cells that are selected for using the second selectable marker will express the guide RNA from this DNA construct, which enables Cas endonuclease activity and targeting to a defined target site of interest in the genome. Screening these host cells for transformants that show an unstable phenotype with respect to the second selectable marker will enable obtaining host cells with a modified site of interest (e.g., homologous recombination with the donor DNA) without DNA construct insertion.

As another example, a Cas endonuclease expressing host cell can be induced to uptake an in vitro synthesized guide RNA to enable Cas endonuclease activity and targeting to a defined site in the genome. In some cases, it will be desirable to induce uptake of both guide RNA and a separate DNA construct bearing a selectable marker gene to allow for selection of those cells that have taken up DNA and, at high frequency, are expected to have simultaneously taken up guide RNA. As above, screening those transformants that show an unstable phenotype with respect to the selectable marker for the genetic modification of interest (e.g., homologous recombination with a donor DNA) without vector DNA insertion is obtained.

As yet another example, a Cas endonuclease expressing host cell can be used to create a "helper strain" that can provide, in trans, the Cas endonuclease to a "target strain". In brief, a heterokaryon can be created between the helper strain and the target strain, e.g., by fusion of protoplasts from each strain or by anastomosis of hyphae depending on the species of filamentous fungus. Maintenance of the heterokaryon will depend on appropriate nutritional or other marker genes or mutations in each parental strain and growth on suitable selective medium such that the parental strains are unable to grow whereas the heterokaryon, due to complementation, is able to grow. Either at the time of heterokaryon formation or subsequently, a guide RNA and a donor DNA are introduced by transfection. The guide RNA may be directly introduced or introduced via a DNA construct having a Cas endonuclease expression cassette and a selectable marker gene. Cas endonuclease is expressed from the gene in the helper strain nucleus and is present in the cytoplasm of the heterokaryon. The Cas endonuclease associates with the guide RNA to create an active complex that is targeted to the desired target site(s) in the genome, where the donor DNA is inserted. Subsequently, spores are recovered from the heterokaryon and subjected to selection or screening to recover the target strain with a donor DNA inserted at the target site. In cases in which an expression cassette is used to introduce the guide RNA, heterokaryons are chosen in which the guide RNA expression construct is not stably maintained.

With respect to DNA repair in fungal cells, we have found that in the presence of a functioning NHEJ pathway, error-prone repair is highly favored over homologous recombination at a double strand break site. In other words, with respect to DNA repair of a double strand break in filamentous fungal cells, we have found that in the presence of a functioning NHEJ pathway, non-homologous insertion of donor DNA at the break is highly favored over (1) non-homologous end joining without DNA insertion and (2) homologous recombination at the double strand break site with a donor DNA having desired homologous recombination sites.

In some instances, the donor DNA includes a first region and a second region that are homologous to corresponding first and second regions in the genome of the fungal cell, wherein the regions of homology generally include or surround the target site at which the genomic DNA is cleaved by the Gas endonuclease. These regions of homology promote or allow homologous recombination with their corresponding genomic regions of homology resulting in exchange of DNA between the donor DNA and the genome. As such, the provided methods result in the integration of the polynucleotide of interest of the donor DNA at or near the cleavage site in the target site in the fungal cell genome, thereby altering the original target site, thereby producing an altered genomic target site.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the fungal cell genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, such that the sequences undergo homologous recombination.

The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As with the Cas endonuclease and the guide polynucleotide expression constructs, the donor DNA may be introduced by any convenient means (as discussed elsewhere herein).

In certain embodiments, the Cas endonuclease is a Cas9 endonuclease (see, e.g., WO 2013141680 entitled "RNA-directed DNA Cleavage by the Cas9-crRNA Complex"). Examples of Cas9 endonucleases include those from *Streptococcus* sp. (e.g., *S. pyogenes, S. mutans,* and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*) (see, e.g., Cas9 endonucleases described in Fonfara et al., Nucleic Acids Res., 2013, pages 1-14: incorporated herein by reference). In some embodiments, the Cas endonuclease is encoded by an optimized Cas9 endonuclease gene, e.g., optimized for expression in a fungal cell (e.g., Cas9 encoding genes containing SEQ ID NO:8, e.g., SEQ ID NO:9, as described below).

In certain instances, the Cas endonuclease gene is operably linked to one or more polynucleotides encoding nuclear localization signals such that the Cas endonuclease/guide polynucleotide complex that is expressed in the cell is efficiently transported to the nucleus. Any convenient nuclear localization signal may be used, e.g., a polynucleotide encoding an SV40 nuclear localization signal present upstream of and in-frame with the Cas codon region and a polynucleotide encoding a nuclear localization signal derived from the *T. reesei* blr2 (blue light regulator 2) gene present downstream and in frame with the Cas codon region. Other nuclear localization signals can be employed.

In certain embodiments of the disclosure, the guide polynucleotide is a guide RNA that includes a crRNA region (or crRNA fragment) and a tracrRNA region (or tracrRNA fragment) of the type II CRISPR/Cas system that can form a complex with a type II Cas endonuclease. As indicated above, the guide RNA/Cas endonuclease complex can direct the Cas endonuclease to a fungal cell genomic target site, enabling the Cas endonuclease to introduce a double strand break into the genomic target site. In some cases, the RNA that guides the RNA/Cas9 endonuclease complex is a duplex that includes a crRNA and a separate tracrRNA. In other instances, the guide RNA is a single RNA molecule that includes both a crRNA region and a tracrRNA region (sometimes referred to herein as a fused guide RNA). One advantage of using a fused guide RNA versus a duplexed crRNA-tracrRNA is that only one expression cassette needs to be made to express the fused guide RNA.

Host cells employed in the methods disclosed herein may be any fungal host cells are from the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., supra) and all mitosporic fungi (Hawksworth et al., supra). In certain embodiments, the fungal host cells are yeast cells, e.g., *Candida, Hansenula, Kluyveromyces, Pichia, Saccharomyces, Schizosaccharomyces,* or *Yarrowia* cell. Species of yeast include, but are not limited to, the following: *Saccharomyces carlsbergensis, Saccharomyces cerevisiae, Saccharomyces*

*diastaticus, Saccharomyces douglasii, Saccharomyces kluyveri, Saccharomyces norbensis, Saccharomyces oviformis, Kluyveromyces lactis*, and *Yarrowia lipolytica* cell. In additional embodiments, the fungal cells are filamentous fungal cells including but not limited to species of *Trichoderma, Penicillium, Aspergillus, Humicola, Chrysosporium, Fusarium, Neurospora, Myceliophthora, Hypocrea*, and *Emericella*. For example, the filamentous fungi *T. reesei* and *A. niger* find use in aspects of the disclosed methods.

Virtually any site in a fungal cell genome may be targeted using the disclosed methods, so long as the target site includes the required protospacer adjacent motif, or PAM. In the case of the *S. pyogenes* Cas9, the PAM has the sequence NGG (5' to 3'; where N is A, G, C or T), and thus does not impose significant restrictions on the selection of a target site in the genome. Other known Cas9 endonucleases have different PAM sites (see, e.g., Cas9 endonuclease PAM sites described in Fonfara et al., Nucleic Acids Res., 2013, pages 1-14: incorporated herein by reference).

The length of the target site can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The cleavage site can be within the target sequence or the cleavage site could be outside of the target sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

In some cases, active variant target sequences in the genome of the fungal cell can also be used, meaning that the target site is not 100% identical to the relevant sequence in the guide polynucleotide (within the crRNA sequence of the guide polynucleotide). Such active variants can comprise at least 65%, 70%, 75%, 80%, 85%, 90%, 91%, 92%, 93%, 94%, 95%, 96%, 97%, 98%, 99% or more sequence identity to the given target site, wherein the active variant target sequences retain biological activity and hence are capable of being recognized and cleaved by a Cas endonuclease. Assays to measure the double-strand break of a target site by an endonuclease are known in the art and generally measure the overall activity and specificity of the agent on DNA substrates containing recognition sites.

Target sites of interest include those located within a region of a gene of interest. Non-limiting examples of regions within a gene of interest include an open reading frame, a promoter, a transcriptional regulatory element, a translational regulatory element, a transcriptional terminator sequence, an mRNA splice site, a protein coding sequence, an intron site, and an intron enhancing motif.

In certain embodiments, modification of the genome of the fungal cell results in a phenotypic effect that can be detected and, in many instances, is a desired outcome of the user. Non-limiting examples include acquisition of a selectable cell growth phenotype (e.g., resistance to or sensitivity to an antibiotic, gain or loss of an auxotrophic characteristic, increased or decreased rate of growth, etc.), expression of a detectable marker (e.g., fluorescent marker, cell-surface molecule, chromogenic enzyme, etc.), and the secretion of an enzyme the activity of which can be detected in culture supernatant.

When modification of the genome of the fungal cell results in a phenotypic effect, a donor DNA is often employed that includes a polynucleotide of interest that is (or encodes) a phenotypic marker. Any convenient phenotypic marker can be used, including any selectable or screenable marker that allows one to identify, select for, or screen for or against a fungal cell that contains it, often under particular culture conditions. Thus, in some aspects of the present invention, the identification of fungal cells having a desired genome modification includes culturing the fungal population of cells that have received the Cas endonuclease and guide polynucleotide (and optionally a donor DNA) under conditions to select for or screen for cells having the modification at the target site. Any type selection system may be employed, including assessing for the gain or loss of an enzymatic activity in the fungal cell (also referred to as a selectable marker), e.g., the acquisition of antibiotic resistance or gain/loss of an auxotrophic marker.

In some instances, the genomic modification in the fungal cells is detected directly using any convenient method, including sequencing, PCR, Southern blot, restriction enzyme analysis, and the like, including combinations of such methods.

In some embodiments, specific genes are targeted for modification using the disclosed methods, including genes encoding enzymes, e.g., acetyl esterases, aminopeptidases, amylases, arabinases, arabinofuranosidases, carboxypeptidases, catalases, cellulases, chitinases, cutinase, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, transferases, transport proteins, transglutaminases, xylanases, hexose oxidases, and combinations thereof.

There are numerous variations for implementing the methods described herein. For example, instead of having the Cas expression cassette present as an exogenous sequence in the fungal host cell, this cassette can be integrated into the genome of the fungal host cell. Generating this parental cell line would allow a user to simply introduce a desired guide RNA (e.g., as a guide RNA expression vector) which would then target the genomic site of interest as detailed elsewhere herein. In some of these embodiments, the integrated Cas gene can be designed to include polynucleotide repeats flanking it for subsequent loop-out/removal from the genome if needed.

Non-limiting examples or embodiments of compositions and methods disclosed herein are as follows:

1. A method for inserting a donor DNA at a target site in the genome of a fungal cell, the method comprising:
    a) introducing into a population of fungal cells a Cas endonuclease, a guide RNA, and a donor DNA, wherein the Cas endonuclease and guide RNA are capable of forming a complex that enables the Cas endonuclease to introduce a double-strand break at a target site in a genomic locus of the genome of the fungal cells; and
    b) identifying at least one fungal cell from the population in which insertion of the donor DNA at the target site in the genomic locus has occurred, wherein the Cas endonuclease, the guide RNA, or both are introduced transiently into the population of fungal cells.

2. The method of embodiment 1, wherein the insertion has not occurred via a homologous recombination between the donor DNA and the genome of the fungal cells.
3. The method of embodiment 1 or 2, wherein the donor DNA does not comprise a sequence homologous to a genomic sequence in the genomic locus.
4. The method of any preceding embodiment, wherein the insertion of the donor DNA interrupts the expression or function of the genomic locus.
5. The method of any preceding embodiment, wherein the donor DNA comprises a gene of interest.
6. The method of any preceding embodiment, wherein the donor DNA comprises an expression cassette encoding a gene product of interest.
7. The method of embodiment 6, wherein the gene product of interest is a protein of interest.
8. The method of embodiment 6, wherein the gene product of interest is a phenotypic marker.
9. The method of embodiment 8, wherein the phenotypic marker is selected from the group consisting of an auxotrophic marker, an antibiotic resistance marker, a dominant heterologous selectable marker, and a reporter gene.
10. The method of any one of embodiments 1, 2, and 4-9, wherein the donor DNA comprises a sequence homologous to a genomic sequence in the genomic locus, wherein the genomic sequence and the target site flank a genomic deletion target region, and wherein the insertion of the donor DNA results in the genomic sequence and the sequence homologous to the genomic sequence flanking a loop-out target region comprising the genomic deletion target region.
11. The method of embodiment 10, further comprising:
c) culturing the at least one identified fungal cell under conditions that allow loop-out of the loop-out target region, and
d) identifying at least one fungal cell in the culture in which loop-out of the loop-out target region has occurred.
12. A method for deleting a target region in the genome of a fungal cell, the method comprising:
a) introducing into a population of fungal cells a Cas endonuclease, a guide RNA, and a donor DNA, wherein the Cas endonuclease and guide RNA are capable of forming a complex that enables the Cas endonuclease to introduce a double-strand break at a target site in the genome of the fungal cells and allowing the donor DNA to be inserted at the target cite, wherein the donor DNA comprises a sequence homologous to a genomic sequence of the fungal cells, and wherein the genomic sequence and the target site flank the target region in the fungal cell genome;
b) culturing the population of fungal cells under conditions that allow homologous recombination between the genomic sequence and the sequence homologous to the genomic sequence; and
c) identifying at least one fungal cell in the culture in which deletion of the target region has occurred;
wherein the Cas endonuclease, the guide RNA, or both are introduced transiently into the population of fungal cells.
13. The method of embodiment 12, further comprising, between steps a) and b), a step of identifying at least one fungal cell from the population in which insertion of the donor DNA at the target site has occurred.
14. The method of embodiment 12 or 13, wherein the donor DNA is not inserted at the target site via a homologous recombination between the donor DNA and the fungal cell genome.
15. The method of any preceding embodiment, wherein the Cas endonuclease is a Type II Cas9 endonuclease or variant thereof.
16. The method of embodiment 15, wherein the Cas9 endonuclease or variant thereof comprises a full length Cas9 or a functional fragment thereof from a species selected from the group consisting of: *Streptococcus* sp., *S. pyogenes*, *S. mutans*, *S. thermophilus*, *Campylobacter* sp., *C. jejuni*, *Neisseria* sp., *N. meningitides*, *Francisella* sp., *F. novicida*, *Pasteurella* sp., and *P. multocida*.
17. The method of embodiment 16, wherein the Cas9 endonuclease or variant thereof comprises an amino acid sequence that has at least 70% identity to any one of SEQ ID NOs:1 to 7.
18. The method of any preceding embodiment, wherein the introducing step comprises introducing a DNA construct comprising an expression cassette for the Cas endonuclease into the fungal cells.
19. The method of any preceding embodiment, wherein the introducing step comprises introducing a DNA construct comprising an expression cassette for the guide RNA into the fungal cells.
20. The method of any one of embodiments 1 to 17 and 19, wherein the introducing step comprises directly introducing the Cas endonuclease into the fungal cells.
21. The method of any one of embodiments 1 to 18 and 20, wherein the introducing step comprises directly introducing the guide RNA into the fungal cells.
22. The method of embodiment 18, wherein the expression cassette for the Cas endonuclease comprises a Cas coding sequence that is optimized for expression in the fungal cell.
23. The method of embodiment 22, wherein the Cas coding sequence is a Cas9 coding sequence comprising a polynucleotide sequence that is at least 70% identical to SEQ ID NO:8.
24. The method of any preceding embodiment, wherein the Cas endonuclease is operably linked to a nuclear localization signal.
25. The method of any preceding embodiment, wherein the fungal cell is a filamentous fungal cell.
26. The method of any preceding embodiment, wherein the fungal cell is a Eumycotina or Pezizomycotina fungal cell.
27. The method of any preceding embodiment, wherein the fungal cell is selected from the group consisting of: *Trichoderma*, *Penicillium*, *Aspergillus*, *Humicola*, *Chrysosporium*, *Fusarium*, *Myceliophthora*, *Neurospora*, *Hypocrea*, and *Emericella*.
28. The method of any preceding embodiment, wherein the target site is located within a region of a gene of interest selected from the group consisting of an open reading frame, a promoter, a regulatory sequence, a terminator sequence, a regulatory element sequence, a splice site, a coding sequence, a polyubiquitination site, an intron site, and an intron enhancing motif.
29. A recombinant fungal cell produced by the method of any preceding embodiment.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1: Heterologous Expression of CRISPR SpyCas9 in E. coli

Figure 2:
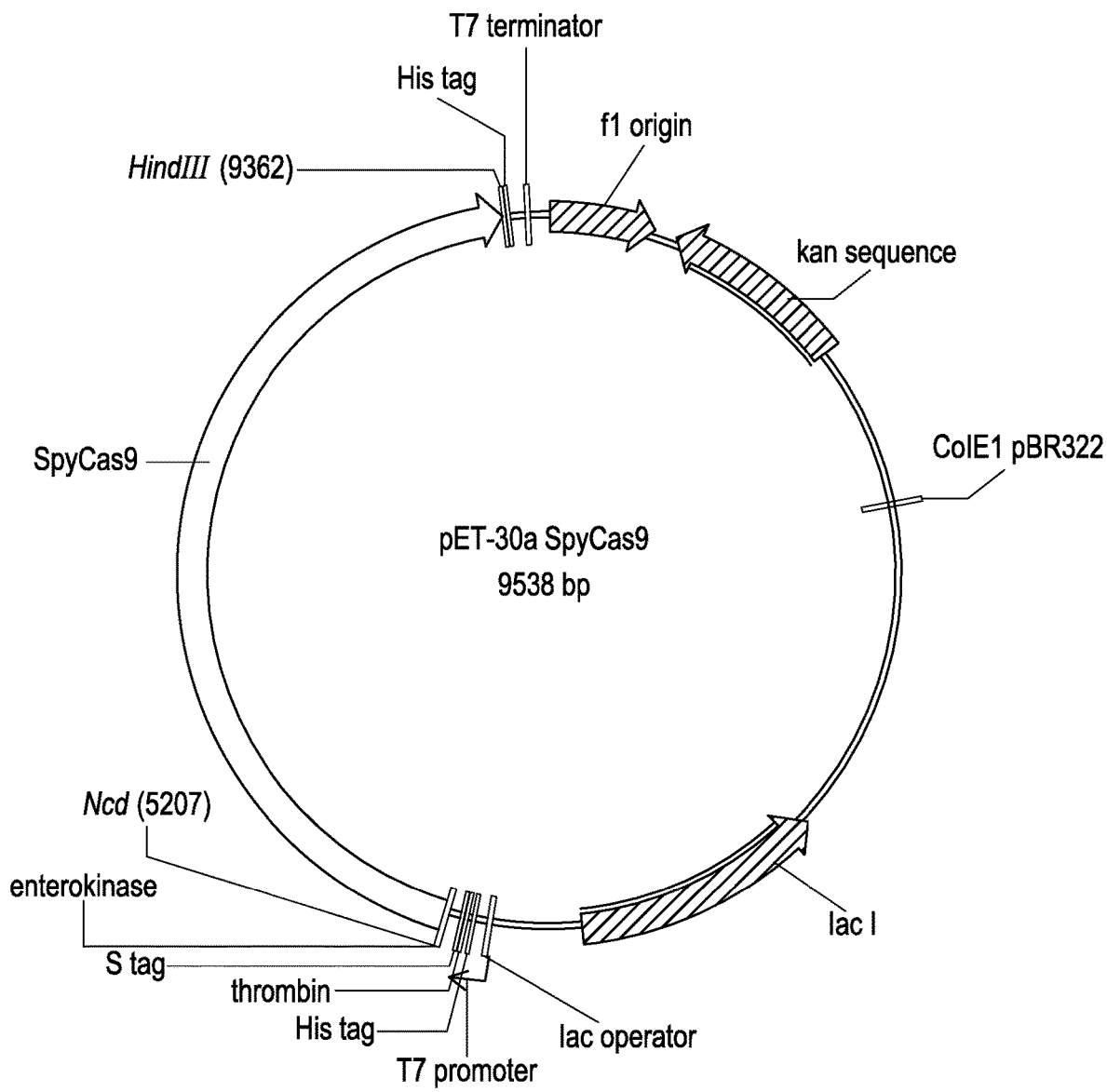
FIG. 2. Plasmid map of pET30a-SpyCas9.

E. coli codon-optimized Streptococcus pyogenes Cas9 (SpyCas9) gene was synthesized and inserted into the expression vector pET30a at NcoI and HindIII sites by Generay (Shanghai, China), resulting in the plasmid pET30a-SpyCas9 (FIG. 2). As indicated in the plasmid map in FIG. 2, the full coding sequence of the expression cassette contains, in 5' to 3' orientation, a sequence encoding an N-terminal His6 tag/thrombin/S•Tag™ enterokinase region (SEQ ID NO:13; includes a start codon methionine), a sequence encoding an SV40 nuclear localization signal (SEQ ID NO:14), a sequence encoding the SpyCas9 (SEQ ID NO:15), and a sequence encoding the BLR nuclear localization signal (SEQ ID NO:16) all in operable linkage. This entire coding sequence is shown in SEQ ID NO:17. The amino acid sequence of the N-terminal His6 tag/thrombin/S•Tag™/enterokinase region encoded by SEQ ID NO:13 is shown in SEQ ID NO:18 (including the methionine at position 1), the amino acid sequence of the SV40 nuclear localization signal encoded by SEQ ID NO:14 is shown in SEQ ID NO:19, the amino acid sequence of the SpyCas9 encoded by SEQ ID NO:15 is shown in SEQ ID NO:1, and the amino acid sequence of the BLR nuclear localization signal encoded by SEQ ID NO:16 is shown in SEQ ID NO:20. The amino acid sequence encoded by SEQ ID NO:17 is shown in SEQ ID NO:21.

The pET30a-SpyCas9 plasmid was transformed into Rosetta2 (De3)plysS E. coli strain (Novagen®, EMD Biosciences, Inc., Merck KGaA, Darmstadt, Germany) and the transformation products were spread on Luria Agar plates supplemented with 34 ppm Chloramphenicol and 50 ppm Kanamycin. Colonies were picked and cultivated for 24 hours in a 250 ml shake flask with 25 ml of the Invitrogen MagicMedia™ E. coli Expression Medium (Thermo Fisher Scientific Inc., Grand Island, N.Y.).

Example 2: Purification of SpyCas9

For purification of SpyCas9, a combination of affinity, hydrophobic interaction and size exclusion chromatographic steps were applied. Briefly, SpyCas9 expressing E. coli cells (Rosetta2 (De3)plysS, as described above) were cultured in a 250 ml shake flask with 25 ml MagicMedia™ for 24 hours and harvested by centrifugation. Cells (approximately 40 grams) were pelleted and resuspended in 400 ml lysis buffer (20 mM HEPES, pH7.5, 500 mM NaCl, 0.1% Triton X-100, 1 mM DTT and 1 mM TCEP, protease inhibitor cocktail purchased from Roche) and lysed via ultra-sonicator (35% power, 20 min, 2s on/3s off) (SCIENT2-II D, Ningbo Scientz Biotechnology Co., LTD). The lysate was cleared by centrifugation at 20000 g for 40 min.

Approximately 400 ml of clarified lysate was incubated with 5 ml Ni-NTA resin (GE Healthcare) overnight at 4° C. with shaking at 30 rpm/min using a Rolling Incubator (Kylin-Bell Lab. Instruments Co., Ltd. Haimen, China). After centrifugation, the resin was transferred to a XK26/20 column (GE Healthcare) and connected to AKTA Explorer system (GE Healthcare). After being washed extensively with equilibration buffer (20 mM HEPES, pH 7.5, 300 mM NaCl, 0.1% Triton X-100) followed by wash buffer (25 mM imidazole in equilibration buffer), the target protein was eluted with 250 mM imidazole in equilibration buffer.

To the active fraction collected from the affinity step, ammonium sulfate was added to a final concentration of 0.8 M and loaded onto a 20 ml phenyl-Sepharose HP column (GE Healthcare). The column was eluted with a gradient of 0.8 M to 0.0 M ammonium sulfate in 50 mM HEPES buffer pH 7.5 and the flow through was collected.

Finally, the protein was further purified by size exclusion chromatography on a Superdex 200 16/60 column (GE Healthcare) in 20 mM HEPES pH7.5, 150 mM KCl and 10% glycerol. The fraction with the highest purity were pooled and concentrated via Amicon 30 KDa membrane filter (Millipore). The final protein sample was stored at −20° C. freezer in the 40% glycerol until use.

Example 3: In Vitro DNA Cleavage Assay

Preparation of Substrate DNA Fragment for In Vitro Spy-Cas9 DNA Cleavage Assays

Genomic DNA was extracted from a Trichoderma reesei strain derived from RL-P37 and having the cellobiohydrolase 1, cellobiohydrolase 2, endoglucanase 1, and endoclucanase 2 genes deleted (Δcbh1, Δcbh2, Δegl1, and Δegl2 strain; also called "quad-delete strain"; see WO 92/06184 and WO 05/001036)) using the ZF Fungal/Bacterial DNA miniprep kit from Zymo (Cat No. D6005). With 1 ng of extracted genomic DNA, DNA fragment containing the Trichoderma reesei glucoamylase (TrGA) gene (Gene ID: 18483895) and its partial 5'-UTR (SEQ ID NO:22) was amplified by PCR using KOD-Plus PCR kit (Toyobo Co., LTD, Japan) and 0.4 μM of each forward and reverse primers: 5'-gactgtctccaccatgtaattttc-3'(SEQ ID NO:23) and 5'-ggcagactacaagtctactagtactac-3' (SEQ ID NO:24). PCR products were purified and concentrated with the DNA Clean & Concentrator™-5 kit from Zymo (Cat No. D4013 (50)), and its DNA concentration was determined with NanoDrop™ (Thermo Fisher).

SEQ ID NO:22 (below) shows the nucleotide sequences of the substrate DNA fragment. The UTR sequences are shown in lowercase while the TrGA gene is shown in uppercase. The selected VT domain, TrGA_Sth_sgR2, is shown in bold (SEQ ID NO:25) and the 500 bp fragment applied for further loop-out experiment is shown in underlined (SEQ ID NO:26).

```
                                                          (SEQ ID NO: 22)
gactgtctccaccatgtaattttccctgcgactccatataacgccggatcgtgaaattttcttctttctttccttccttctcaacaa acaacggatctgtgctttgcggtcccctgcgttcacgcgtcagggtcgactgctctgcagctcgataactccatggagccat caacttgctatggtgtcaatcatcctatcgacaggtccaagaacaagccggcctccggctgcctcattcgctgtcgcaaga cggcttgagtgttgtggctggaggattcggggcccccatattccaacccttttttccaaggccgtcggccggtgaggttgag
```

-continued

```
gaaaaccatggggttgcctacatattatcgatgctggtgtttggtagtagcaatgtttgcggtggcagtttgagccgagcctcgt
cttgggcttctgacccaggcaacgccatctgactagctgcgccgaaggaaggatgattcattgtacgacgccagtcaatg
gaatcttcaagtaaaagcccgacgaaccgaccatgtcagatatcagaattctcctggctggtggggttggttggagactgc
ttacggagtcgatgcctcgtgactgtcatggccgcgtccagcctcctgggactctgtccgatattatgacacgagtaaagcc
tgcatgatgtcagtttgctgcgtctcatgtcgagaacaacacacctggtgctacataggcaatactacctcgtagcttcaaa
gttgactgttttgctttgatgtctttgatcatgcccatccatcccttgtcttgcagtgcatgtggatctctacgtccagacggggag
aaagcttgtctgtgataaagtacgatgatgcattgatgcctgtggctacggcccttttatccccatcgtcatgcatctctatatta
atccaggagactctcctcctggcatgggtgagtacaagtgacgaggacatgtagaagcagagccacgcaacgtcttga
catctgtacctattttgggccaaaaatcgagacccaccagctcgtcctaccttacatgtgaagatcttagcccacaatcctac
tgttttactagtattactgcacagctgtcatcacgagtcctcggttgcttgtgaaacccagctcagctcctgagcacatgcagt
aacgccgactcggcgtcatttcgccacacccaatttggacctgagggatgctggaagctgctgagcagatcccgttaccg
attcatggcactactacatccatacgcagcaaacatgggcttgggcttggcttctcaatgcaaaattgcccgcaaaagtcc
eggcattgtcgatgcagagatgcagatttcagcgggcgattctagggtagggcgactactactaataccacctagtca
gtatgtatctagcaccggaggctaggcggttagtggacgggaacctggtcattccatcgcaaccaggatcccgcacttcgt
tgcgcttctgccccacggggcgggagttggcagaggcagaatgcggagcagcccctttgtctgccctggccggggcct
gttgaagcaagcagacgagagcagagcggttgagaagcggtggttgacgcttgacggtacgaagacgagcgagaat
cccgttaagccgaggctgggctcccccccgtcatcatcatgccatcctgctcttccagcccactcgtctccctgcctcgt
cgcctcccctccctccccgattagctgcgcatgttctcctgacagcgtgactaatgacgcgttgccagcccattcgcctga
cgcatcccggcatctgagtctagctcgtcacgctggcaatcttggcccaggcagagcagcaagacggcgggcatgattg
ggccgtgcctggcgggcatcagctggccatccgctgccacccgagaccgcatcaccgacttgtcggatctctccgagc
agcaggaggctgatcctggccggcgagacgattgaaaagggctgccgggcccggagcaggacagcggcgagagc
gagcgagagagaggaaaagaagaaggtcgactgtcttattttcagccagccccggctcaacagaagcagaggagaa
ggcgaacgacgtcaacgacgacgacgacgacgacgaagacggtgaagtccgttagttgaagatccttgccgtcacaa
caccatctcgtggatattgctttcccctgccgttgcgttgccacctgttccctctttctcttccccccttcttcctcattccgagcgct
actggttcctactccgcagccttcggttgtgcctttctctttgtcgaccattgcaccgcccgtcgcggcacttgggcccggag
aattcggccctttcgcagcattttggccctcagttccccatggggacggtccacacttcctctcttggccctgcagacctttgt
cgtcggtccgagtcggaagaagctcagtcttgagcgcttgagtagcatctacgcgcgaatcactggacaaagtcggcaa
gacgaagccgtcgtcgcctgctgctgctgctgttactgcgacaggcgctccgactgggggcatcggcataataaaaagat
gcccgccttcgccatggacctggccatgagccactcggcatcggctctctctctcaacgcttcctctcacacatcctccttcat
tccgcccatcATGCACGTCCTGTCGACTGCGGTGCTGCTCGGCTCCGTTGCCGTTCAA
AAGGTCCTGGGAAGACCAGGATCAAGCGGTCTGTCCGACGTCACCAAGAGGTCT
GTTGACGACTTCATCAGCACCGAGACGCCTATTGCACTGAACAATCTTCTTTGCAAT
GTTGGTCCTGATGGATGCCGTGCATTCGGCACATCAGCTGGTGCGGTGATTGCAT
CTCCCAGCACAATTGACCCGGACTGTAAGTTGGCCTTGATGAACCATATCATATATC
GCCGAGAAGTGGACCGCGTGCTGAGACTGAGACAGACTATTACATGTGGACGCGA
GATAGCGCTCTTGTCTTCAAGAACCTCATCGACCGCTTCACCGAAACGTACGATGC
GGGCCTGCAGCGCCGCATCGAGCAGTACATTACTGCCCAGGTCACTCTCCAGGGC
CTCTCTAACCCCTCGGGCTCCCTCGCGGACGGCTCTGGTCTCGGCGAGCCCAAG
TTTGAGTTGACCCTGAAGCCTTTCACCGGCAACTGGGGTCGACCGCAGCGGGATG
GCCCAGCTCTGCGAGCCATTGCCTTGATTGGATACTCAAAGTGGCTCATCAACAAC
AACTATCAGTCGACTGTGTCCAACGTCATCTGGCCTATTGTGCGCAACGACCTCAA
```

-continued

```
CTATGTTGCCCAGTACTGGTCAGTGCTTGCTTGCTCTTGAATTACGTCTTTGCTTGT

GTGTCTAATGCCTCCACCACAGGAACCAAACCGGCTTTGACCTCTGGGAAGAAGT

CAATGGGAGCTCATTCTTTACTGTTGCCAACCAGCACCGAGGTATGAAGCAAATCC

TCGACATTCGCTGCTACTGCACATGAGCATTGTTACTGACCAGCTCTACAGCACTT

GTCGAGGGCGCCACTCTTGCTGCCACTCTTGGCCAGTCGGGAAGCGCTTATTCAT

CTGTTGCTCCCCAGGTTTTGTGCTTTCTCCAACGATTCTGGGTGTCGTCTGGTGGA

TACGTCGACTCCAACAGTATGTCTTTTCACTGTTTATATGAGATTGGCCAATACTGAT

AGCTCGCCTCTAGTCAACACCAACGAGGGCAGGACTGGCAAGGATGTCAACTCCG

TCCTGACTTCCATCCACACCTTCGATCCCAACCTTGGCTGTGACGCAGGCACCTTC

CAGCCATGCAGTGACAAAGCGCTCTCCAACCTCAAGGTTGTTGTCGACTCCTTCC

GCTCCATCTACGGCGTGAACAAGGGCATTCCTGCCGGTGCTGCCGTCGCCATTGG

CCGGTATGCAGAGGATGTGTACTACAACGGCAACCCTTGGTATCTTGCTACATTTGC

TGCTGCCGAGCAGCTGTACGATGCCATCTACGTCTGGAAGAAGACGGGCTCCATC

ACGGTGACCGCCACCTCCCTGGCCTTCTTCCAGGAGCTTGTTCCTGGCGTGACG

GCCGGGACCTACTCCAGCAGCTCTTCGACCTTTACCAACATCATCAACGCCGTCTC

GACATAGCCGATGGCTTCCTCAGCGAGGCTGCCAAGTACGTCCCCGCCGACGGT

TCGCTGGCCGAGCAGTTTGACCGCAACAGCGGCACTCCGCTGTCTGCGCTTCAC

CTGACGTGGTCGTACGCCTCGTTCTTGACAGCCACGGCCCGTCGGGCTGGCATC

GTGCCCCCCTCGTGGGCCAACAGCAGCGCTAGCACGATCCCCTCGACGTGCTCC

GGCGCGTCCGTGGTCGGATCCTACTCGCGTCCCACCGCCACGTCATTCCCTCCGT

CGCAGACGCCCAAGCCTGGCGTGCCTTCCGGTACTCCCTACACGCCCCTGCCCT

GCGCGACCCCAACCTCCGTGGCCGTCACCTTCCACGAGCTCGTGTCGACACAGT

TTGGCCAGACGGTCAAGGTGGCGGCAACGCCGCGGCCCTGGGCAACTGGAGC

ACGAGCGCCGCCGTGGCTCTGGACGCCGTCAACTATGCCGATAACCACCCCCTGT

GGATTGGGACGGTCAACCTCGAGGCTGGAGACGTCGTGGAGTACAAGTACATCAA

TGTGGGCCAAGATGGCTCCGTGACCTGGGAGAGTGATCCCAACCACACTTACACG

GTTCCTGCGGTGGCTTGTGTGACGCAGGTTGTCAAGGAGGACACCTGGCAGTCG

TAAtgaatcggcaaggggtagtactagtagacttgtagtctgcc
```

In Vitro Transcription and SpyCas9 DNA Cleavage Assays

Figure 3:
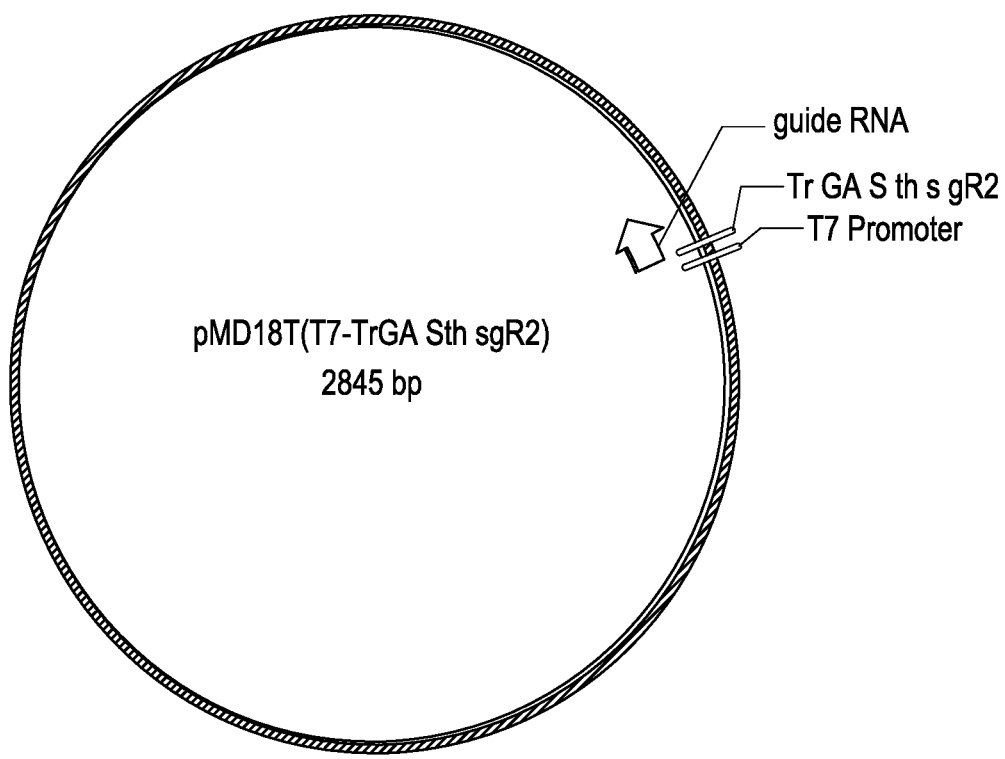
FIG. 3. Plasmid maps of pMD18T (T7-TrGA_Sth_sgR2).

One VT domain in TrGA gene, TrGA_Sth_sgR2 (SEQ ID NO:25), and its specific PAM, were identified for downstream in vitro assay and transformation experiments. Oligonucleotides were inserted into the pMD18T vector by Generay, resulting in pMD18T(T7-TrGA_Sth_sgR2) (FIG. 3) (see SEQ ID NO:27 below for the T7 promoter, CER domain, and the VT domain TrGA_Sth_sgR2 sequences). DNA fragment for the in vitro transcription were amplified from pMD18T (T7-TrGA_Sth_sgR2) by PCR with 0.4 µM of each forward and reverse primers: 5'-cttttacggttcctggc-3' (SEQ ID NO:28) and 5'-aaaagcaccgactcgg-3' (SEQ ID NO:29). PCR products were purified and concentrated with the DNA Clean & Concentrator™-5 kit from Zymo (Cat No. D4013), and its DNA concentration was determined.

With the above specific PCR product as template, RNA for VT domain TrGA_Sth_sgR2 was generated by in vitro transcription using MEGAshortscript™ T7 transcription kit from Thermo Fisher Scientific Inc. according to the manufacturer's instructions. Transcribed RNAs were purified using MEGAclear™ Transcription Clean-Up kit from Thermo Fisher Scientific Inc. The RNA concentration was measured with NanoDrop™.

SpyCas9 in vitro DNA cleavage assays were performed to confirm the activity of the synthesized single-guide RNA. To initiate the assay, 1 µg of purified SpyCas9, 200 ng of substrate DNA fragment, and 200 ng of single-guide RNA (or water as control) were mixed together in 15 µl reaction buffer containing 50 mM HEPES pH 7.3, 150 mM KCl, 0.5 mM DTT and 10 mM MgCl2. Assays were carried out at 37 Celsius for 20 min, followed by the addition of 2 µg of Proteinase K (Sigma, Cat No. P6556). The reaction was continued at 40° C. for 20 min and terminated by an additional incubation at 80° C. for 20 min. The reaction results were analyzed using 0.8% agarose gel, running at 140 volts for 30 min.

Figure 4:
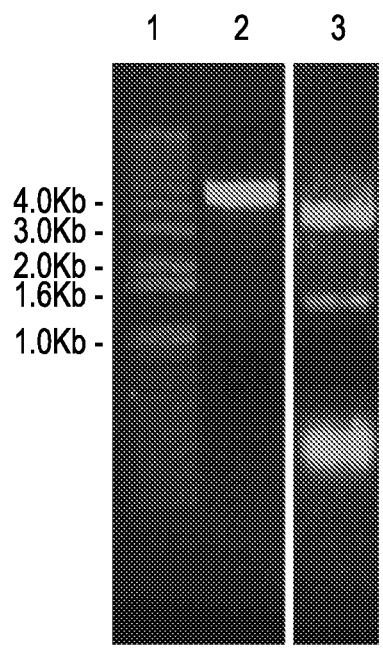
FIG. 4. SpyCas9 nuclease assay. Lane 1, DNA ladder; lane 2 and lane 3, SpyCas9 assay in the presence of water and TrGA_Sth_sgR2, respectively.

As shown in FIG. 4, in the presence of specific single-guide RNA, SpyCas9 can successfully cut substrate DNA fragment into the desired sizes (lane 3), confirming the function of the synthesized RNA. In the absence of the guide RNA (TrGA_Sth_sgR2), no cutting of the substrate DNA is observed (Lane 2).

SEQ ID NO:27 shows the template sequence for transcription consisting of the T7 promoter, CER domain, and the VT domain TrGA_Sth_sgR2. The VT domain was shown in uppercase, while the T7 promoter and CER domain region were shown in bold and lowercase, respectively.

(SEQ ID NO: 27)
taatacgactcactatagGGTGTGGATGGAAGTCAGGAgttttagagcta gaaatagcaagttaaaataaggctagtccgttatcaacttgaaaaagtgg caccgagtcggtgc

Example 4: In Vivo SpyCas9/sgRNA Uptake Experiment

Protoplast Preparation

For protoplast preparation, $5 \times 10^8$ spores of a quad-delete strain of *T. reesei* (described above) with an additional alpha-amylase deletion (grown on a PDA plate for 5 days at 30° C.) were inoculated into 50 ml germination medium (recipe described in U.S. Pat. No. 8,679,815) in a 250 ml shake flask with 4 baffles and incubated at 27° C. for 17 hours at 170 rpm. The mycelia were recovered by transferring the liquid volume into 50 ml conical tubes and spinning at 3000 rpm for 10 minutes. The supernatant was decanted and the mycelial pellets were washed twice using 1.2 M MgSO4-10 mM Na-phosphate buffer and resuspended in 15 ml lysing enzyme buffer. Lysing Enzyme from *Trichoderma harzianum* (Sigma catalog #L1412)) was dissolved in 1.2 M MgSO4-10 mM Na-phosphate buffer (pH 5.8), 50 mg/ml). The cell suspension was transferred into a 250 ml shake flask with 4 baffles and shaken at room temperature for at least 2 hours at 200 rpm. The protoplasts were harvested by filtration through Miracloth (Calbiochem Art. No. 475855) folded in a glass funnel into a Greiner tube. 0.6 M Sorbitol-0.1 M Tris-HCl buffer was added carefully on top of the filtered protoplasts. The protoplasts were collected by centrifugation for 15 minutes at 4000 rpm. The middle phase containing the protoplasts was transferred into a new tube and added at least an equal volume of 1.2 M Sorbitol-10 mM Tris-HCl buffer. The protoplasts were collected by centrifugation for 5 minutes at 4000 rpm, and washed two times with 1.2M sorbitol-10 mM Tris-HCl buffer. The pellet was resuspended into at least 1 ml 1.2 M Sorbitol-10 mM Tris-HCl pH 7.5-10 mM CaCl2 buffer and the number of protoplasts counted under a microscope. The protoplast suspension was diluted using 4 parts of 1.2 M Sorbitol-10 mM Tris-HCl—10 mM CaCl2 and 1 part of 25% PEG6000-50 mM CaCl2-10 mM Tris-HCl until $5 \times 10^8$ per ml for the future transformation.

Preparation of Deletion Cassette

The TrGA deletion cassette contained a pyr2 (orotate phospho-ribosyltransferase) expression cassette including the pyr2 promotor, pyr2 CDS and pyr2 terminator, followed by a 500 bp repeat sequence for the further loop out. The nucleotide sequence of the TrGA knockout cassette is depicted as SEQ ID NO:30.

SEQ ID NO:30 below shows the nucleotide sequence of the TrGA knockout cassette. The pyr2 promotor (SEQ ID NO:31), pyr2 CDS (SEQ ID NO:32), pyr2 terminator (SEQ ID NO:33), and the 500 bp repeat sequence (SEQ ID NO:34) are shown in lowercase, italic, bold and underlined, respectively.

(SEQ ID NO: 30)
ctcgagtttataagtgacaacatgctctcaaagcgctcatggctggcacaagcctggaaagaaccaacacaaagcata ctgcagcaaatcagctgaattcgtcaccaattaagtgaacatcaacctgaaggcagagtatgaggccagaagcacatct ggatcgcagatcatggattgcccctcttgttgaagatgagaatctagaaagatggcggggtatgagataagagcgatgg gggggcacatcatcttccaagacaaacaaccttttgcagagtcaggcaattttcgtataagagcaggaggagggagtcc agtcatttcatcagcggtaaaatcactctagacaatcttcaagatgagttctgccttgggtgacttatagccatcatcatacct agacagaagcttgtgggatactaagaccaacgtacaagctcgcactgtacgctttgacttccatgtgaaaactcgatacg gcgcgcctctaaattttatagctcaaccactccaatccaacctctgcatccctctcactcgtcctgatctactgttcaaatcag agaataaggacactatccaaatccaacagaatggctaccacctcccagctgcctgcctacaagcaggacttcctcaaat ccgccatcgacggcgcgtcctcaagtttggcagcttcgagctcaagtccaagcggatatcccctacttcttcaacgcgg gcgaattccacacggcgcgcctcgccggcgccatcgcctccgcctttgcaaagaccatcatcgaggcccaggagaag gccggcctagagttcgacatcgtcttcggcccggcctacaagggcatcccgctgtgctccgccatcaccatcaagctcgg cgagctggcgccccagaacctggaccgcgtctcctactcgtttgaccgcaaggaggccaaggaccacggcgagggcg gcaacatcgtcggcgcttcgctcaagggcaagagggtcctgattgtcgacgacgtcatcaccgccggcaccgccaaga gggacgccattgagaagatcaccaaggagggcggcatcgtcgccggcatcgtcgtggccctggaccgcatggagaa gctccccgctgcggatggcgacgactccaagcctggaccgagtgccattggcgagctgaggaaggagtacggcatcc ccatctttgccatcctcactctggatgacattatcgatggcatgaagggctttgctaccctgaggatatcaagaacacgga ggattaccgtgccaagtacaaggcgactgactgattgaggcgttcaatgtcagaagggagagaaagactgaaaag gtggaaagaagaggcaaattgttgttattattattattctatctcgaatcttctagatcttgtcgtaaataaacaagcg

-continued
taactagctagcctccgtacaactgcttgaatttgatacccgtatggagggcagttattttattttgttttcaagatttt ccattcgccgttgaactcgtctcacatcgcgtgtattgcccggttgcccatgtgttctcctactacccaagtccct cacgggttgtctcactttctttctcctttatcctccctattttttttcaagtcagcgacagagcagtcatatggggatac gtgcaactgggactcacaacaggccatcttatggcctaatagccggcgttggatccactagtcaattgagcacat gcagtaacgccgactcggcgtcatttcgccacacccaatttggacctgagggatgctggaagctgctgagcagatcccgt taccgattcatggcactactacatccatacgcagcaaacatgggcttgggcttggcttctcaatgcaaaattgcccgcaaa agtcccggcattgtcgatgcagagatgcagatttcagcgggcgattctagggtagggcgactactactactaataccacct agtcagtatgtatctagcaccggaggctaggcggttagtggacgggaacctggtcattccatcgcaaccaggatcccgc acttcgttgcgcttctgccccacggggcgggagttggcagaggcagaatgcggagcagcccttgtctgccctggccg gggcctgttgaagcaagcagacgagagcagagcggttgagaagcggtggttgacgcttgacggtacgaagacgagc gagaatcccgttaagccgaggctgggc Transformation To initiate the uptake experiment, 20 µg Spycas9 protein was mixed with 16 µg sgRNA (TrGA_Sth_sgR2, described in Example 3) and 2 µl of NEB buffer#3 (New England Biolabs) and the final volume was adjusted to 20 µl. After 30 min incubation at room temperature, the SpyCas9/sgRNA premixer (or 2 µl of NEB buffer#3 dissolved in 18 µl nuclease-free water as control) was mixed with 10 µg deletion cassette to form a premixer solution with a final volume of 30 ul. The premixer was added to 200 µL protoplast ($1 \times 10^8$) and kept on ice for 30 min. After incubation, protoplasts were added to cooled molten sorbitol/Vogel agar (1.1 M sorbitol of minimal Vogel agar) to be as the top layer of the minimal Vogel plate (Davis et al., (1970) Methods in Enzymology 17A, pp. 79-143 and Davis, Rowland, NEUROSPORA, CONTRIBUTIONS OF A MODEL ORGANISM, Oxford University Press, (2000)). The plates were incubated at 30° C. for a week. The detailed steps are described in U.S. Pat. No. 8,679,815 (incorporated herein by reference).

Figure 5:
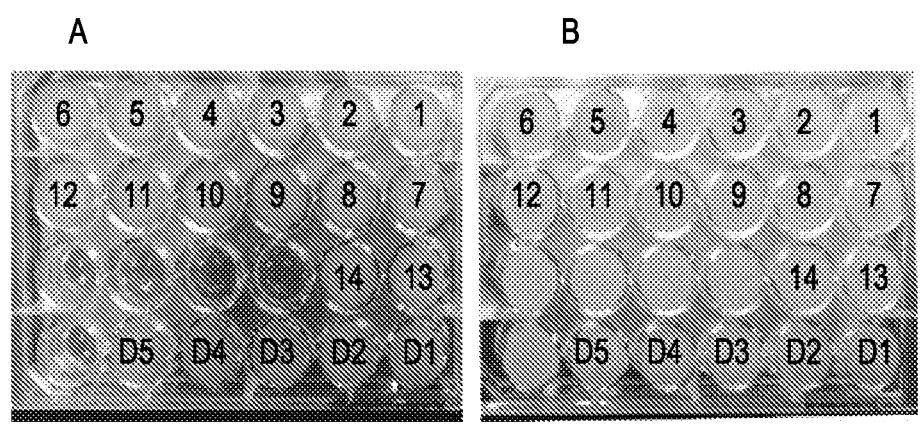
FIG. 5. The morphology of transformants in Vogel-starch (glucose free) plate assays. Transformants 1 to 14 were picked from the plates with SpyCas9/sgRNA treatment while transformants D1 through D5 were randomly selected from control plates. Panel A, regular Vogel agar plate. Panel B, Vogel-starch (glucose free) plate.

Compared to the control plates (i.e., with no SpyCas9/sgRNA premix added) that have hundreds of transformants, only 14 transformants were obtained from the protoplast with the SpyCas9/sgRNA premixer treatment. Among those 14 transformants, 13 (>90%) displayed TrGA knock-out phenotype based on the Vogel-starch (glucose free) plate assays (FIG. 5) (Colonies with TrGA knockout phenotype will grow on regular Vogel agar plate (Panel A; all clones grew) but not on glucose free Vogel-starch plate (Panel B; clones 1-4 and 6-14 from the SpyCas9/sgRNA premixer treatment did not grow, demonstrating that they are TrGA deficient).

All 13 transformants (1 to 4, 6 to 14, FIG. 5) displaying the TrGA knock-out phenotype were transferred and grown on a new Vogel plate for the downstream loop-out experiment. After 7 days growth, all the spores were collected and diluted to desired concentrations (Table 1) and subsequently spread on the Vogel agar plate supplemented with 1.2 g/L FOA to select for loop-out of the pyr2 expression cassette. The randomly selected transformants (D1 to D5, FIG. 4) from control plate were processed similarly. After 7 days growth on the Vogel-FOA plate, colonies were observed for the transformants with SpyCas9/sgRNA treatment, but none were seen for transformants from the controls (no SpyCas9/sgRNA treatment; see Table 1). This indicates that the pyr2 expression cassette was looped-out via a recombination event between the repeat sequence present in the genome and in the TrGA knockout cassette (SEQ ID NO:34) rather than merely spontaneous mutation of the pyr2 expression cassette. If spontaneous mutations were the underlying cause, both experimental and control samples would have FOA resistant colonies.

TABLE 1

Results of loop-out experiment using Vogel-FOA agar plate

| Starting spore concentration | Colony number | |
|---|---|---|
| (cells/mL) | With SpyCas9/sgRNA treatment | Control |
| $10^8$ | >100 | 0 |
| $10^7$ | 41 | 0 |
| $10^6$ | 12 | 0 |
| $10^5$ | 2 | 0 |

Loop-Out Strain Verification 32 colonies from the Vogel-FOA plates were randomly selected and subjected to PCR confirmation with 0.4 µM of each of forward and reverse primers: 5'-ggtgtttggtagtagcaatg-3' (SEQ NO:35) and 5'-ggcagacta-caagtctactagtactac-3' (SEQ ID NO:36). After sequencing each PCR product, 3 colonies displaying the expected loop-out sequences (SEQ ID NO:37) were confirmed, demonstrating the success of target gene deletion in T. reesei using the combination of SpyCas9, specific sgRNA and deletion cassette.

SEQ ID NO:37 shows the expected nucleotide sequences of the PCR product of loop-out strains. The upstream and downstream UTR sequences are shown in lowercase (SEQ ID NO:38 and 39, respectively) while the partial TrGA ORF fragment is shown in uppercase (SEQ ID NO:40). The 500 bp fragment retained after the loop-out experiment is underlined (SEQ ID NO:41), which is identical to the repeat sequence present in the genome and in the TrGA knockout cassette (SEQ ID NO:34).

(SEQ ID NO: 37)
ggtgtttggtagtagcaatgtttgcggtggcagtttgagccgagcctcgtcttgggcttctgacccaggcaacgccatctgac tagctgcgccgaaggaaggatgattcattgtacgacgccagtcaatggaatcttcaagtaaaagcccgacgaaccgac catgtcagatatcagaattctcctggctggtggggttggttggagactgcttacggagtcgatgcctcgtgactgtcatggcc -continued

```
gcgtccagcctcctgggactctgtccgatattatgacacgagtaaagcctgcatgatgtcagtttgctgcgtctcatgtcgag aacaacacacctggtgctacataggcaatactacctcgtagcttcaaagttgactgttttgctttgatgtctttgatcatgccca tccatcccttgtcttgcagtgcatgtggatctctacgtccagacggggagaaagcttgtctgtgataaagtacgatgatgcatt gatgcctgtggctacggcccttttatccccatcgtcatgcatctctatattaatccaggagactctcctcctggcatgggtgagt acaagtgacgaggacatgtagaagcagagccacgcaacgtcttgacatctgtacctattttgggccaaaaatcgagacc caccagctcgtcctaccttacatgtgaagatcttagcccacaatcctactgttttactagtattactgcacagctgtcatcacg agtcctcggttgcttgtgaaacccagctcagctcctgagcacatgcagtaacgccgactcggcgtcatttcgccacaccca atttggacctgagggatgctggaagctgctgagcagatcccgttaccgattcatggcactactacatccatacgcagcaa acatgggcttgggcttggcttctcaatgcaaaattgcccgcaaaagtcccggcattgtcgatgcagagatgcagatttcag cgggcgattctagggtagggcgactactactactaataccacctagtcagtatgtatctagcaccggaggctaggcggtta gtggacgggaacctggtcattccatcgcaaccaggatcccgcacttcgttgcgcttctgccccacggggcgggagttgg cagaggcagaatgcggagcagcccttgtctgccctggccggggcctgttgaagcaagcagacgagagcagagcgg ttaaaaaacaataattaacacttaacaatacaaaaacaaacaaaaatcccattaaaccaaaactaaacTGACTTC

CATCCACACCTTCGATCCCAACCTTGGCTGTGACGCAGGCACCTTCCAGCCATGC

AGTGACAAAGCGCTCTCCAACCTCAAGGTTGTTGTCGACTCCTTCCGCTCCATCTA

CGGCGTGAACAAGGGCATTCCTGCCGGTGCTGCCGTCGCCATTGGCCGGTATGC

AGAGGATGTGTACTACAACGGCAACCCTTGGTATCTTGCTACATTTGCTGCTGCCG

AGCAGCTGTACGATGCCATCTACGTCTGGAAGAAGACGGGCTCCATCACGGTGAC

CGCCACCTCCCTGGCCTTCTTCCAGGAGCTTGTTCCTGGCGTGACGGCCGGGAC

CTACTCCAGCAGCTCTTCGACCTTTACCAACATCATCAACGCCGTCTCGACATACG

CCGATGGCTTCCTCAGCGAGGCTGCCAAGTACGTCCCCGCCGACGGTTCGCTGG

CCGAGCAGTTTGACCGCAACAGCGGCACTCCGCTGTCTGCGCTTCACCTGACGT

GGTCGTACGCCTCGTTCTTGACAGCCACGGCCCGTCGGGCTGGCATCGTGCCCC

CCTCGTGGGCCAACAGCAGCGCTAGCACGATCCCCTCGACGTGCTCCGGCGCGT

CCGTGGTCGGATCCTACTCGCGTCCCACCGCCACGTCATTCCCTCCGTCGCAGAC

GCCCAAGCCTGGCGTGCCTTCCGGTACTCCCTACACGCCCCTGCCCTGCGCGAC

CCCAACCTCCGTGGCCGTCACCTTCCACGAGCTCGTGTCGACACAGTTTGGCCAG

ACGGTCAAGGTGGCGGGCAACGCCGCGGCCCTGGGCAACTGGAGCACGAGCGC

CGCCGTGGCTCTGGACGCCGTCAACTATGCCGATAACCACCCCCTGTGGATTGG

GACGGTCAACCTCGAGGCTGGAGACGTCGTGGAGTACAAGTACATCAATGTGGG

CCAAGATGGCTCCGTGACCTGGGAGAGTGATCCCAACCACACTTACACGGTTCCT

GCGGTGGCTTGTGTGACGCAGGTTGTCAAGGAGGACACCTGGCAGTCGTAAtgaat cggcaaggggtagtactagtagacttgtagtctgcc
```

Additional Embodiments

Figure 6A:
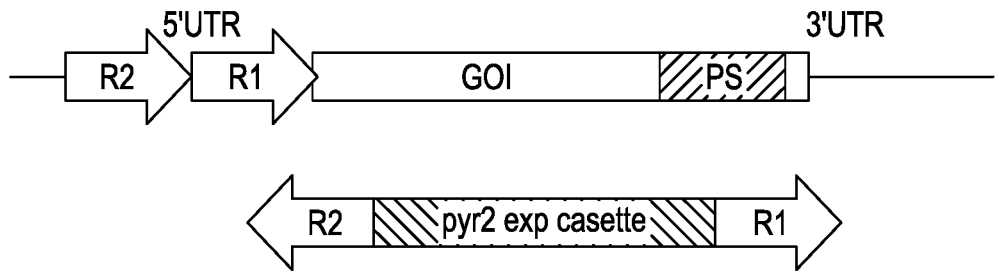
FIGS. 6A-6C. Insertion-orientation-independent deletion cassette design (donor DNA) based on the position of target site (or protospacer, "PS") in a gene of interest (GOI). The genomic sequence is shown at the top of each of FIGS. 6A-6C, while the donor DNA is shown at the bottom of each of these figures. Donor DNA designs are shown for: PS near the C-terminus/3' end of the GOI (FIG. 6A); PS in or near the middle of the GOI (FIG. 6B); PS near the N-terminus/5' end of the GOI (FIG. 6C). UTR=untranslated; GOI=gene of interest; R1=repeat sequence 1; R2=repeat sequence 2; pyr2 exp cassette=expression cassette for pyr2 gene.
Figure 6B:
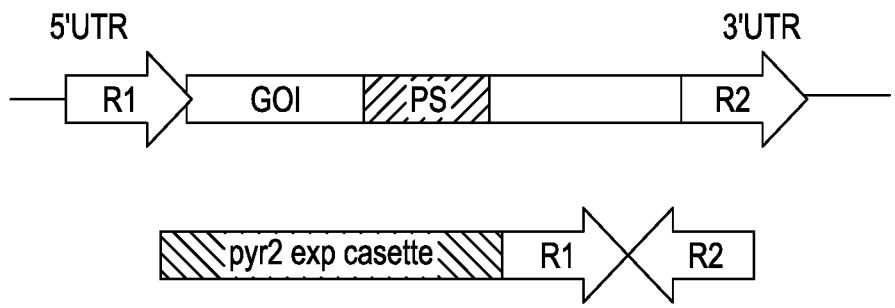
Figure 6C:
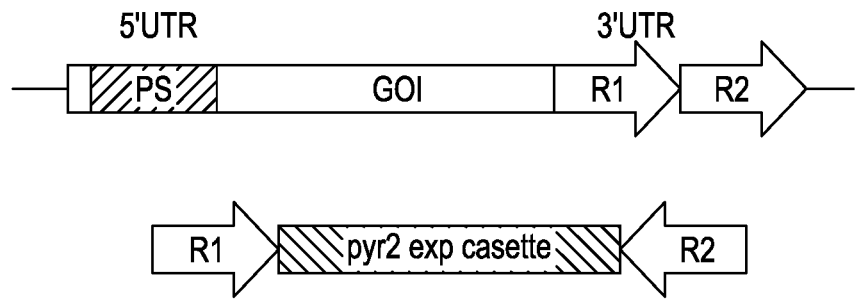

It is noted here that in the Examples above, the donor DNA (SEQ ID NO:30) was designed to function in the loop-out reaction when inserted under only one orientation. Considering the fact that the in vivo DNA fragment insertion could occur in either orientation, one could design donor DNAs that would function in both conditions. FIGS. 6A-6C provide three alternative donor DNA designs that would function in the loop-out reaction regardless of the orientation of its insertion at the target site (indicated as "PS" in each of FIGS. 6A-6C). These three examples of donor DNA configuration are based on the position of target site (or protospacer, PS).

In FIG. 6A, the target site is near the 3' end of the gene of interest (GOI). As such, the donor DNA includes two different repeat sequences (R1 and R2) derived from genomic sequences that are upstream (5') of the GOI (the directions of the arrows indicate the 5' to 3' orientation of the repeat sequences). The R1 and R2 repeat sequences in the donor DNA flank the pyr2 expression cassette and are oriented in a head to head configuration, with the pyr2 expression cassette in between. (It is noted that any desired detectable/selectable marker can be employed. Also, while the general orientation of the elements shown in FIGS. 6A-6C is important, these elements need not be in the precise locations with respect to a GOI. For example, the elements can be present in a non-coding region, e.g., an enhancer element.)

In FIG. 6B, the target site is near the center of the GOI. As such, the donor DNA includes two different repeat sequences (R1 and R2) oriented at the 3' end of the donor DNA in a tail to tail configuration. The genomic R1 site is present in the upstream of the GOI and the genomic R2 sequence is downstream of the GOI.

In FIG. 6C, the target site is near the 5' end of the gene of interest (GOI). As such, the donor DNA includes two different repeat sequences (R1 and R2) derived from genomic sequences that are downstream (3') of the GOI. The R1 and R2 repeat sequences in the donor DNA flank the pyr2 expression cassette and are oriented in a tail to tail configuration, with the pyr2 expression cassette in between.

In each of the scenarios in FIGS. 6A-6C, insertion of the donor DNA in either orientation will allow for loop-out of the pyr2 expression cassette and a significant region of the targeted GOI. Specifically, insertion of the donor DNA in either orientation will generate direct repeat sequences, either R1:R1 or R2:R2, that will function to loop-out the desired region.

In the present disclosure, the application of SpyCas9 mediated DNA fragment insertion at a desired target site, followed by the downstream loop-out via a recombination event between repeat sequences, successfully deleted the TrGA gene in *T. reesei*. While the method described above uses purified SpyCas9 enzyme and in vitro synthesized sgRNA to significantly reduce their continuous function, methods that employ either recombinant DNA encoded Cas and/or guide RNAs under transient transformation conditions can also be used (i.e., where non-stable transformants are selected for). Application of the teachings of the present disclosure enable highly efficient and sequence specific genome modification that can be employed for a wide range of desired outcomes.

Although the foregoing compositions and methods have been described in some detail by way of illustration and example for purposes of clarity of understanding, it is readily apparent to those of ordinary skill in the art in light of the teachings herein that certain changes and modifications may be made thereto without departing from the spirit or scope of the appended claims.

Accordingly, the preceding merely illustrates the principles of the present compositions and methods. It will be appreciated that those skilled in the art will be able to devise various arrangements which, although not explicitly described or shown herein, embody the principles of the present compositions and methods and are included within its spirit and scope. Furthermore, all examples and conditional language recited herein are principally intended to aid the reader in understanding the principles of the present compositions and methods and the concepts contributed by the inventors to furthering the art, and are to be construed as being without limitation to such specifically recited examples and conditions. Moreover, all statements herein reciting principles, aspects, and embodiments of the present compositions and methods as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present compositions and methods, therefore, is not intended to be limited to the exemplary embodiments shown and described herein.

Sequences:

```
SEQ ID NO: 1
Streptococcus pyogenes Cas9, no NLS (encoded by SEQ ID NO: 8)
MDKKYSIGLDIGTNSVGWAVITDEYKVPSKKFKVLGNTDRHSIKKNLIGALLFDSGETA
EATRLKRTARRRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGHFLIEGDLNPDN
SDVDKLFIQLVQTYNQLFEENPINASGVDAKAILSARLSKSRRLENLIAQLPGEKKNGLF
GNLIALSLGLTPNFKSNFDLAEDAKLQLSKDTYDDDLDNLLAQIGDQYADLFLAAKNLS
DAILLSDILRVNTEITKAPLSASMIKRYDEHHQDLTLLKALVRQQLPEKYKEIFFDQSKN
GYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITP
WNFEEVVDKGASAQSFIERMTNFDKNLPNEKVLPKHSLLYEYFTVYNELTKVKYVTEG
MRKPAFLSGEQKKAIVDLLFKTNRKVTVKQLKEDYFKKIECFDSVEISGVEDRFNASLG
TYHDLLKIIKDKDFLDNEENEDILEDIVLTLTLFEDREMIEERLKTYAHLEDDKVMKOLKR
RRYTGWGRLSRKLINGIRDKOSGKTILDFLKSDGFANRNFMOLIHDDSLTFKEDIQKAQ
VSGQGDSLHEHIANLAGSPAIKKGILQTVKVVDELVKVMGRHKPENIVIEMARENOTTO
KGQKNSRERMKRIEEGIKELGSOILKEHPVENTQLQNEKLYLYYLONGRDMYVDQELD
INRLSDYDVDHIVPQSFLKDDSIDNKVLTRSDKNRGKSDNVPSEEVVKKMKNYWRQLL
NAKLITORKFDNLTKAERGGLSELDKAGFIKROLVETRQITKHVAQILDSRMNTKYDEN
DKLIREVKVITLKSKLVSDFRKDFQFYKVREINNYHHAHDAYLNAVVGTALIKKYPKLES
EFVYGDYKVYDVRKMIAKSEQEIGKATAKYFFYSNIMNFFKTEITLANGEIRKRPLIETN
GETGEIVWDKGRDFATVRKVLSMPQVNIVKKTEVQTGGFSKESILPKRNSDKLIARKK
DWDPKKYGGFDSPTVAYSVLVVAKVEKGKSKKLKSVKELLGITIMERSSFEKNPIDFLE
AKGYKEVKKDLIIKLPKYSLFELENGRKRMLASAGELQKGNELALPSKYVNFLYLASHY
EKLKGSPEDNEQKQLFVEQHKHYLDEIIEQ1SEFSKRVILADANLDKVLSAYNKHRDKPI
REQAENIIHLFTLTNLGAPAAFKYFDTTIDRKRYTSTKEVLDATLIHQSITGLYETRIDLSQ
LGGD SEQ ID NO: 2
Streptococcus thermophilus LMD-9 Cas9
MTKPYSIGLDIGTNSVGWAVTTDNYKVPSKKMKVLGNTSKKYIKKNLLGVLLFDSGITA
EGRRLKRTARRRYTRRRNRILYLQEIFSTEMATLDDAFFORLDDSFLVPDDKRDSKYPI
FGNLVEEKAYHDEFPTIYHLRKYLADSTKKADLRLVYLALAHMIKYRGHFLIEGEFNSK
NNDIQKNFQDFLDTYNAIFESDLSLENSKQLEEIVKDKISKLEKKDRILKLFPGEKNSGIF
SEFLKLIVGNQADFRKCFNLDEKASLHFSKESYDEDLETLLGYIGDDYSDVFLKAKKLY
```

```
Sequences:
DAILLSGFLTVTDNETEAPLSSAMIKRYNEHKEDLALLKEYIRNISLKTYNEVFKDDTKN
GYAGYIDGKTNQEDFYVYLKKLLAEFEGADYFLEKIDREDFLRKQRTFDNGSIPYQIHL
QEMRAILDKOAKFYPPLAKNKERIEKILTFRIPYYVGPLARGNSDFAWSIRKRNEKITPW
NFEDVIDKESSAEAFINRMTSFDLYLPEEKVLPKHSLLYETFNVYNELTKVRFIAESMRD
YQFLDSKQKKDIVRLYFKDKRKVTDKDIIEYLHAIYGYDGIELKGIEKQFNSSLSTYHDLL
NIIINDKEFLDDSSNEAIIEEIIHTLTIFEDREMIKQRLSKFENIFDKSVLKKLSRRHYTGWG
KLSAKLINGIRDEKSGNTILDYLIDDGISNRNFMQLIHDDALSFKKKIQKAQIIGDEDKGNI
KEVVKSLPGSPAIKKGILQSIKIVDELVKVMGGRKPESIVVEMARENQYTNQGKSNSQQ
RLKRLEKSLKELGSKILKENIPAKLSKIDNNALQNDRLYLYYLQNGKDMYTGDDLDIDRL
SNYDIDHIIPQAFLKDNSIDNKVLVSSASNRGKSDDVPSLEVVKKRKTFWYOLLKSKLIS
ORKFDNLTKAERGGLSPEDKAGFIQRQLVETROITKHVARLLDEKFNNKKDENNRAVR
TVKIITLKSTLVSQFRKDFELYKVREINDFHHAHDAYLNAVVASALLKKYPKLEPEFVYG
DYPKYNSFRERKSATEKVYFYSNIMNIFKKSISLADGRVIERPLIEVNEETGESVWNKE
SDLATVRRVLSYPQVNVVKKVEEQNHGLDRGKPKGLFNANLSSKPKPNSNENLVGAK
EYLDPKKYGGYAGISNSFTVLVKGTIEKGAKKKITNVLEFQGISILDRINYRKDKLNFLLE
KGYKDIELIIELPKYSLFELSDGSRRMLASILSTNNKRGEIHKGNQIFLSQKFVKLLYHAK
RISNTINENHRKYVENHKKEFEELFYYILEFNENYVGAKKNGKLLNSAFQSWQNHSIDE
LCSSFIGPTGSERKGLFELTSRGSAADFEFLGVKIPRYRDYTPSSLLKDATLIHQSVTGL
YETRIDLAKLGEG SEQ ID NO: 3
Streptococcus mutans UA159 Cas9
MKKPYSIGLDIGTNSVGWAVVTDDYKVPAKKMKVLGNTDKSHIEKNLLGALLFDSGNT
AEDRRLKRTARRRYTRRRNRILYLQEIFSEEMGKVDDSFFHRLEDSFLVTEDKRGERH
PIFGNLEEEVKYHENFPTIYHLRQYLADNPEKVDLRLVYLALAHIIKFRGHFLIEGKFDTR
NNDVORLFQEFLAVYDNTFENSSLQEQNVQVEEILTDKISKSAKKDRVLKLFPNEKSN
GRFAEFLKLIVGNQADFKKHFELEEKAPLQFSKDTYEEELEVLLAQIGDNYAELFLSAK
KLYDSILLSGILTVTDVGTKAPLSASMIQRYNEHQMDLAQLKQFIRQKLSDKYNEVFSD
VSKDGYAGYIDGKTNQEAFYKYLKGLLNKIEGSGYFLDKIEREDFLRKQRTFDNGSIPH
QIHLQEMRAIIRRQAEFYPFLADNQDRIEKLLTFRIPYYVGPLARGKSDFAWLSRKSAD
KITPWNFDEIVDKESSAEAFINRMTNYDLYLPNQKVLPKHSLLYEKFTVYNELTKVKYK
TEQGKTAFFDANMKQEIFDGVFKVYRKVTKDKLMDFLEKEFDEFRIVDLTGLDKENKV
FNASYGTYHDLCKILDKDFLDNSKNEKILEDIVLTLTLFEDREMIRKRLENYSDLLTKEQ
VKKLERRHYTGWGRLSAELIHGIRNKESRKTILDYLIDDGNSNRNFMQLINDDALSFKE
EIAKAQVIGETDNLNQVVSDIAGSPAIKKGILQSLKIVDELVKIMGHQPENIVVEMAREN
QFTNQGRRNSQQRLKGLTDSIKEFGSQILKEHPVENSQLQNDRLFLYYLQNGRDMYT
GEELDIDYLSQYDIDHIIPQAFIKDNSIDNRVLTSSKENRGKSDDVPSKDVVRKMKSYW
SKLLSAKLITORKFDNLTKAERGGLTDDDKAGFIKRQLVETRUTKHVARILDERFNTET
DENNKKIRQVKIVTLKSNLVSNFRKEFELYKVREINDYHHAHDAYLNAVIGKALLGVYP
QLEPEFVYGDYPHFHGHKENKATAKKFFYSNIMNFFKKDDVRTDKNGEIIWKKDEHIS
NIKKVLSYPQVNIVKKVEEQTGGFSKESILPKGNSDKLIPRKTKKFYWDTKKYGGFDSP
IVAYSILVIADIEKGKSKKLKTVKALVGVTIMEKMTFERDPVAFLERKGYRNVQEENIIKL
PKYSLFKLENGRKRLLASARELQKGNEIVLPNHLGTLLYHAKNIHKVDEPKHLDYVDKH
KDEFKELLDVVSNFSKKYTLAEGNLEKIKELYAMINGEDLKELASSFINLLTFTAIGAPA
TFKFFDKNIDRKRYTSTTEILNATLIHQSITGLYETRIDLNKLGGD SEQ ID NO: 4
Campylobacter jejuni Cas9
MARILAFDIGISSIGWAFSENDELKDCGVRIFTKVENPKTGESLALPRRLARSARKRLAR
RKARLNHLKHLIANEFKLNYEDYQSFDESLAKAYKGSLISPYELRFRALNELLSKQDFA
RVILHIAKRRGYDDIKNSDDKEKGAILKAIKONEEKLANYQSVGEYLYKEYFQKFKENS
KEFTNVRNKKESYERCIAQSFLKDELKLIFKKQREFGFSFSKKFEEEVLSVAFYKRALK
DFSHLVGNCSFFTDEKRAPKNSPLAFMFVALTRIINLLNNLKNTEGILYTKDDLNALLNE
VLKNGTLTYKQTKKLLGLSDDYEFKGEKGTYFIEFKKYKEFIKALGEHNLSQDDLNEIAK
DITLIKDEIKLKKALAKYDLNQNQIDSLSKLEFKDHLNISPFKALKLVTPLMEGKKYDEAC
NELNLKVAINEDKKDFLPAFNETYYKDEVTNPVVLRAIKEYRKVLNALLKKYGKVHKINI
ELAREVGKNHSQRAKIEKEQNENYKAKKDAELECEKLGLKINSKNILKLRLFKEQKEFC
AYSGEKIKISDLQOEKMLEIDHIYPYSRSFDDSYMNKVLVFTKQNQEKLNQTPFEAFGN
DSAKWQKIEVLAKNLPTKKQKRILDKNYKDKEQKNFKDRNLNDTRYIARLVLNYTKDYL
DFLPLSDDENTKLNDTQKGSKVHVEAKSGMLTSALRHTWGFSAKDRNNHLHHAIDAVI
IAYANNSIVKAFSDFKKEQESNSAELYAKKISELDYKNKRKFFEPFSGFRQKVLDKIDEI
FVSKPERKKPSGALHEETFRKEEEFYQSYGGKEGVLKALELGKIRKVNGKIVKNGDMF
RVDIFKHKKTNKFYAVPIYTMDFALKVLPNKAVARSKKGEIKDWILMDENYEFCFSLYK
DSLILIQTKDMQEPEFVYYNAFTSSTVSLIVSKHDNKFETLSKNQKILFKNANEKEVIAKS
IGIQNLKVFEKYIVSALGEVTKAEFROREDFKK SEQ ID NO: 5
Neisseria meningitides Cas9
MAAFKPNSINYILGLDIGIASVGWAMVEIDEEENPIRLIDLGVRVFERAEVPKTGDSLAM
ARRLARSVRRLTRRRAHRLLRTRRLLKREGVLQAANFDENGLIKSLPNTPWQLRAAAL
DRKLTPLEWSAVLLHLIKHRGYLSQRKNEGETADKELGALLKGVAGNAHALQTGDFRT
PAELALNKFEKESGHIRNQRSDYSHTFSRKDLQAELILLFEKQKEFGNPHVSGGLKEGI
ETLLMTURPALSGDAVQKMLGHCTFEPAEPKAAKNTYTAERFIWLTKLNNLRILEQGS
ERPLTDTERATLMDEPYRKSKLTYAQARKLLGLEDTAFFKGLRYGKDNAEASTLMEM
KAYHAISRALEKEGLKDKKSPLNLSPELQDEIGTAFSLFKTDEDITGRLKDRIQPEILEAL
LKHISFDKFVQISLKALRRIVPLMEQGKRYDEACAEIYGDHYGKKNTEEKIYLPPIPADEI
RNPVVLRALSQARKVINGVVRRYGSPARIHIETAREVGKSFKDRKEIEKRQEENRKDR
```

-continued

Sequences:

EKAAAKFREYFPNFVGEPKSKDILKLRLYEQQHGKCLYSGKEINLGRLNEKGYVEIDHA
LPFSRTWDDSFNNKVLVLGSENQNKGNOTPYEYFNGKDNSREWQEFKARVETSRFP
RSKKORILLQKFDEDGFKERNLNDTRYVNRFLCQFVADRMRLTGKGKKRVFASNGQI
TNLLRGFWGLRKVRAENDRHHALDAVVVACSTVAMQQKITRFVRYKEMNAFDGKTID
KETGEVLHQKTHFPQPWEFFAQEVMIRVFGKPDGKPEFEEADTLEKLRTLLAEKLSSR
PEAVHEYVTPLFVSRAPNRKMSGQGHMETVKSAKRLDEGVSVLRVPLTQLKLKDLEK
MVNREREPKLYEALKARLEAHKDDPAKAFAEPFYKYDKAGNRTQQVKAVRVEQVQKT
GVWVRNHNG IADNATMVRVDVFEKGDKYYLVPIYSWQVAKGILPDRAVVQG KDEED
WQLIDDSFNFKFSLHPNDLVEVITKKARMFGYFASCHRGTGNINIRIHDLDHKIGKNGIL
EGIGVKTALSFQKYQIDELGKEIRPCRLKKRPPVR

SEQ ID NO: 6
*Francisella tularensis* subsp. *novicida* Cas9
MNFKILPIAIDLGVKNTGVFSAFYQKGTSLERLDNKNGKVYELSKDSYTLLMNNRTARR
HQRRGIDRKQLVKRLFKLIWTEQLNLEWDKDTQQAISFLFNRRGFSFITDGYSPEYLNI
VPEQVKAILMDIFDDYNGEDDLDSYLKLATEQESKISEIYNKLMQKILEFKLMKLCTDIKD
DKVSTKTLKEITSYEFELLADYLANYSESLKTQKFSYTDKQGNLKELSYYHHDKYNIQE
FLKRHATINDRILDTLLTDDLDIWNFNFEKFDFDKNEEKLQNQEDKDHIQAHLHHFVFA
VNKIKSEMASGGRHRSQYFQEITNVLDENNHQEGYLKNFCENLHNKKYSNLSVKNLV
NLIGNLSNLELKPLRKYFNDKIHAKADHWDEQKFTETYCHWILGEWRVGVKDQDKKD
GAKYSYKDLCNELKQKVTKAGLVDFLLELDPCRTIPPYLDNNNRKPPKCOSLILNPKFL
DNQYPNWQQYWELKKLOSIONYLDSFETDLKVLKSSKDOPYFVEYKSSNQQ1ASGQ
RDYKDLDARILQFIFDRVKASDELLLNEIYFQAKKLKOKASSELEKLESSKKLDEVIANS
QLSOILKSQHTNGIFEQGTFLHLVCKYYKORQRARDSRLYIMPEYRYDKKLHKYNNTG
RFDDDNOLLTYCNHKPRQKRYQLLNDLAGVLQVSPNFLKDKIGSDDDLFISKWLVEHI
RGFKKACEDSLKIQKDNRGLLNHKINIARNTKGKCEKEIFNLICKIEGSEDKKGNYKHGL
AYELGVLLFGEPNEASKPEFDRKIKKFNSIYSFAQIQQIAFAERKGNANTCAVCSADNA
HRMQQIKITEPVEDNKDKIILSAKAQRLPAIPTRIVDGAVKKMATILAKNIVDDNWQNIKQ
VLSAKHQLHIPIITESNAFEFEPALADVKGKSLKDRRKKALERISPENIFKDKNNRIKEFA
KGISAYSGANLTDGDFDGAKEELDHIIPRSHKKYGTLNDEANLICVTRGDNKNKGNRIF
CLRDLADNYKLKQFETTDDLEIEKKIADTIWDANKKDFKFGNYRSFINLTPQEQKAFRH
ALFLADENPIKQAVIRAINNRNRTFVNGTQRYFAEVLANNIYLRAKKENLNTDKISFDYF
GIPTIGNGRGIAEIROLYEKVDSDIQAYAKGDKPQASYSHLIDAMLAFCIAADEHRNDGS
IGLEIDKNYSLYPLDKNTGEVFTKDIFSQ1KITDNEFSDKKLVRKKAIEGFNTHROMTRD
GIYAENYLPILIHKELNEVRKGYTWKNSEEIKIFKGKKYDIQQLNNLVYCLKFVDKPISIDI
QISTLEELRNILTTNNIAATAEYYYINLKTOKLHEYYIENYNTALGYKKYSKEMEFLRSLA
YRSERVKIKSIDDVKQVLDKDSNFIIGKITLPFKKEWQRLYREWONTTIKDDYEFLKSFF
NVKSITKLHKKVRKDFSLPISTNEGKFLVKRKTWDNNFIYQILNDSDSRADGTKPFIPAF
DISKNEIVEAIIDSFTSKNIFWLPKNIELQKVDNKNIFAIDTSKWFEVETPSDLRDIGIATIQ
YKIDNNSRPKVRVKLDYVIDDDSKINYFMNHSLLKSRYPDKVLEILKQSTIIEFESSGFNK
TIKEMLGMKLAGIYNETSNN SEQ ID NO: 7
*Pasteurella multocida* Cas9
MQTTNLSYILGLDLGIASVGWAVVEINENEDPIGLIDVGVRIFERAEVPKTGESLALSRR
LARSTRRLIRRRAH RLLLAKRFLKREGILSTIDLEKGLPNQAWELRVAGLERRLSAIEW
GAVLLHLIKHRGYLSKRKNESQTNNKELGALLSGVAQNHQLLQSDDYRTPAELALKKF
AKEEGHIRNORGAYTHTFNRLDLLAELNLLFAQQHQFGNPHCKEHIQQYMTELLMWQ
KPALSGEAILKMLGKCTHEKNEFKAAKHTYSAERFVWLTKLNNLRILEDGAERALNEEE
ROLLINHPYEKSKLTYAQVRKLLGLSEQAIFKHLRYSKENAESATFMELKAWHAIRKAL
ENQGLKDTWQDLAKKPDLLDEIGTAFSLYKTDEDIQQYLTNKVPNSVINALLVSLNFDK
FIELSLKSLRKILPLMEQGKRYDQACREIYGHHYGEANQKTSQLLPAIPAQEIRNPVVLR
TLSQARKVINAIIRQYGSPARVHIETGRELGKSFKERREIQKQQEDNRTKRESAVQKFK
ELFSDFSSEPKSKDILKFRLYEQQHGKCLYSGKEINIHRLNEKGYVEIDHALPFSRTWD
DSFNNKVLVLASENQNKGNOTPYEWLQGKINSERWKNFVALVLGSQCSAAKKORLLT
QVIDDNKFIDRNLNDTRYIARFLSNYIQENLLLVGKNKKNVFTPNGQITALLRSRWGLIK
ARENNNRHHALDAIVVACATPSMQQKITRFIRFKEVHPYKIENRYEMVDQESGEIISPH
FPEPWAYFROEVNIRVFDNHPDTVLKEMLPDRPQANHQFVQPLFVSRAPTRKMSGQ
GHMETIKSAKRLAEGISVLRIPLTQLKPNLLENMVNKEREPALYAGLKARLAEFNQDPA
KAFATPFYKQGGQQVKAIRVEQVQKSGVLVRENNGVADNASIVRTDVFIKNNKFFLVPI
YTWQVAKGILPNKAIVAHKNEDEWEEMDEGAKFKFSLFPNDLVELKTKKEYFFGYYIG
LDRATGNISLKEHDGEISKGKDGVYRVGVKLALSFEKYQVDELGKNRQICRPQQRQ
PVR SEQ ID NO: 8
Filamentous fungal cell codon optimized *Streptococcus pyogenes* Cas9-encoding gene; no NLS
atggacaagaagtacagcatcggcctcgacatcggcaccaactcggtgggctgggccgtcatcacggacgaatataa
ggtcccgtcgaagaagttcaaggtcctcggcaatacagaccgccacagcatcaagaaaaacttgatcggcgccctcct
gttcgatagcgg cgagaccgcggaggcgaccaggctcaagaggaccgccaggagacggtacactaggcgcaaga
acaggatctgctacctgcaggagatcttcagcaacgagatggcgaaggtggacgactccttcttccaccgcctggagga
atcattcctggtggaggaggacaagaagcatgagcggcacccaatcttcggcaacatcgtcgacgaggtggcctacca
cgagaagtacccgacaatctaccacctccggaagaaactggtggacagcacagacaaggcggacctccggctcatct
accttgccctcgcgcatatgatcaagttccgcggccacttcctcatcgagggcgacctgaacccggacaactccgacgtg
gacaagctgttcatccagctcgtgcagacgtacaatcaactgttcgaggagaaccccataaacgctagcggcgtggacg
ccaaggccatcctctcggccaggctctcgaaatcaagaaggctggagaaccttatcgcgcagttgccaggcgaaaaga
agaacggcctcttcggcaaccttattgcgctcagcctcggcctgacgccgaacttcaaatcaaacttcgacctcgcggag

```
gacgccaagctccagctctcaaaggacacctacgacgacgacctcgacaacctcctggcccagataggagaccagta
cgcggacctcttcctcgccgccaagaacctctccgacgctatcctgctcagcgacatccttcgggtcaacaccgaaattac
caaggcaccgctgtccgccagcatgattaaacgctacgacgagcaccatcaggacctcacgctgctcaaggcactcgt
ccgccagcagctccccgagaagtacaaggagatcttcttcgaccaatcaaaaaacggctacgcgggatatatcgacgg
cggtgccagccaggaagagttctacaagttcatcaaaccaatcctggagaagatggacggcaccgaggagttgctggt
caagctcaacagggaggacctcctcaggaagcagaggaccttcgacaacggctccatcccgcatcagatccacctgg
gcgaactgcatgccatcctgcggcgccaggaggacttctacccgttcctgaaggataaccgggagaagatcgagaag
atcttgacgttccgcatcccatactacgtgggcccgctggctgcggcaactcccggttcgcctggatgacccggaagtcg
gaggagaccatcacaccctggaactttgaggaggtggtcgataagggcgctagcgctcagagcttcatcgagcgcatg
accaacttcgataaaaacctgcccaatgaaaaagtcctccccaagcactcgctgctctacgagtacttcaccgtgtacaa
cgagctcaccaaggtcaaatacgtcaccgagggcatgcggaagccggcgttcctgagcggcgagcagaagaaggc
gatagtggacctcctcttcaagaccaacaggaaggtgaccgtgaagcaattaaaagaggactacttcaagaaaataga
gtgcttcgactccgtggagatctcgggcgtggaggatcggttcaacgcctcactcggcacgtatcacgacctcctcaagat
cattaaagacaaggacttcctcgacaacgaggagaacgaggacatcctcgaggacatcgtcctcaccctgaccctgttc
gaggaccgcgaaatgatcgaggagaggctgaagacctacgcgcacctgttcgacgacaaggtcatgaaacagctca
agaggcgccgctacactggttggggaaggctgtcccgcaagctcattaatgtgcatcagggacaagcagagcggcaag
accatcctggacttcctcaagtccgacggggttcgccaaccgcaacttcatgcagctcattcacgacgactcgctcacgttc
aaggaagacatccagaaggcacaggtgagcgggcagggtgactccctccacgaacacatcgccaacctggccggct
cgccggccattaaaaagggcatcctgcagacggtcaaggtcgtcgacgagctcgtgaaggtgatgggccggcacaag
cccgaaaatatcgtcatagagatggccagggagaaccagaccacccaaaaagggcagaagaactcgcgcgagcg
gatgaaacggatcgaggagggcattaaagagctcgggtcccagatcctgaaggagcacccgtggaaaatacccag
ctccagaatgaaaagctctacctctactacctgcagaacggccgcgacatgtacgtggaccaggagctggacattaatc
ggctatcggactacgacgtcgaccacatcgtgccgcagtcgttcctcaaggacgatagcatcgacaacaaggtgctcac
ccggtcggataaaaatcggggcaagagcgacaacgtgcccagcgaggaggtcgtgaagaagatgaaaaactactg
gcgccagctcctcaacgcgaaactgatcacccagcgcaagttcgacaacctgacgaaggcggaacgcggtggcttga
gcgaactcgataaggcgggcttcataaaaaggcagctggtcgagacgcgccagatcacgaagcatgtcgcccagatc
ctggacagccgcatgaatactaagtacgatgaaaacgacaagctgatccgggaggtgaaggtgatcacgctgaagtcc
aagctcgtgtcggacttccgcaaggacttccagttctacaaggtccgcgagatcaacaactaccaccacgcccacgacg
cctacctgaatgcggtggtcgggaccgccctgatcaagaagtaccccgaagctggagtcggagttcgtgtacggcgacta
caaggtctacgacgtgcgcaaaatgatcgccaagtccgagcaggagatcggcaaggccacggcaaaatacttcttcta
ctcgaacatcatgaacttcttcaagaccgagatcaccctcgcgaacggcgagatccgcaagcgccccgctcatcgaaac
caacggcgagacgggcgagatcgtctgggataagggccgggatttcgcgacggtccgcaaggtgctctccatgccgca
agtcaatatcgtgaaaaagacggaggtccagacgggcgggttcagcaaggagtccatcctcccgaagcgcaactccg
acaagctcatcgcgaggaagaaggattgggacccgaaaaaatatggcggcttcgacagcccgaccgtcgcatacag
cgtcctcgtcgtggcgaaggtggagaagggcaagtcaaagaagctcaagtccgtgaaggagctgctcgggatcacgat
tatggagcggtcctccttcgagaagaacccgatcgacttcctagaggccaagggatataaggaggtcaagaaggacct
gattattaaactgccgaagtactcgctcttcgagctggaaaacgggccgcaaggatgctcgcctccgccaggcgagttgc
agaagggcaacgagctcgccctcccgagcaaatacgtcaatttcctgtacctcgctagccactatgaaaagctcaaggg
cagcccggaggacaacgagcagaagcagctcttcgtggagcagcacaagcattacctggacgagatcatcgagcag
atcagcgagttctcgaagcgggtgatcctcgccgacgcgaacctggacaaggtgctgtcggcatataacaagcaccgc
gacaaaccaatacgcgaacgaggccgaaaatatcatccacctcttcaccctcaccaacctcggcgctccggcagccttca
agtacttcgacaccacgattgaccggaagcggtacacgagcacgaaggaggtgctcgatgcgacgctgatccaccag
agcatcacagggctctatgaaacacgcatcgacctgagccagctgggcggagac
```

SEQ ID NO: 9
Filamentous fungal cell codon optimized *Streptococcus pyogenes* Cas9-encoding gene; with N- and C-terminal NLS sequences
```
atggcaccgaagaagaagcgcaaggtgatggacaagaagtacagcatcggcctcgacatcggcaccaactcggtgg
gctgggccgtcatcacggacgaatataaggtcccgtcgaagaagttcaaggtcctcggcaatacagacgccacagca
tcaagaaaaacttgatcggcgccctcctgttcgatagcggcgagaccgcggaggcgaccaggctcaagaggaccgcc
aggagacggtacactaggcgcaagaacaggatctgctacctgcaggagatcttcagcaacgagatggcgaaggtgg
acgactccttcttccaccgcctggaggaatcattcctggtggaggaggacaagaagcatgagcggcacccaatcttcgg
caacatcgtcgacgaggtggcctaccacgagaagtacccgacaatctaccacctccggaagaacttaccgacagca
cagacaaggcggacctccggctcatctaccttgccctcgcgcatatgatcaagttccgcggccacttcctcatcgagggc
gacctgaacccggacaactccgacgtggacaagctgttcatccagctcgtgcagacgtacaatcaactgttcgaggaga
accccataaacgctagcggcgtggacgccaaggccatcctctcggccaggctctcgaaatcaagaaggctggagaac
cttatcgcgcagttgccaggcgaaaagaagaacggcctcttcggcaacctttattgcgctcagcctcggcctgacgccga
acttcaaatcaaacttcgacctcgcggaggacgccaagctccagctctcaaaggacacctacgacgacgacctcgaca
acctcctggcccagataggagaccagtacgcggacctcttcctcgccgccaagaacctctccgacgctatcctgctcagc
gacatccttcgggtcaacaccgaaattaccaaggcaccgctgtccgccagcatgattaaacgctacgacgagcaccatc
aggacctcacgctgctcaaggcactcgtccgccagcagctccccgagaagtacaaggagatcttcttcgaccaatcaaa
aaacggctacgcgggatatatcgacggcggtgccagccaggaagagttctacaagttcatcaaaccaatcctggagaa
gatggacggcaccgaggagttgctggtcaagctcaacagggaggacctcctcaggaagcagaggaccttcgacaac
ggctccatcccgcatcagatccacctgggcgaactgcatgccatcctgcggcgccaggaggacttctacccgttcctgaa
ggataaccgggagaagatcgagaagatcttgacgttccgcatcccatactacgtgggcccgctggctgcggcaactcc
cggttcgcctggatgacccggaagtcggaggagaccatcacaccctggaactttgaggaggtggtcgataagggcgct
agcgctcagagcttcatcgagcgcatgaccaacttcgataaaaacctgcccaatgaaaaagtcctccccaagcactcgc
tgctctacgagtacttcaccgtgtacaacgagctcaccaaggtcaaatacgtcaccgagggcatgcggaagccggcgtt
cctgagcggcgagcagaagaaggcgatagtggacctcctcttcaagaccaacaggaaggtgaccgtgaagcaattaa
aagaggactacttcaagaaaatagagtgcttcgactccgtggagatctcgggcgtggaggatcggttcaacgcctcactc
ggcacgtatcacgacctcctcaagatcattaaagacaaggacttcctcgacaacgaggagaacgaggacatcctcgag
gacatcgtcctcaccctgaccctgttcgaggaccgcgaaatgatcgaggagaggctgaagacctacgcgcacctgttcg
acgacaaggtcatgaaacagctcaagaggcgccgctacactggttggggaaggctgtcccgcaagctcattaatggca
tcagggacaagcagagcggcaagaccatcctggacttcctcaagtccgacggggttcgccaaccgcaacttcatgcagc
tcattcacgacgactcgctcacgttcaaggaagacatccagaaggcacaggtgagcgggcagggtgactccctccacg
aacacatcgccaacctggccggctcgccggccattaaaaagggcatcctgcagacggtcaaggtcgtcgacgagctc
gtgaaggtgatgggccggcacaagcccgaaaatatcgtcatagagatggccagggagaaccagaccacccaaaaa
```

```
gggcagaagaactcgcgcgagcggatgaaacggatcgaggagggcattaaagagctcgggtcccagatcctgaag
gagcaccccgtggaaaataccagctccagaatgaaaagctctacctctactacctgcagaacggccgcgacatgtac
gtggaccaggagctggacattaatcggctatcggactacgacgtcgaccagctgccgcagtcgttcctcaaggacg
atagcatcgacaacaaggtgctcacccggtcggataaaaatcggggcaagagcgacaacgtgcccagcgaggaggt
cgtgaagaagatgaaaactactggcgccagctcctcaacgcgaaactgatcacccagcgcaagttcgacaacctga
cgaaggcggaacgcggtggcttgagcgaactcgataaggcgggcttcataaaaaggcagctggtcgagacgcgcca
gatcacgaagcatgtcgcccagatcctggacagccgcatgaatactaagtacgatgaaaacgacaagctgatccgg
aggtgaaggtgatcacgctgaagtccaagctcgtgtcggacttccgcaaggactcccagttctacaaggtccgcgagatc
aacaactaccaccacgccacgacgcctacctgaatgcggtggtcgggaccgccctgatcaagaagtacccgaagct
ggagtcggagttcgtgtacggcgactacaaggtctacgacgtgcgcaaaatgatcgccaagtccgagcaggagatcgg
caaggccacggcaaaatacttcttctactcgaacatcatgaacttcttcaagaccgagatcaccctcgcgaacggcgag
atccgcaagcgcccgctcatcgaaaccaacggcgaggacgggcagatcgtctgggataaggccgggatttcgcgac
ggtccgcaaggtgctctccatgccgcaagtcaatatcgtgaaaaagacggaggtccagacgggcgggttcagcaagg
agtccatcctcccgaagcgcaactccgacaagctcatcgcgaggaagaaggattgggacccgaaaaaatatggcggc
ttcgacagcccgaccgtcgcatacagcgtcctcgtcgtggcgaaggtggagaagggcaagtcaaagaagctcaagtcc
gtgaaggagctgctcgggatcacgattatggagcggtcctccttcgagaagaacccgatcgacttcctagaggccaagg
gatataaggaggtcaag aagg acctgattattaaactgccgaagtactcgctcttcgagctggaaaacggccgcaaga
ggatgctcgcctccgcaggcgagttgcagaagggcaacgagctcgccctcccgagcaaatacgtcaatttcctgtacctc
gctagccactatgaaagctcaagggcagcccggaggacaacgagcagaagcagctcttcgtggagcagcacaag
cattacctggacgagatcatcgagcagatcagcgagttctctgaagcgggtgatcctcgccgacgcgaacctggacaag
gtgctgtcggcatataacaagcaccgcgacaaaccaatacgcgagcaggccgaaaatatcatccacctcttcaccctca
ccaacctcggcgctccggcagccttcaagtacttcgacaccacgattgaccggaagcggtacacgagcacgaaggag
gtgctcgatgcgacgctgatccaccagagcatcacagggctctatgaaacacgcatcgacctgagccagctgggcgga
gacaagaagaagaagctcaagctctag
```

SEQ ID NO: 10
*Streptococcus pyogenes* Cas9 with N- and C-terminal NLS sequences (encoded by
SEQ ID NO: 9)
```
MAPKKKRKVMDKKYSIGLDIGTNSVGWAVITDEYKVPSKKFKVLGNTDRHSIKKNLIGA
LLFDSGETAEATRLKRTARRRYTRRKNRICYLQEIFSNEMAKVDDSFFHRLEESFLVEE
DKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLP
GEKKNGLFGNLIALSLGLTPNFKSNFDLAEDAKLQLSKDTYDDDLDNLLAQIGDQYADL
FLAAKNLSDAILLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRK
SEETITPWNFEEVVDKGASAQSFIERMTNFDKNLPNEKVLPKHSLLYEYFTVYNELTKV
KYVTEGMRKPAFLSGEQKKAIVDLLFKTN RKVTVKQLKEDYFKKIECFDSVEISGVEDR
FNASLGTYHDLLKIIKDKDFLDNEENEDILEDIVLTLTLFEDREMIEERLKTYAHLFDDKV
MKQLKRRRYTGWGRLSRKLINGIRDKQSGKTILDFLKSDGFANRNFMQL1HDDSLTFK
EDIQKAQVSGQGDSLHEHIANLAGSPAIKKGILQTVKVVDELVKVMGRHKPENIVIEMA
RENQTTQKGQKNSRERMKRIEEGIKELGSQILKEHPVENTQLQNEKLYLYYLONGRD
MYVDQELDINRLSDYDVDHIVPQSFLKDDSIDNKVLTRSDKNRGKSDNVPSEEVVKKM
KNYWRQLLNAKLITQRKFDNLTKAERGGLSELDKAGFIKRQLVETRQITKHVAQILDSR
MNTKYDENDKLIREVKVITLKSKLVSDFRKDFQFYKVREINNYHHAHDAYLNAVVGTAL
IKKYPKLESEFVYGDYKVYDVRKMIAKSEQEIGKATAKYFFYSNIMNFFKTEITLANGEI
RKRPLIETNGETGEIVWDKGRDFATVRKVLSMPQVNIVKKTEVQTGGFSKESILPKRN
SDKLIARKKDWDPKKYGGFDSPTVAYSVLVVAKVEKGKSKKLKSVKELLGITIMERSSF
EKNPIDFLEAKGYKEVKKDLIIKLPKYSLFELENGRKRMLASAGELQKGNELALPSKYV
NFLYLASHYEKLKGSPEDNEQKQLFVEQHKHYLDEIIEQISEFSKRVILADANLDKVLSA
YNKHRDKPIREQAENIIHLFTLTNLGAPAAFKYFDTTIDRKRYTSTKEVLDATLIHQSITG
LYETRIDLSQLGGDKKKKLKL
```

SEQ ID NO: 11
Full U6 gene promoter sequence (not including transcription start site)
```
AAAAAACACTAGTAAGTACTTACTTATGTATTATTAACTACTTTAGCTAACTTCTGCA
GTACTACCTAAGAGGCTAGGGGTAGTTTTATAGCAGACTTATAGCTATTATTTTAT
TTAGTAAAGTGCTTTTAAAGTAAGGTCTTTTTTATAGCACTTTTTATTTATTATAATAT
ATATTATATAATAATTTTAAGCCTGGAATAGTAAAGAGGCTTATATAATAATTTATAG
TAATAAAAGCTTAGCAGCTGTAATATAATTCCTAAAGAAACAGCATGAAATGGTATT
ATGTAAGAGCTATAGTCTAAAGGCACTCTGCTGGATAAAAATAGTGGCTATAAGTC
TGCTGCAAAACTACCCCCAACCTCGTAGGTATATAAGTACTGTTTGATGGTAGTCT
ATC
```

SEQ ID NO: 12
Truncated/shorter U6 gene promoter sequence (not including transcription start site)
```
AATTCCTAAAGAAACAGCATGAAATGGTATTATGTAAGAGCTATAGTCTAAAGGCA
CTCTGCTGGATAAAAATAGTGGCTATAAGTCTGCTGCAAAACTACCCCCAACCTCG
TAGGTATATAAGTACTGTTTGATGGTAGTCTATC
```

SEQ ID NO: 13
N-terminal His6 tag/thrombin/S•Tag ™/enterokinase region polynucleotide sequence
(with start codon); encodes SEQ ID NO: 18
```
atgcaccatcatcatcatcattcttctggtctggtgccacgcggttctggtatgaaagaaaccgctgctgctaaattcgaacg
ccagcacatggacagcccagatctgggtaccgacgacgacgacaaggccatggcc
```

SEQ ID NO: 14
SV40 NLS coding sequence (encodes SEQ ID NO: 19)
ccaaaaaagaaacgcaaggtt SEQ ID NO: 15
E. coli codon-optimized Cas9 gene (no stop codon)
atggataaaaaatacagcattggtctggatatcggaaccaacagcgttgggtgggcagtaataacagatgaatacaaa
gtgccgtcaaaaaaatttaaggttctggggaatacagatcgccacagcataaaaaagaatctgattggggcattgctgttt
gattcgggtgagacagctgaggccacgcgtctgaaacgtacagcaagaagacgttacacacgtcgtaaaaatcgtattt
gctacttacaggaaattttttctaacgaaatggccaaggtagatgatagtttcttccatcgtctcgaagaatcttttctggttgag
gaagataaaaaacgaacgtcaccctatctttggcaatatcgtggatgaagtggcctatcatgaaaaatacctacgatt
tatcatcttcgcaagaagttggttgatagtacggacaaagcggatctgcgtttaatctatcttgcgttagcgcacatgatcaa
atttcgtggtcatttcttaattgaaggtgatctgaatcctgataactctgatgtggacaaattgttatacaattagtgcaaaccta
taatcagctgttcgaggaaaacccccattaatgcctctggagttgatgccaaagcgattttaagcgcgagactUctaagtcc
cggcgtctggagaatctgatcgcccagttaccagggaaaagaaaaatggctctgtttggtaatctgattgccctcagtctgg
ggcttaccccgaacttcaaatccaattttgacctggctgaggacgcaaagctgcagctgagcaaagatacttatgatgatg
acctcgacaatctgctcgcccagattggtgaccaatatgcggatctgtttctggcagcgaagaatctttcggatgctatcttgc
tgtcggatattctgcgtgttaataccgaaatcaccaaagcgcctctgtctgcaagtatgatcaagagatacgacgagcacc
accaggacctgactcttcttaaggcactggtacgccaacagcttccggagaaatacaaagaaatattcttcgaccagtcc
aagaatggttacgcgggctacatcgatggtggtcatcacaggaagagttctataaatttattaaaccaatccttgagaaa
atggatggcacggaagagttacttgttaaacttaaccgcgaagacttgcttagaaagcaacgtacattcgacaacggctc
catcccacaccagattcatttaggtgaacttcacgccatcttgcgcagacaagaagatttctatcccttcttaaagacaatc
gggagaaaatcgagaagatcctgacgttccgcattccctatatgtcggtgccctggcacgtggtaattctcggtttgcctgg
atgacgcgcaaaagtgaggaaaccatcaccccttggaactttgaagaagtcgtggataaaggtgctagcgcgcagtcttt
tatagaaagaatgacgaacttcgataaaaacttgcccaacgaaaaagtcctgcccaagcactctcttttatatgagtacttt
actgtgtacaacgaactgactaaagtgaaatacgttacggaaggtatgcgcaaacctgcctttcttagtggcgagcagaa
aaaagcaattgtcgatcttctcttaaaacgaatcgcaaggtaactgtaaaacgctgaaggaagattatttcaaaaagat
cgaatgctttgattctgtcgagatctcgggtgtcgaagatcgtttcaacgcttccttagggacctatcatgatttgctgaagata
ataaaagacaaagactttctcgacaatgaagaaaatgaagatattctggaggatattgttttgaccttgaccttattcgaag
atagagagatgatcgaggagcgcttaaaaacctatgcccacctgtttgatgacaaagtcatgaagcaattaaagcgccg
cagatatacggggtggggccgcttgagccgcaagttgattagaggtattagagacaagcagacgagcgaaaaactatcct
ggatttcctcaaatctgacggatttgcgaaccgcaatttttatgcagcttatacatgatgattcgcttacattcaaagaggatatt
cagaaggctcaggtgtctgggcaaggtgattcactccacgaacatatagcaaatttggccggctctcctgcgattaagaa
ggggatcctgcaaacagttaaagttgtggatgaacttgtaaaagtaatgggccgccacaagccggagaatatcgtgata
gaaatggcgcgcgagaatcaaacgacacaaaaaggtcaaaagaacctcaagagagagaatgaagcgcattgagga
ggggataaaggaacttggatctcaaattctgaaagaacatccagttgaaaacactcagctgcaaaatgaaaaattgtac
ctgtactacctgcagaatgggaagagacatgtacgtggatcaggaattggatatcaatagactctcggactatgacgtagat
cacattgtccctcagagcttcctcaaggatgattctatagataataaagtacttacgagatcggacaaaaatcgcggtaaat
cggataacgtccccatcggaggaagtcgttaaaaagatgaaaaactattggcgtcaactgctgaacgccaagctgatcac
acagcgtaagtttgataatctgactaaagccgaacgcggtggtctttagtgaactcgataaagcaggatttataaaacggc
agttagtagaaacgcgccaaattacgaaacacgtggctcagatcctcgattctagaatgaatacaaagtacgatgaaaa
cgataaactgatccgtgaagtaaaagtcattaccttaaaatctaaacttgtgtccgatttccgcaaagattttcagttttacaa
ggtccgggaaatcaataactatcaccatgcacatgatgcatatttaaatgcggttgtaggcacggcccttattaagaaatac
cctaaactcgaaagtgagttttgtttatggggattataaagtgatgcgctgctcgcaaaatgatcgcgaaatcagaacaggaa
atcggtaaggctaccgctaaatacttttttttattccaacattatgaattttttaagaccgaaataactctcgcgaatggtgaaat
ccgtaaacggcctcttatagaaaccaatggtgaaacgggagaaatcgtttgggataaaggtcgtgactttgccaccgttcg
taaagtcctctcaatgccgcaagttaacattgtcaagaagacggaagttcaaacaggggggattctccaaagaatctatcct
gccgaagcgtaacagtgataaacttattgccagaaaaaaagattgggatccaaaaaatacgaggctttgattcccct
accgtcgcgtatagtgtgctggtggttgctaaagtcgagaaagggaaaagcaagaaattgaaatcagttaaagaactgc
tgggtattacaattatggaaagatcgtcctttgagaaaaatccgatcgacttttagaggccaaggggtataaggaagtga
aaaaagatctcatcatcaaattaccgaagtatagtctttttgagctggaaaacggcagaaaaagaatgctggcctccgcg
ggcagttacagaagggaaatgagctggcgctgccttccaaatatgttaattttctgtacctttgccagtcattatgagaaact
gaagggcagccccgaagataacgaacagaaaacaattattcgtgaacagcataagcactatttagatgaaattatga
gcaaattagtgaatttttctaagcgcgttatcctcgcggatgctaatttagacaaagtactgtcagcttataataaacatcggg
ataagccgattagagaacaggccgaaaatatcattcatttgtttaccttaaccaaccttggagcaccagctgccttcaaata
tttcgataccacaattgatcgtaaacggtatacaagtacaaaagaagtcttggacgcaaccctcattcatcaatctattactg
gattatatgagacacgcattgatctttcacagctgggcggagac SEQ ID NO: 16
BLR2 nuclear localization signal coding sequence (encodes SEQ ID NO: 20)
aagaagaaaaaactgaaactg SEQ ID NO: 17
The nucleotide sequence of the SpyCas9 synthetic gene in plasmid pET30a-SpyCas9.
The oligonucleotides encoding the N-terminal His6 tag, the SV40 nuclear localization
signal, and the BLR nuclear localization signal are shown in bold underline, italic
underline, and underlined, respectively.
atgcaccatcatcatcatcattcttctggtctggtgccacgcggttctggtatgaaagaaaccgctgctgctaaattcgaac
gccagcacatggacagcccagatctgggtaccgacgacgacgacaaggccatggcc*ccaaaaaagaaacgcaag*
*gtt*atggataaaaaatacagcattggtctggatatcggaaccaacagcgttgggtgggcagtaataacagatgaataca
aagtgccgtcaaaaaaatttaaggttctggggaatacagatcgccacagcataaaaaagaatctgattggggcattgctg
tttgattcgggtgagacagctgaggccacgcgtctgaaacgtacagcaagaagacgttacacacgtcgtaaaaatcgtat
ttgctacttacaggaaattttttctaacgaaatggccaaggtagatgatagtttcttccatcgtctcgaagaatcttttctggtga
ggaagataaaaaacgaacgtcaccctatctttggcaatatcgtggatgaagtggcctatcatgaaaaatacccctacga
tttatcatcttcgcaagaagttggttgatagtacggacaaagcggatctgcgtttaatctatcttgcgttagcgcacatgatca
aatttcgtggtcatttcttaattgaaggtgatctgaatcctgataactctgatgtggacaaattgttatacaattagtgcaaacct -continued Sequences:

```
ataatcagctgttcgaggaaaaccccattaatgcctctggagttgatgccaaagcgattttaagcgcgagactttctaagtc
ccggcgtctggagaatctgatcgcccagttaccaggggaaaagaaaaatggtctgtttggtaatctgattgccctcagtctg
gggcttaccccgaacttcaaatccaattttgacctggctgaggacgcaaagctgcagctgagcaaagatacttatgatgat
gacctcgacaatctgctcgcccagattggtgaccaatatgcggatctgtttctggcagcgaagaatctttcggatgctatctt
gctgtcggatattctgcgtgttaataccgaaatcaccaaagcgcctctgtctgcaagtatgatcaagagatacgacgagca
ccaccaggacctgactcttcttaaggcactggtacgccaacagcttccggagaaatacaaagaaatattcttcgaccagt
ccaagaatggttacgcgggctacatcgatggtggtgcatcacaggaagagttctataaatttattaaaccaatccttgaga
aaatggatggcacggaagagttacttgttaaacttaaccgcgaagacttgcttagaaagcaacgtacattcgacaacgg
ctccatcccacaccagattcatttaggtgaacttcacgccatcttgcgcagacaagaagatttctatcccttcttaaaagaca
atcgggagaaaatcgagaagatcctgacgttccgcattccctattatgtcggtccctggcacgtggtaattctcggtttgcct
ggatgacgcgaaagtgaggaaaccatcaccccttggaactttgaagaagtcgtggataaaggtgctagcgcgcagt
cttttatagaaagaatgacgaacttcgataaaaacttgcccaaccgaaaaagtcctgcccaagcactctctctttatatgagta
ctttactgtgtacaacgaactgactaaagtgaaatacgttacggaaggtatgcgcaaacctgcctttcttagtggcgagcag
aaaaaagcaattgtcgatcttctctttaaaacgaatcgcaaggtaactgtaaaacagctgaaggaagattatttcaaaaag
atcgaatgctttgattctgtcgagatctcgggtgtcgaagatcgtttcaacgcttccttagggacctatcatgatttgctgaagat
aataaaagacaaagactttctcgacaatgaagaaaatgaagatattctggaggatattgttttgaccttgaccttattcgaa
gatagagagatgatcgaggagcgcttaaaaacctatgcccacctgtttgatgacaaagtcatgaagcaattaaagcgcc
gcagatatacggggtgggccgcttgagccgcaagttgattaacggtattagagacaagcagagcggaaaaactatcc
tggatttcctcaaatctgacggatttgcgaaccgcaattttatgcagcttatacatgatgattcgcttacattcaaagaggatat
tcagaaggctcaggtgtctgggcaaggtgattcactccacgaacatatgcaaattggccggctctcctgcgattaagaa
ggggatcctgcaaacagttaaagttgtggatgaacttgtaaaagtaatgggccgccacaagccggagaatatcgtgata
gaaatggcgcgcgagaatcaaacgacacaaaaggtcaaaagaactcaagagagagaatgaagcgcattgagga
ggggataaaggaacttggatctcaaattctgaaagaacatccagttgaaaacactcagctgcaaaatgaaaaattgtac
ctgtactacctgcagaatggaagagacatgtacgtggatcgggaatcggatatcctcggactatgacgtagat
cacattgtccctcagagcttcctcaaggatgattctatagataataaagtacttacgagatcggacaaaaatcgcggtaaat
cggataacgtcccatcggaggaagtcgttaaaaagatgaaaaactattggcgtcaactgctgaacgccaagctgatcac
acagcgtaagtttgataatctgactaaagccgaacgcggtggtcttagtgaactcgataaagcaggatttataaacggc
agtagtagaaacgcgccaaattacgaaacacgtggctcagatcctcgattctagaatgaatacaaagtacgatgaaaa
cgataaaactgatccgtgaagtaaaagtcattaccttaaaatctaaacttgtgtccgatttccgcaaagattttcagtttttacaa
ggtccgggaaatcaataactatccaccatgcacatgatgcatattaaatgcggttgtaggcacggcccttattaagaaatac
cctaaactcgaaagtgagtttgtttatggggattataaagtgtatgacgttcgcaaatgatcgcgaaatcagaacaggaa
atcggtaaggctaccgctaaatacttttttttattccaacattatgattgaatttttttaagaccgaaataactctcgcgaatggtgaaat
ccgtaaacggcctcttatagaaaccaatggtgaaacgggagaaatcgtttgggataaaggtcgtgactttgccaccgttcg
taaagtcctctcaatgccgcaagttaacattgtcaagaagacggaagttcaaacaggggggattctccaaagaatctatcct
gccgaagcgtaacagtgataaacttattgccagaaaaaaagattgggatccaaaaaaatacggaggctttgattcccct
accgtcgcgtatagtgtgctggtggttgctaaagtcgagaaagggaaaagcaagaaattgaaatcagttaaagaactgc
tgggtattacaattatggaaagatcgtccttttgagaaaaatccgatcgactttttagaggccaaggggtataaggaagtga
aaaaagatctcatcatcaaattaccgaagtatagtctttttgagctggaaaacggcagaaaaagaatgctggcctccgcg
ggcgagttcagaagggaaatgagctggcgctgccttccaaatatgttaattttctgtaccttgccagtcattatgagaaact
gaagggcagccccgaagataacgaacagaaacaattattcgtggaacagcataagcactatttagatgaaattataga
gcaaattagtgaattttctaagcgcgttatcctcgcggatgctaattcaaagaagtactgtcagctcagcttataatcaaacatcggg
ataagccgattagagaacaggccgaaaatatcattcatttgtttaccttaaccaacctggagcaccagctgccttcaaata
tttcgataccacaattgatcgtaaacggtatacaagtacaaaagaagtcttggacgcaaccctcattcatcaatctattactg
gattatatgagacacgcattgatctttcacagctgggcggagacaagaagaaaaaactgaaactg
```

SEQ ID NO: 18
N-terminal His6 tag/thrombin/S•Tag ™/enterokinase region amino acid sequence
(with start methionine)
Mhhhhhhssglvprgsgmketaaakferqhmdspdlgtddddkama

SEQ ID NO: 19
SV40 NLS
PKKKRKV

SEQ NO: 20
T. reesei blr2 (blue light regulator 2) gene NLS
KKKKLKL

SEQ ID NO: 21
The amino acid sequence of the SpyCas9 protein expressed from plasmid pET30a-
SpyCas9. The N-terminal His6 tag, the SV40 nuclear localization signal, and the BLR
nuclear localization signal are shown in bold underline, italic underline, and underlined,
respectively.
mhhhhhhssglvprgsgmketaaakferqhmdspdlgtddddkama*pkkkrkv*mdkkysigldigtnsvgwavit
deykvpskkfkvlgntdrhsikknligallfdsgetaeatrlkrtarrrytrrknricylqeifsnemakvddsffhrleesflveed
kkherhpifgnivdevayhekyptiyhlrkklvdstdkadlriylylahmikfrghfliegdlnpdnsdvdklfiqlvqtynqlfe
enpinasgvdakailsarlsksrrlenliaqlpgekknglfgnlialslgltpnfksnfdlaedaklqlskdtyddldnllaqigd
qyadlflaaknlsdaillsdilrvnteitkaplsasmikrydehhqdltllkalvrqqlpekykeiffdqskngyagyidggasqe
efykfikpilekmdgteellvklnredllrkqrtfdngsiphqihlgel-
hailrrqedfypflkdnrekiekiltfripyyvgplargnsr
fawmtrkseetitpwnfeevvdkgasaqsfiermtnfdknIpnekvIpkhsllyeyftvyneltkvkyvtegmrkpafIsge
qkkaivdllfktnrkvtvkqlkedyfkkiecfdsveisgvedrfnasIgtyhdllkiikdkdfldneenediledivltltlfedremi
eerlktyahlfddkvmkqlkrrrytgwgrlsrklingirdkqsgktiIdflksdgfanrnfmqlihddsltfkediqkaqvsgqgd
slhehianlagspaikkgilqtvkvvmgrhkpenivlemarenqttqkgqknsrermkrieegikelgsqilkehp
ventqlqneklylyylqngrdmyvdqeldinrlsdydvdhivpqsflkddsidnkvltrsdknrgksdnvpseevvkkmkn
ywrqllnaklitqrkfdnltkaergglseldkagfikrqlvetrqitkhvaqildsrmntkydendklirevkvitlksklvsdfrkdf
qfykvreinnyhhandaylnavgtalikkypklesefvygdykvydvrkmiakseqeigkatakyffysnimnffkteitla
ngeirkrplietngetgeivwdkgrdfatvrkvlsmpqvnivkktevqtggfskesilpkrnsdkliarkkdwdpkkyggfds -continued Sequences:

ptvaysvlvvakvekgkskklksvkellgitimerssfeknpidfleakgykevkkdliiklpkyslfelengrkrmlasagelq
kgnelalpskyvnflylashyeklkgspedneqkqlfveqhkhyldeiiegisefskrviladanldkvlsaynkhrdkpireq
aeniihlftltnlgapaafkyfdttidrkrytstkevldatlihqsitglyetridlsqlggdkkkklkl SEQ ID NO: 22
The nucleotide sequences of the substrate DNA fragment. The UTR sequences are shown in lowercase while the TrGA gene is shown in uppercase. The selected VT domain, TrGA_Sth_sgR2, is shown in bold and the 500 bp fragment applied for further loop-out experiment was shown in underlined.

gactgtctccaccatgtaattttccctgcgactccatataacgccggatcgtgaaattttcttctttcttttccttccttctcaacaa
acaacggatctgtgctttgcggtcccctgcgttcacgcgtcagggtcgactgctctgcagctcgataactccatggagccat
caacttgctatggtgtcaatcatcctatcgacaggtccaagaacaagccggcctccggctgcctcattcgctgtcgcaaga
cggcttgagtgttgtggctggaggattcgggggccccatattccaaccctttttccaaggccgtcggccggtgaggttgag
gaaaaccatgggttgcctacatattatcgatgctggtgtttggtagtagcaatgtttgcggtggcagtttgagccgagcctcgt
cttgggcttctgacccaggcaacgccatctgactagctgcgccgaaggaaggatgattcattgtacgacgccagtcaatg
gaatcttcaagtaaaagcccgacgaaccgaccatgtcagatatcagaattctcctggctggtggggttggttggagactgc
ttacggagtcgatgcctcgtgactgtcatggccgcgtccagcctcctgggactctgtccgatattatgacacgagtaaagcc
tgcatgatgtcagtttgctgcgtctcatgtcgagaacaacacacctggtgctacataggcaatactacctcgtagcttcaaa
gttgactgttttgctttgatgtctttgatcatgcccatccatcccttgtcttgcagtgcatgtggatctctacgtccagacggggag
aaagcttgtctgtgataaagtacgatgatgcattgatgcctgtggctacggcccttttatccccatcgtcatgcatctctatatta
atccaggagactctcctcctggcatgggtgagtacaagtgacgaggacatgtagaagcagagccacgcaacgtcttga
catctgtacctattttgggccaaaaatcgagacccaccagctcgtcctaccttacatgtgaagatcttagcccacaatcctac
tgttttactagtattactgcacagctgtcatcacgagtcctcggttgcttgtgaaacccagctcagctcctgagcacatgcagt
aacaccaactcaacatcatttcaccacacccaatttggacctgagggatgctgaaaactactaaacagatcccattacca
attcatggcactactacatccatacgcagcaaacatgggcttgggcttggcttctcaatgcaaaattgcccgcaaaagtcc
cggcattgtcgatgcagagatgcagatttcagcgggcgattctagggtagggcgactactactactaataccacctagtca
gtatgtatctagcaccggaggctaggcggttagtggacgggaacctggtcattccatcgcaaccaggatcccgcacttcgt
tgcgcttctgcccccacggggcgggagttggcagaggcagaatgcggagcagccccttgtctgccctggccggggcct
gttgaagcaagcagacgagagcagagcggttgagaagcggtggttgacgcttgacggtacgaagacgagcgagaat
cccgttaagccgaggctgggctcccccccccgtcatcatcatgcccatcctgctcttccagcccactcgtctccctgcctcgt
cgcctcccctccctcccccgattagctgcgcatgttctcctgacagcgtgactaatgacgcgttgccagcccattcgcctga
cgcatcccggcatctgagtctagctcgtcacgctggcaatcttggcccaggcagagcagcaagacggcgggcatgattg
ggccgtgccctggcgggcatcagctggccatccgctgccacccgagaccgcatcaccgacttgtcggatctctccgagc
agcaggaggctgatcctggccggcgagacgattgaaaagggctgccgggcccggagcaggacagcggcgagagc
gagcgagagagaggaaaagaagaaggtcgactgtcttattttcagccagccccggctcaacagaagcagaggagaa
ggcgaacgacgtcaacgacgacgacgacgacgacgaagacggtgaagtccgttagttgaagatccttgccgtcacaa
caccatctcgtggatattgctttcccctgccgttgcgttgccacctgttccctctttctcttccccccttcttcctcattccgagcgct
actggttcctactccgcagccttcggttgtgcctttctctttgtcgaccattgcaccgcccgtcgcggcacttgggccccggag
aattcggccctttcgcagcattttggccctcagttccccatggggacggtccacacttcctctcttggccctgcagaccttttgt
cgtcggtccgagtcggaagaagctcagtcttgagcgcttgagtagcatctacgcgcgaatcactggacaaagtcggcaa
gacgaagccgtcgtcgcctgctgctgctgctgttactgcgacaggcgctccgactgggggcatcggcataataaaaagat
gcccgccttcgccatggacctggccatgagccactcggcatcggctctctctctcaacgcttcctctcacacatcctccttcat
tccgcccatcATGCACGTCCTGTCGACTGCGGTGCTGCTCGGCTCCGTTGCCGTTCAA
AAGGTCCTGGGAAGACCAGGATCAAGCGGTCTGTCCGACGTCACCAAGAGGTCT
GTTGACGACTTCATCAGCACCGAGACGCCTATTGCACTGAACAATCTTCTTTGCAA
TGTTGGTCCTGATGGATGCCGTGCATTCGGCACATCAGCTGGTGCGGTGATTGCA
TCTCCCAGCACAATTGACCCGGACTGTAAGTTGGCCTTGATGAACCATATCATATA
TCGCCGAGAAGTGGACCGCGTGCTGAGACTGAGACAGACTATTACATGTGGACG
CGAGATAGCGCTCTTGTCTTCAAGAACCTCATCGACCGCTTCACCGAAACGTACG
ATGCGGGCCTGCAGCGCCGCATCGAGCAGTACATTACTGCCCAGGTCACTCTCCA
GGGCCTCTCTAACCCCTCGGGCTCCCTCGCGGACGGCTCTGGTCTCGGCGAGCC
CAAGTTTGAGTTGACCCTGAAGCCTTTCACCGGCAACTGGGGTCGACCGCAGCG
GGATGGCCCAGCTCTGCGAGCCATTGCCTTGATTGGATACTCAAAGTGGCTCATC
AACAACAACTATCAGTCGACTGTGTCCAACGTCATCTGGCCTATTGTGCGCAACGA
CCTCAACTATGTTGCCCAGTACTGGTCAGTGCTTGCTTGCTCTTGAATTACGTCTT
TGCTTGTGTGTCTAATGCCTCCACCACAGGAACCAAACCGGCTTTGACCTCTGGG
AAGAAGTCAATGGGAGCTCATTCTTTACTGTTGCCAACCAGCACCGAGGTATGAA
GCAAATCCTCGACATTCGCTGCTACTGCACATGAGCATTGTTACTGACCAGCTCTA
CAGCACTTGTCGAGGGCGCCACTCTTGCTGCCACTCTTGGCCAGTCGGGAAGCG
CTTATTCATCTGTTGCTCCCCAGGTTTTGTGCTTTCTCCAACGATTCTGGGTGTCG
TCTGGTGGATACGTCGACTCCAACAGTATGTCTTTTCACTGTTTATATGAGATTGG
CCAATACTGATAGCTCGCCTCTAGTCAACACCAACGAGGGCAGGACTGGCAAGGA
TGTCAACTCCGTCCTGACTTCCATCCACACCTTCGATCCCAACCTTGGCTGTGAC
GCAGGCACCTTCCAGCCATGCAGTGACAAAGCGCTCTCCAACCTCAAGGTTGTTG
TCGACTCCTTCCGCTCCATCTACGGCGTGAACAAGGGCATTCCTGCCGGTGCTGC
CGTCGCCATTGGCCGGTATGCAGAGGATGTGTACTACAACGGCAACCCTTGGTAT
CTTGCTACATTTGCTGCTGCCGAGCAGCTGTACGATGCCATCTACGTCTGGAAGA
AGACGGGCTCCATCACGGTGACCGCCACCTCCCTGGCCTTCTTCCAGGAGCTTGT
TCCTGGCGTGACGGCCGGGACCTACTCCAGCAGCTCTTCGACCTTTACCAACATC
ATCAACGCCGTCTCGACATACGCCGATGGCTTCCTCAGCGAGGCTGCCAAGTACG
TCCCCGCCGACGGTTCGCTGGCCGAGCAGTTTGACCGCAACAGCGGCACTCCGC
TGTCTGCGCTTCACCTGACGTGGTCGTACGCCTCGTTCTTGACAGCCACGGCCCG
TCGGGCTGGCATCGTGCCCCCCTCGTGGGCCAACAGCAGCGCTAGCACGATCCC
CTCGACGTGCTCCGGCGCGTCCGTGGTCGGATCCTACTCGCGTCCCACCGCCAC
GTCATTCCCTCCGTCGCAGACGCCCAAGCCTGGCGTGCCTTCCGGTACTCCCTAC
ACGCCCCTGCCCTGCGCGACCCCAACCTCCGTGGCCGTCACCTTCCACGAGCTC
GTGTCGACACAGTTTGGCCAGACGGTCAAGGTGGCGGGCAACGCCGCGGCCCTG -continued Sequences:

GGCAACTGGAGCACGAGCGCCGCCGTGGCTCTGGACGCCGTCAACTATGCCGAT
AACCACCCCCTGTGGATTGGGACGGTCAACCTCGAGGCTGGAGACGTCGTGGAG
TACAAGTACATCAATGTGGGCCAAGATGGCTCCGTGACCTGGGAGAGTGATCCCA
ACCACACTTACACGGTTCCTGCGGTGGCTTGTGTGACGCAGGTTGTCAAGGAGGA
CACCTGGCAGTCGTAAtgaatcggcaaggggtagtactagtagacttgtagtctgcc SEQ ID NO: 23
forward primer for SEQ ID NO: 22:
5'-gactgtctccaccatgtaatttttc-3'

SEQ ID NO: 24
reverse primer for SEQ ID NO: 22:
5'-ggcagactacaagtctactagtactac-3'

SEQ ID NO: 25
TrGA_Sth_sg R2 VT domain
TCCTGACTTCCATCCACACC

SEQ ID NO: 26
500 bp fragment applied for further loop-out experiment
gagcacatgcagtaacgccgactcggcgtcatttcgccacacccaatttggacctgagggatgctggaagctgctgagc
agatcccgttaccgattcatggcactactacatccatacgcagcaaacatgggcttgggcttggcttctcaatgcaaaattg
cccgcaaaagtcccggcattgtcgatgcagagatgcagatttcagcgggcgattctagggtagggcgactactactacta
ataccacctagtcagtatgtatctaacaccggaggctaggcggttagtggacgggaacctggtcattccatcgcaaccag
gatcccgcacttcgttgcgcttctgcccccacggggcgggagttggcagacggcagaatgcggagcaggcccttgtctgcc
ctggccgggcctgttgaagcaagcagacgagagcagagcggttgagaagcggtggttgacgcttgacggtacgaag
acgagcgagaatcccgttaagccgaggctgggc SEQ ID NO: 27
The template sequence for in vitro transcription consisting of the T7 promoter, CER domain, and the VT domain TrGA Sth sgR2. The VT domain is shown in uppercase, while the T7 promoter and CER domain region are shown in bold and lowercase, respectively.
taatacgactcactatagGGTGTGGATGGAAGTCAGGAgttttagagctagaaatagcaagttaaaataa
ggctagtccgttatcaacttgaaaaagtggcaccgagtcggtgc SEQ ID NO: 28
Forward
5'-ctttttacggttcctggc-3'

SEQ ID NO: 29
Reverse
5'-aaaagcaccgactcgg-3'

SEQ ID NO: 30
The nucleotide sequence of the TrGA knockout cassette. The pyr2 promotor, pyr2 CDS, pyr2 terminator and the 500 bp repeat sequence was shown in lowercase, italic underline, bold, and underlined, respectively.
ctcgagtttataagtgacaacatgctctcaaagcgctcatggctggcacaagcctggaaagaaccaacacaaagcata
ctgcagcaaatcagctgaattcgtcaccaattaagtgaacatcaacctgaaggcagagtatgaggccagaagcacatct
ggatcgcagatcatggattgcccctcttgttgaagatgagaatctagaaagatggcggggtatgagataagagcgatgg
gggggcacatcatcttccaagacaaacaacctttgcagagtcaggcaatttttcgtataagagcaggaggagggagtcc
agtcatttcatcagcggtaaaatcactctagacaatcttcaagatgagttctgccttgggtgacttatagccatcatcatacct
agacagaagcttgtgggatactaagaccaacgtacaagctcgcactgtacgctttgacttccatgtgaaaactcgatacg
gcgcgcctctaaattttatagctcaaccactccaatccaacctctgcatccctctcactcgtcctgatctactgttcaaatcag
agaataaggacactatccaaatccaacagaatggctaccacctcccagctgcctgcctacaagcaggacttcctcaaat
ccgccatcgacggcggcgtcctcaagtttggcagcttcgagctcaagtccaagcggatatcccccctacttcttcaacgcgg
gcgaattccacacggcgcgcctcgccggcgccatcgcctccgcctttgcaaagaccatcatcgaggcccaggagaag
gccggcctagagttcgacatcgtcttcggcccggcctacaagggcatcccgctgtgctccgccatcaccatcaagctcgg
caagctggcgccccagaacctgaaccgcgtctcctactcgtttgaccgcaagaaggccaaggaccacggcgagggcg
gcaacatcgtcggcgcttcgctcaagagcaagagggtcctgattgtcgacgacgtcatcaccgccggcaccgccaaga
gggacgccattgagaagatcaccaaggagagcggcatcgtcgccggcatcgtcatggccctggaccgcatggagaa
gctccccgctacggatggcgacgactccaagcctggaccgagtgccattggccagctgaggaaggagtacggcatcc
ccatctttgccatcctcactctggatgacattatcaatggcatgaaaggctttgctacccctgaggatatcaagaacacgga
ggattaccgtgccaagtacaaagcgactgactgattgaggcgttcaatgtcagaagggagagaaagactgaaaag
gtggaaagaagaggcaaattgttgttattattattattctatctcgaatcttctagatcttgtcgtaaataaacaagcg
taactagctagcctccgtacaactgcttgaatttgatacccgtatggagggcagttattttattttgtttttcaagatttt
ccattcgccgttgaactcgtctcacatcgcgtgtattgcccggttgcccatgtgttctcctactaccccaagtccct
cacgggttgtctcactttctttctcctttatcctccctatttttttttcaagtcagcgacagagcagtcatatggggatac
gtgcaactgggactcacaacaggccatcttatggcctaatagccggcgttggatccactagtcaattgagcacat
gcagtaacgccgactcggcgtcatttcgccacacccaatttggacctgagggatgctggaagctgctgagcagatcccgt
taccgattcatgacactactacatccatacgcagcaaacatgggcttaggcttgacttctcaatgcaaaattgcccgcaaa
agtcccggcattatcgatgcagagatgcagatttcagcgggagattctagggtagggcgactactactactaataccacct
agtcagtatgtatctagcaccggaggctaggcggttagtggacgggaacctggtcattccatcgcaaccaggatcccgc
acttcgttgcgcttctgcccccacggggcgggagttggcagaggcagaatgcggagcagccccttgtctgccctggccg
ggcctgttgaagcaagcagacgagagcagagcggttgagaagcggtggttgacgcttgacggtacgaagacgagc
gagaatcccgttaagccgaggctgggc -continued Sequences:

SEQ ID NO: 31
pyr2 promotor
ctcgagtttataagtgacaacatgctctcaaagcgctcatggctggcacaagcctggaaagaaccaacacaaagcata
ctgcagcaaatcagctgaattcgtcaccaattaagtgaacatcaacctgaaggcagagtatgaggccagaagcacatct
ggatcgcagatcatggattgccctcttgttgaagatgagaatctagaaagatggcggggtatgagataagagcgatgg
gggggcacatcatcttccaagacaaacaacctttgcagagtcaggcaattttttcgtataagagcaggaggagggagtcc
agtcatttcatcagcggtaaaatcactctagacaatcttcaagatgagttctgccttgggtgacttatagccatcatcatacct
agacagaagcttgtgggatactaagaccaacgtacaagctcgcactgtacgctttgacttccatgtgaaaactcgatacg
gcgcgcctctaaattttatagctcaaccactccaatccaacctctgcatccctctcactcgtcctgatctactgttcaaatcag
agaataaggacactatccaaatccaacaga SEQ ID NO: 32
pyr2 CDS
atggctaccacctcccagctgcctgcctacaagcaggacttcctcaaatccgccatcgacggcggcgtcctcaagtttgg
cagcttcgagctcaagtccaagcggatatccccctacttcttcaacgcgggcgaattccacacggcgcgcctcgccggc
gccatcgcctccgcctttgcaaagaccatcatcgaggcccaggagaaggccggcctagagttcgacatcgtcttcggcc
cggcctacaagggcatcccgctgtgctccgccatcaccatcaagctcggcgagctggcgccccagaacctggaccgcg
tctcctactcgtttgaccgcaaggaggccaaggaccacggcgagggcggcaacatcgtcggcgcttcgctcaagggca
agagggtcctgattgtcgacgacgtcatcaccgccggcaccgccaagagggacgccattgagaagatcaccaaggag
ggcggcatcgtcgccggcatcgtcgtggccctggaccgcatggagaagctccccgctgcggatggcgacgactccaag
cctggaccgagtgccattggcgagctgaggaaggagtacggcatcccatctttgccatcctcactctgatgacattatc
gatggcatgaagggctttgctacccctgaggatatcaagaacacggaggattaccgtgccaagtacaaggcgactgact
ga SEQ ID NO: 33
pyr2 terminator
ttgaggcgttcaatgtcagaagggagagaaagactgaaaaggtggaaagaagaggcaaattgttgttattattattattct
atctcgaatcttctagatcttgtcgtaaataaacaagcgtaactagctagcctccgtacaactgcttgaatttgatacccgtat
ggagggcagttatttatttttgtttttcaagatttccattcgccgttgaactcgtctcacatcgcgtgtattgcccggttgccatgt
gttctcctactaccccaagtccctcacggggttgtctcactttcttttctccttttatcctccctatttttttttcaagtcagcgacagagca
gtcatatggggatacgtgcaactgggactcacaacaggccatcttatggcctaatagccggcgttggatccactagtca
attg SEQ ID NO: 34
500 bp repeat sequence
agcacatgcagtaacgccgactcggcgtcatttcgccacacccaatttggacctgagggatgctggaagctgctgagca
gatcccgttaccgattcatggcactactacatccatacgcagcaaacatgggcttgggcttggcttctcaatgcaaaattgc
ccgcaaaagtcccggcattgtcgatgcagagatgcagatttcagcgggcgattctagggtagggcgactactactactaa
taccacctagtcagtatgtatctagcaccggaggctaggcggttagtggacgggaacctggtcattccatcgcaaccagg
atcccgcacttcgttgcgcttctgccccacggggcgggagttggcagaggcagaatgcggagcagcccttgtctgccc
tggccggggcctgttgaagcaagcagacgagagcagagcggttgagaagcggtggttgacgcttgacggtacgaaga
cgagcgagaatcccgttaagccgaggctgggc SEQ ID NO: 35
ggtgtttggtagtagcaatg SEQ ID NO: 36
ggcagactacaagtctactagtactac SEQ ID NO: 37
The expected nucleotide sequences of the PCR product of loop-out strains. The UTR
sequences are shown in lowercase, the partial TrGA ORF fragment is shown in
uppercase, and the 500 bp fragment retained after the loop-out (repeat sequence) is
underlined.
ggtgtttggtagtagcaatgtttgcggtggcagtttgagccgagcctcgtcttgggcttctgacccaggcaacgccatctgac
tagctgcgccgaaggaaggatgattcattgtacgacgccagtcaatggaatcttcaagtaaaagcccgacgaaccgac
catgtcagatatcagaattctcctggctggtggggttggttggagacttgcttacggagtcgatgcctcgtgactgtcatggcc
gcgtccagcctcctgggactctgtccgatattatgacacgagtcaaagcctgcatgatgtcagtttgctgcgtctcatgtcgag
aacaacacacctggtgctacataggcaatactacctcgtagcttcaaagttgactgttttgctttgatgtctttgatcatgccca
tccatcccttgtcttgcagtgcatgtggatctctacgtccagacggggagaaagcttgtctgtgataaagtacgatgatgcatt
gatgcctgtggctacggcccttttattccccatcgtcatgcatctctatattaatccaggagactctcctcctggcatgggtgagt
acaagtgacgaggacatgtagaagcagagccacgcaacgtcttgacatctgtacctattttgggcaaaaatcgagacc
caccagctcgtcctaccttacatgtgaagatcttagcccacaatcctactgttttactagtattactgcacagctgtcatcacg
agtcctcggttgcttgtgaaacccagctcagctcctgagcacatgcagtaacgccgactcggcgtcatttcgccacaccca
atttggacctgagggatgctggaagctgctgagcagatcccgttaccgattcatggcactactacatccatacgcagcaa
acatgggcttgggcttggcttctcaatgcaaaattgcccgcaaaagtcccggcattgtcgatgcagagatgcagatttcag
cgggcgattctagggtagggcgactactactactaataccacctagtcagtatgtatctagcaccggaggctaggcggtta
gtggacgggaacctggtcattccatcgcaaccaggatcccgcacttcgttgcgcttctgccccacggggcgggagttgg
cagaggcagaatgcggagcagcccttgtctgccctggccggggcctgttgaagcaagcagacgagagcagagcgg
ttgagaagcggtggttgacgcttgacggtacgaagacgagcgagaatcccgttaagccgaggctgggcTGACTTC
CATCCACACCTTCGATCCCAACCTTGGCTGTGACGCAGGCACCTTCCAGCCATGC
AGTGACAAAGCGCTCTCCAACCTCAAGGTTGTTGTCGACTCCTTCCGCTCCATCTA
CGGCGTGAACAAGGGCATTCCTGCCGGTGCTGCCGTCGCCATTGGCCGGTATGC
AGAGGATGTGTACTACAACGGCAACCCTTGGTATCTTGCTACATTTGCTGCTGCCG
AGCAGCTGTACGATGCCATCTACGTCTGGAAGAAGACGGGCTCCATCACGGTGAC
CGCCACCTCCCTGGCCTTCTTCCAGGAGCTTGTTCCTGGCGTGACGGCCGGGAC

```
CTACTCCAGCAGCTCTTCGACCTTTACCAACATCATCAACGCCGTCTCGACATACG
CCGATGGCTTCCTCAGCGAGGCTGCCAAGTACGTCCCCGCCGACGGTTCGCTGG
CCGAGCAGTTTGACCGCAACAGCGGCACTCCGCTGTCTGCGCTTCACCTGACGT
GGTCGTACGCCTCGTTCTTGACAGCCACGGCCCGTCGGGCTGGCATCGTGCCCC
CCTCGTGGGCCAACAGCAGCGCTAGCACGATCCCCTCGACGTGCTCCGGCGCGT
CCGTGGTCGGATCCTACTCGCGTCCCACCGCCACGTCATTCCCTCCGTCGCAGAC
GCCCAAGCCTGGCGTGCCTTCCGGTACTCCCTACACGCCCCTGCCCTGCGCGAC
CCCAACCTCCGTGGCCGTCACCTTCCACGAGCTCGTGTCGACACAGTTTGGCCAG
ACGGTCAAGGTGGCGGGCAACGCCGCGGCCCTGGGCAACTGGAGCACGAGCGC
CGCCGTGGCTCTGGACGCCGTCAACTATGCCGATAACCACCCCCTGTGGATTGG
GACGGTCAACCTCGAGGCTGGAGACGTCGTGGAGTACAAGTACATCAATGTGGG
CCAAGATGGCTCCGTGACCTGGGAGAGTGATCCCAACCACACTTACACGGTTCCT
GCGGTGGCTTGTGTGACGCAGGTTGTCAAGGAGGACACCTGGCAGTCGTAAtgaat
cggcaaggggtagtactagtagacttgtagtctgcc SEQ ID NO: 38
Upstream UTR sequence from SEQ ID NO: 37
ggtgtttggtagtagcaatgtttgcggtggcagtttgagccgagcctcgtcttgggcttctgacccaggcaacgccatctgac
tagctgcgccgaaggaaggatgattcattgtacgacgccagtcaatggaatcttcaagtaaaagcccgacgaaccgac
catgtcagatatcagaattctcctggctggtggggttggttggagactgcttacggagtcgatgcctcgtgactgtcatggcc
gcgtccagcctcctgggactctgtccgatattatgacacgagtaaagcctgcatgatgtcagtttgctgcgtctcatgtcgag
aacaacacacctggtgctacataggcaatactacctcgtagcttcaaagttgactgttttgcttttgatgtctttgatcatgccca
tccatccttgtcttgcagtgcatgtggatctctacgtccagacggggagaaagcttgtctgtgataaagtacgatgatgcatt
gatgcctgtggctacggcccttttatccccatcgtcatgcatctctatattaatccaggagactctcctcctggcatgggtgagt
acaagtgacgaggacatgtagaagcagagccacgcaacgtcttgacatctgtacctattttgggccaaaaatcgagacc
caccagctcgtcctaccttacatgtgaagatcttagcccacaatcctactgttttactagtattactgcacagctgtcatcacg
agtcctcggttgcttgtgaaacccagctcagctcctgagcacatgcagtaacgccgactcggcgtcatttcgccacaccca
atttggacctgagggatgctggaagctgctgagcagatcccgttaccgattcatggcactactacatccatacgcagcaa
acatgggcttgggcttggcttctcaatgcaaaattgcccgcaaaagtcccggcattgtcgatgcagagatgcagatttcag
cgggcgattctagggtagggcgactactactactaataccacctagtcagtatgtatctagcaccggaggctaggcggtta
gtggacgggaacctggtcattccatcgcaaccaggatcccgcacttcgttgcgcttctgcccccacggggcgggagttgg
cagaggcagaatgcggagcagcccttgtctgccctggccggggcctgttgaagcaagcagacgagagcagagcgg
ttgagaagcggtggttgacgcttgacggtacgaagacgagcgagaatcccgttaagccgaggctgggc SEQ ID NO: 39
Downstream UTR Sequence
Tgaatcggcaaggggtagtactagtagacttgtagtctgcc from SEQ ID NO: 37

SEQ ID NO: 40
partial TrGA ORF fragment from SEQ ID NO: 37
TGACTTCCATCCACACCTTCGATCCCAACCTTGGCTGTGACGCAGGCACCTTCCA
GCCATGCAGTGACAAAGCGCTCTCCAACCTCAAGGTTGTTGTCGACTCCTTCCGC
TCCATCTACGGCGTGAACAAGGGCATTCCTGCCGGTGCTGCCGTCGCCATTGGC
CGGTATGCAGAGGATGTGTACTACAACGGCAACCCTTGGTATCTTGCTACATTTGC
TGCTGCCGAGCAGCTGTACGATGCCATCTACGTCTGGAAGAAGACGGGCTCCATC
ACGGTGACCGCCACCTCCCTGGCCTTCTTCCAGGAGCTTGTTCCTGGCGTGACG
GCCGGGACCTACTCCAGCAGCTCTTCGACCTTTACCAACATCATCAACGCCGTCT
CGACATACGCCGATGGCTTCCTCAGCGAGGCTGCCAAGTACGTCCCCGCCGACG
GTTCGCTGGCCGAGCAGTTTGACCGCAACAGCGGCACTCCGCTGTCTGCGCTTC
ACCTGACGTGGTCGTACGCCTCGTTCTTGACAGCCACGGCCCGTCGGGCTGGCA
TCGTGCCCCCCTCGTGGGCCAACAGCAGCGCTAGCACGATCCCCTCGACGTGCT
CCGGCGCGTCCGTGGTCGGATCCTACTCGCGTCCCACCGCCACGTCATTCCCTC
CGTCGCAGACGCCCAAGCCTGGCGTGCCTTCCGGTACTCCCTACACGCCCCTGC
CCTGCGCGACCCCAACCTCCGTGGCCGTCACCTTCCACGAGCTCGTGTCGACAC
AGTTTGGCCAGACGGTCAAGGTGGCGGGCAACGCCGCGGCCCTGGGCAACTGG
AGCACGAGCGCCGCCGTGGCTCTGGACGCCGTCAACTATGCCGATAACCACCCC
CTGTGGATTGGGACGGTCAACCTCGAGGCTGGAGACGTCGTGGAGTACAAGTAC
ATCAATGTGGGCCAAGATGGCTCCGTGACCTGGGAGAGTGATCCCAACCACACTT
ACACGGTTCCTGCGGTGGCTTGTGTGACGCAGGTTGTCAAGGAGGACACCTGGC
AGTCGTAA SEQ ID NO: 41
The 500 bp fragment retained after the loop-out from SEQ ID NO: 37
agcacatgcagtaacgccgactcggcgtcatttcgccacacccaatttggacctgagggatgctggaagctgctgagca
gatcccgttaccgattcatggcactactacatccatacgcagcaaacatgggcttgggcttggcttctcaatgcaaaattgc
ccgcaaaagtcccggcattgtcgatgcagagatgcagatttcagcgggcgattctagggtagggcgactactactactaa
taccacctagtcagtatgtatctagcaccggaggctaggcggttagtggacgggaacctggtcattccatcgcaaccagg
atcccgcacttcgttgcgcttctgcccccacggggcgggagttggcagaggcagaatgcggagcagcccttgtctgccc
tggccggggcctgttgaagcaagcagacgagagcagagcggtggttgacgcttgacggtacgaaga
cgagcgagaatcccgttaagccgaggctgggc
```

That which is claimed:

1. A method for inserting a donor DNA at a target site in the genome of a filamentous fungal cell, the method comprising:
   a) introducing into a population of filamentous fungal cells a Cas9 endonuclease, a guide RNA, and a donor DNA, wherein the Cas9 endonuclease and guide RNA are capable of forming a complex that enables Cas9 endonuclease to introduce a double-strand break at a target site in a genomic locus of the genome of the fungal cells;
   b) identifying at least one fungal cell from the population in which insertion of the donor DNA at the target site in the genomic locus has occurred, wherein the Cas9 endonuclease, the guide RNA, or both are introduced transiently into the population of fungal cells, and wherein the insertion has occurred via a non-homologous insertion of the donor DNA into the genome of the fungal cells, and wherein the donor DNA is not flanked by sequences homologous to a genomic sequence in the genomic locus,
   wherein the donor DNA comprises a sequence homologous to a genomic sequence in the genomic locus, wherein the genomic sequence and the target site flank a genomic deletion target region, and wherein the insertion of the donor DNA results in the genomic sequence and the sequence homologous to the genomic sequence flanking a loop-out target region comprising the genomic deletion target region;
   c) culturing the at least one identified fungal cell from step (b) under conditions that allow loop-out of the loop-out target region; and,
   d) identifying at least one fungal cell from step (c) in the culture in which loop-out of the loop-out target region has occurred.

2. The method of claim 1, wherein the insertion of the donor DNA interrupts the expression or function of the genomic locus.

3. The method of claim 1, wherein the donor DNA comprises a gene of interest.

4. The method of claim 1, wherein the donor DNA comprises an expression cassette encoding a gene product of interest.

5. A method for deleting a target region in the genome of a filamentous fungal cell, the method comprising:
   a) introducing into a population of fungal cells a Cas9 endonuclease, a guide RNA, and a donor DNA, wherein the Cas9 endonuclease and guide RNA are capable of forming a complex that enables the Cas9 endonuclease to introduce a double-strand break at a target site in the genome of the fungal cells and allowing the donor DNA to be inserted at the target cite, wherein the donor DNA is not flanked by a sequence homologous to a genomic sequence in the genomic but comprises at only one end a sequence homologous to a genomic sequence of the fungal cells, wherein the genomic sequence and the target site flank the target region in the fungal cell genome, and wherein the donor DNA is inserted at the target site via non-homologous insertion of the donor DNA into fungal cell genome;
   b) identifying at least one fungal cell from the population in which insertion of the donor DNA at the target site has occurred;
   c) culturing the at least one identified fungal cell from step (b) under conditions that allow homologous recombination between the genomic sequence and the sequence homologous to the genomic sequence; and, d) identifying at least one fungal cell from step (c) in the culture in which deletion of the target region has occurred;
   wherein the Cas9 endonuclease, the guide RNA, or both are introduced transiently into the population of fungal cells.

6. The method of claim 1 or claim 5, wherein the Cas9 endonuclease comprises a full length Cas9 or a functional fragment thereof from a species selected from the group consisting of: Streptococcus sp., S. pyogenes, S. mutans, S. thermophilus, Campylobacter sp., C. jejuni, Neisseria sp., N. meningitides, Francisella sp., F. novicida, Pasteurella sp., and P. multocida.

7. The method of claim 6, wherein the Cas9 endonuclease or functional fragment thereof comprises an amino acid sequence that has at least 70% identity to any one of SEQ ID NOs:1 to 7.

8. The method of claim 1 or claim 5, wherein the introducing step comprises introducing a DNA construct comprising an expression cassette for the Cas9 endonuclease into the fungal cells.

9. The method of claim 8, wherein the expression cassette for the Cas9 endonuclease comprises a Cas9 coding sequence that is optimized for expression in the filamentous fungal cell.

10. The method of claim 9, wherein the Cas9 coding sequence is a Cas9 coding sequence comprising a polynucleotide sequence that is at least 70% identical to SEQ ID NO:8.

11. The method of claim 1 or claim 5, wherein the introducing step comprises introducing a DNA construct comprising an expression cassette for the guide RNA into the fungal cells.

12. The method of claim 1 or claim 5, wherein the introducing step comprises directly introducing the Cas9 endonuclease into the fungal cells.

13. The method of claim 1 or claim 5, wherein the introducing step comprises directly introducing the guide RNA into the fungal cells.

14. The method of claim 1 or claim 5, wherein the Cas9 endonuclease is operably linked to a nuclear localization signal.

15. The method of claim 1 or claim 5, wherein the filamentous fungal cell is selected from the group consisting of: *Trichoderma, Penicillium, Aspergillus, Humicola, Chrysosporium, Fusarium, Myceliophthora, Neurospora, Hypocrea,* and *Emericella*.

16. The method of claim 1 or claim 5, wherein the target site is located within a region of a gene of interest selected from the group consisting of an open reading frame, a promoter, a regulatory sequence, a terminator sequence, a regulatory element sequence, a splice site, a coding sequence, a polyubiquitination site, an intron site, and an intron enhancing motif.

\* \* \* \* \*